United States Patent
Ghosh

(10) Patent No.: US 9,381,216 B2
(45) Date of Patent: Jul. 5, 2016

(54) METHODS OF GENERATING, REPAIRING AND/OR MAINTAINING CONNECTIVE TISSUE IN VIVO

(75) Inventor: Peter Ghosh, Fairlight (AU)

(73) Assignee: MESOBLAST, INC., New York, NY (US)

( * ) Notice: Subject to any disclaimer, the term of this patent is extended or adjusted under 35 U.S.C. 154(b) by 722 days.

(21) Appl. No.: 12/452,767

(22) PCT Filed: Aug. 6, 2008

(86) PCT No.: PCT/AU2008/001137
§ 371 (c)(1),
(2), (4) Date: Apr. 5, 2010

(87) PCT Pub. No.: WO2009/018613
PCT Pub. Date: Feb. 12, 2009

(65) Prior Publication Data
US 2010/0203020 A1   Aug. 12, 2010

Related U.S. Application Data

(60) Provisional application No. 61/133,111, filed on Jun. 25, 2008.

(30) Foreign Application Priority Data

Aug. 6, 2007   (AU) .............................. 2007904212

(51) Int. Cl.
| | | |
|---|---|---|
| A01N 63/00 | (2006.01) | |
| A61K 35/28 | (2015.01) | |
| A61K 31/728 | (2006.01) | |
| C12N 5/0775 | (2010.01) | |
| A61K 35/12 | (2015.01) | |

(52) U.S. Cl.
CPC ............... *A61K 35/28* (2013.01); *A61K 31/728* (2013.01); *C12N 5/0663* (2013.01); *A61K 2035/124* (2013.01); *C12N 2501/905* (2013.01)

(58) Field of Classification Search
None
See application file for complete search history.

(56) References Cited

U.S. PATENT DOCUMENTS

2003/0069639 A1   4/2003   Sander et al.

FOREIGN PATENT DOCUMENTS

AU       2006200478 A1   2/2006
WO   WO 2006/032092 A1   3/2006

OTHER PUBLICATIONS

Herrera et al., Kidney International, 2007, vol. 72, p. 430-441.*
Liu et al., Tissue Engineering, 2006, vol. 12, No. 12, p. 3405-3416.*
Acosta et al., Neurosurg Focus, 2005, vol. 19, No. 3:E4, p. 1-6.*
Miura et al., PNAS, 2005, vol. 102, No. 39, p. 14022-14027.*
NPL search results, 1 page of PDF, Oct. 8, 2013.*
Le Blanc, K., Cytotherapy, 2006, vol. 8, No. 6, p. 559-561.*
International Search Report issued by the International Searching Authority (ISA/AU) on Sep. 26, 2008 in connection with International Application No. PCT/AU2008/001137.
WO 2001/080865 A2 (Osiris Pharmaceuticals Inc.), published Nov. 1, 2001 (abstract, p. 1 lines 7-13, p. 5 and p. 23 example 3).
J.M. Murphy et al. "Stem Cell Therapy in a Caprine Model of Osteoarthritis" Arthritis & Rheumatism, vol. 48 No. 12, published Dec. 2003 (abstract, p. 3465, left-hand column, lines 6-11 and p. 3472, left-hand column, lines 1-10).
WO/2001/035968 A1 (Children's Medical Center Corporation) published May 25, 2001 (abstract, p. 3 lines 13-20 and p. 4 lines 11-15).
WO 2002/070030 A1 (Fidia Advanced Biopolymers S.R.L.) Sep. 12, 2002 (abstract, p. 1 lines 11-14, p. 4 lines 6-16 and pp. 5-6 lines 28-5).
WO 2005/082433 A1 (Fidia Advanced Bioplymers S.R.L.) Sep. 9, 2005 (abstract and p. 2 lines 28-32).
WO 2004/104166 A2 (La Jolla Institute for Molecular Medicine) Dec. 2, 2004 (p. 9 lines 11-13 and p. 2 lines 11-14).
WO 1997/018842 A1 (Fidia Advanced Biopolymers S.R.L.) May 29, 1997 (abstract, claims 1, 7,and 8).
Otsuka, E et al. "Characterization of osteoblastic differentiation of stromal cell line ST2 that is induced by absorbic acid" American Journal of Physiology Cell Physiology, vol. 277, 1999, pp. 132-138 (p. 135, paragraph 1 under Discussion).
WO 2008/073631 A2 (The Regents of the University of California) Jun. 19, 2008 (claims 1, 12, 13, 17, and 18).
First Office Action issued Nov. 27, 2012 in connection with Australian Patent Application No. AU 2008286244.
M. Radice et al., "Hyaluronan-based biopolymers as delivery vehicles for bone-marrow-derived mesenchymal progenitors," Journal of Biomedical Research Materials Part A, vol. 50 Issue 2, pp. 101-109, published 1999 (abstract, p. 101, right-hand col. lines 9-16, p. 102, left-hand column lines 1-3 and p. 107, right-hand column lines 1-3.
English translation of Office Action dated Apr. 9, 2013, issued in connection with Japanese Patent Application No. 2010-519309.
Extended European Search Report issued Aug. 10, 2011 in connection with European Patent Application No. EP 08782887.7.

* cited by examiner

*Primary Examiner* — Kade Ariani
(74) *Attorney, Agent, or Firm* — John P. White; Cooper & Dunham LLP

(57) ABSTRACT

This invention relates to a method for generating, repairing and/or maintaining connective tissue in a subject. In one embodiment, the invention relates to a method for generating, repairing and/or maintaining cartilage tissue in a subject. The present invention also relates to a method of treating and/or preventing a disease in a subject arising from degradation and inflammation of connective tissue.

14 Claims, 38 Drawing Sheets

METHODS OF GENERATING, REPAIRING AND/OR MAINTAINING CONNECTIVE TISSUE IN VIVO

This application is a §371 national stage of PCT International Application No. PCT/AU2008/001137, filed Aug. 6, 2008, and claims the benefit of U.S. Provisional Application No. 61/133,111, filed Jun. 25, 2008, and priority of Australian Patent Application No. 2007904212, filed Aug. 6, 2007, the contents of each of which are hereby incorporated by reference into this application.

FIELD OF THE INVENTION

This invention relates to a method for generating, repairing and/or maintaining connective tissue in a subject. The present invention also relates to a method of treating and/or preventing a disease in a subject arising from degradation and inflammation of connective tissue.

BACKGROUND OF THE INVENTION

Non-hematopoietic progenitor cells that reside in the body and give rise to multipotential cells when isolated are referred to as Mesenchymal Precursor Cells (MPCs). More specifically, purified MPCs are capable of forming very large numbers of multipotential cell colonies.

Simmons et al. (1994) describes enrichment of MPCs from freshly harvested bone marrow cells by selecting for cells that express the STRO-1 cell surface marker. As explained by the authors at pages 272-273, it is known that bone marrow cells contain a proportion of MPCs that are capable of giving rise to CFU-F. These CFU-F in turn are capable of giving rise under appropriate conditions to a broad spectrum of fully differentiated connective tissue, including cartilage, bone, adipose tissue, fibrous tissue and myelosupportive stroma.

MPCs and CFU-F are typically present at a very low incidence in bone marrow cells (typically between 0.05%-0.001%) and this rarity has been a major limitation to their study in the past. An important finding discussed by Simmons et al. (1994) was the identification that these MPCs could be enriched from freshly isolated bone marrow cells to some extent by selecting for STRO-1 positive cells. In particular, the selection of STRO-1 positive cells enabled isolation of MPCs (and resultant CFU-F) free of contaminating hemopoietic progenitors.

WO 01/04268 provided a further important advance in the enrichment of MPCs by identifying a subpopulation within this fraction of STRO-1 positive cells that contains MPCs. In particular, WO 01/04268 describes the sorting of the STRO-1 positive cell population into three subsets: STRO-1$^{dull}$, STRO-1$^{intermediate}$ and STRO-1$^{bright}$. Clonogenic assays for CFU-F in the different sorted subpopulations demonstrated that the vast majority of the MPCs are contained within the STRO-1$^{bright}$ fraction.

WO 2004/085630 discloses for the first time that MPCs are present in perivascular tissue. One of the benefits of this finding is that it greatly expands the range of source tissues from which MPCs can be isolated or enriched and there is no longer an effective restriction on the source of MPCs to bone marrow. The tissues from which MPCs can be isolated according to the methods described in WO 2004/085630 include human bone marrow, dental pulp, adipose tissue, skin, spleen, pancreas, brain, kidney, liver and heart. The MPCs isolated from perivascular tissue are positive for the cell surface marker 3G5. They can therefore be isolated by enriching for cells carrying the 3G5 marker, or by enriching for an early developmental surface marker present on perivascular cells such as CD146 (MUC18), VCAM-1, or by enriching for high level expression of the cell surface marker STRO-1.

The avascular connective tissues are generally located at anatomical sites within the musculoskeletal system that require appreciable movement. These freely movable joints are responsible for the majority of articulations in mammals. In synovial joints the contact surfaces of two opposing bones are covered by hyaline cartilages which glide effortlessly over each other because of the presence of a low friction lubricant in synovial fluid produced by the cells lining the joint capsule which overlays and connects the long bones. In the spinal column articulation is achieved by connection of the rigid vertebral bones by means of a flexible fibrocartilagenous ring (the annulus fibrosus) that encapsulates a hydrated gelatinous mass (the nucleus pulposus), populated by chondrocyte like cells similar to those present in hyaline cartilage. Irrespective of the type and location of these avascular connective tissue they all contain cells which synthesise an extracellular matrix which is rich in highly negatively charged proteoglycans, which imbibe water molecules together with the fibrous protein, type II collagen, which confers high tensile strength.

Avascular connective tissues such as hyaline cartilage, the inner two thirds of the meniscus and the intervertebral disc have limited repair capabilities and when injured may respond by the production of a functionally inferior fibrocartilagenous scar tissue. Through a multitude of factors, dominated by aging, genetics, hormonal status and physical injury these avascular connectives often fail leading to the widespread clinical problems of disc degeneration, back pain and osteoarthritis.

Current medical therapies normally used to treat the symptoms arising from the failure of these connective tissues, for the most part, do little to redress the underlying pathology responsible for producing the symptoms and in many instances may even exacerbate the problem by down regulating the capacity of the resident cells to synthesis the structural components of the tissue extracellular matrix. Ideally, therapeutic treatments should be at least chondroprotective but even provide the conditions which enhance matrix biosynthesis and effect repair and restoration of the injured connective tissues.

SUMMARY OF THE INVENTION

The present inventors have now made the surprising finding that intra-articular administration of MPCs provides a chondroprotective effect in joints with pre-existing osteoarthritis, and leads to generation and growth of cartilage tissue in synovial joints and in the nucleus pulposus of the intervertebral discs. This finding indicates that MPCs or their progeny, or supernatant or soluble factors derived from these MPCs, can be used to protect or repair damaged connective tissues as well as generate new functional tissue at sites of degeneration or injury.

Accordingly, the present invention provides a method of treating and/or preventing a disease in a subject arising from degradation and/or inflammation of connective tissue, the method comprising administering to the subject MPCs and/or progeny cells thereof and/or soluble factors derived therefrom.

In one embodiment of the invention, the connective tissue is rich in proteoglycans. The connective tissue may be cartilage, for example, hyaline cartilage. In another embodiment, the disease results in a defect in the cartilage.

In another embodiment, the method comprises administering to the subject MPCs and/or progeny cells thereof and/or soluble factors derived therefrom, wherein the MPCs and/or progeny cells and/or soluble factors are not directly administered into the defect.

For example, administration may me made into a joint space in order to treat or prevent defects in the cartilage on the articular surfaces of bones that form that joint. Similarly, administration may be made into an invertebral disc space in order to treat or prevent defects in the surrounding discs. In another example, administration is made intravenously at a site near the cartilage defect.

The MPCs and/or progeny cells and/or soluble factors may be administered by intra-articular injection. The intra-articular injection may be made into any joint of the body which is near to a site of a cartilage defect, or a potential cartilage defect. For example, the intra-articular injection may be made into a knee joint, hip joint, ankle joint, shoulder joint, elbow joint, wrist joint, hand or finger joint or a joint of the foot, or an invertebral disc joint.

In another embodiment of the invention, administration of the MPCs and/or progeny cells and/or soluble factors results in preservation or generation of cartilage that is rich in proteoglycans and type II collagen. An example of a cartilage that is rich in proteoglycans and type II collagen is hyaline cartilage. Preferably the cartilage preserved or generated by the method of the present invention is not fibrocartilage, which is rich in type I collagen, very low in type II collagen and contains less proteoglycan than hyaline cartilage.

Examples of diseases "arising from degradation and/or inflammation of connective tissue" include, but are not limited to, tendonitis, back pain, rotary cuff tendon degradation, Carpal tunnel syndrome, DeQuervain's syndrome, degenerative cervical and/or lumber discs, intersection syndrome, reflex sympathetic dystrophy syndrome (RSDS), stenosing tenosynovitis, epicondylitis, tenosynovitis, thoracic outlet syndrome, ulnar nerve entrapment, radial tunnel syndrome, repetitive strain injury (RSI). Examples of diseases that are associated with degradation and/or inflammation of hyaline cartilage include, but are not limited to arthritis such as osteoarthritis, rheumatoid arthritis, psoriatic arthritis, and seronegative arthritis, arthritis associated with inflammatory bowel disease or ankylosing spondylitis and degenerate invertebral disc disorders.

In another preferred embodiment, the method further comprises administering hyaluronic acid (HA). HA can be administered in the same or different composition as the cells, supernatant and/or factor(s).

The present invention also provides a composition comprising MPCs and/or progeny cells thereof and hyaluronic acid.

The results presented herein indicate for the first time that soluble factors released by the implanted cultured MPCs are supportive of connective tissue protection, generation and growth.

Accordingly, the present invention also provides a composition comprising;
i) supernatant, or one or more soluble factors, derived from mesenchymal precursor cells (MPCs) and/or progeny cells thereof, and
ii) hyaluronic acid.

In a further aspect, the present invention provides for the use of supernatant, or one or more soluble factors, derived from mesenchymal precursor cells (MPCs) and/or progeny cells thereof for treating and/or preventing a disease in a subject arising from degradation and/or inflammation of connective tissue.

The present invention is applicable to a wide range of animals. For example, the subject may be a mammal such as a human, dog, cat, horse, cow, or sheep. In one embodiment the subject is a human.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

DETAILED DESCRIPTION OF PREFERRED EMBODIMENTS OF THE INVENTION

General Techniques and Selected Definitions

Figure 1:
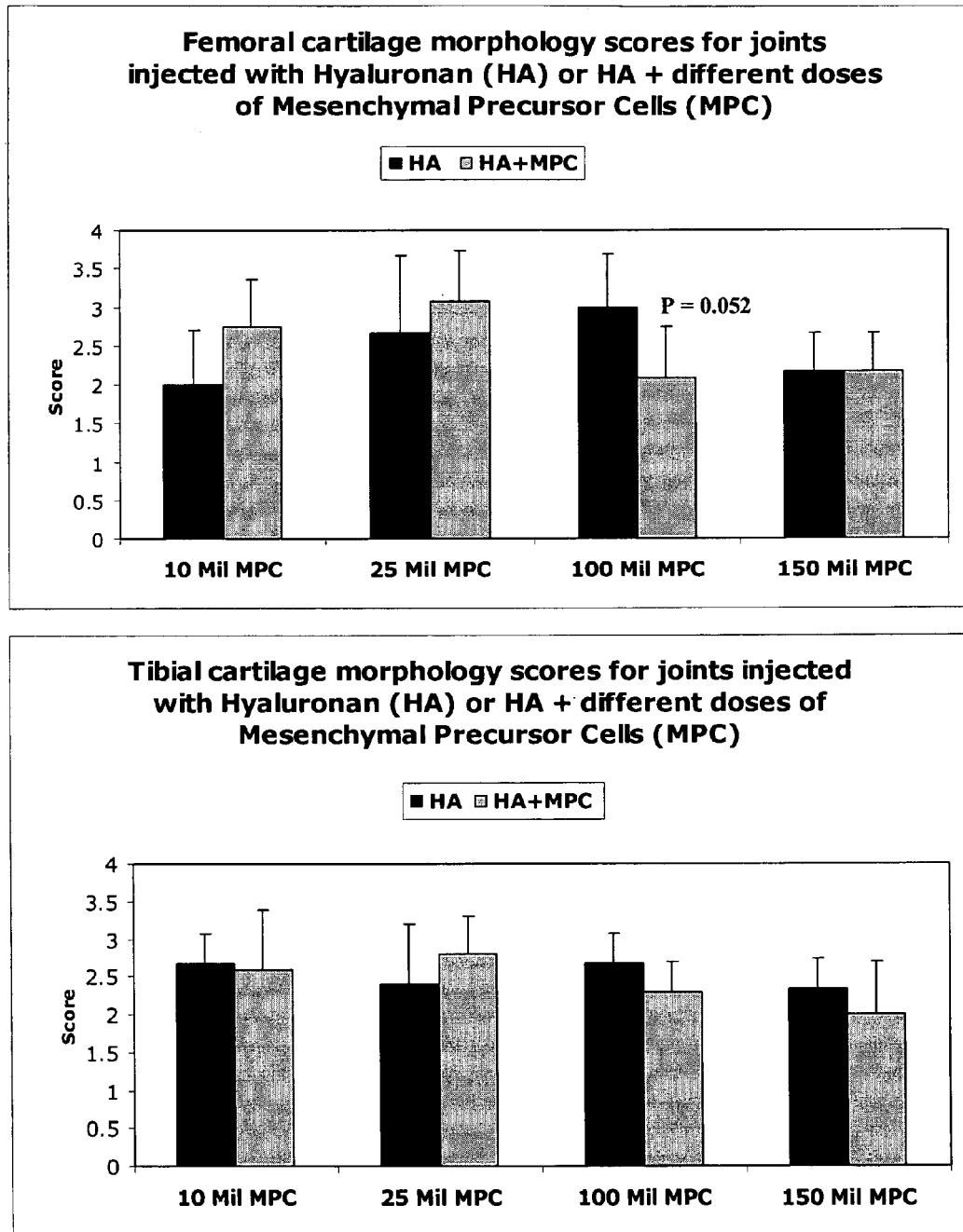
FIG. 1. Means±SD of femoral and tibial cartilage morphology scores 12 weeks post-meniscectomy for joints injected with Hyaluronan (HA) or HA plus different doses of Mesenchymal Precursor Cells (MPC).
Figure 1:
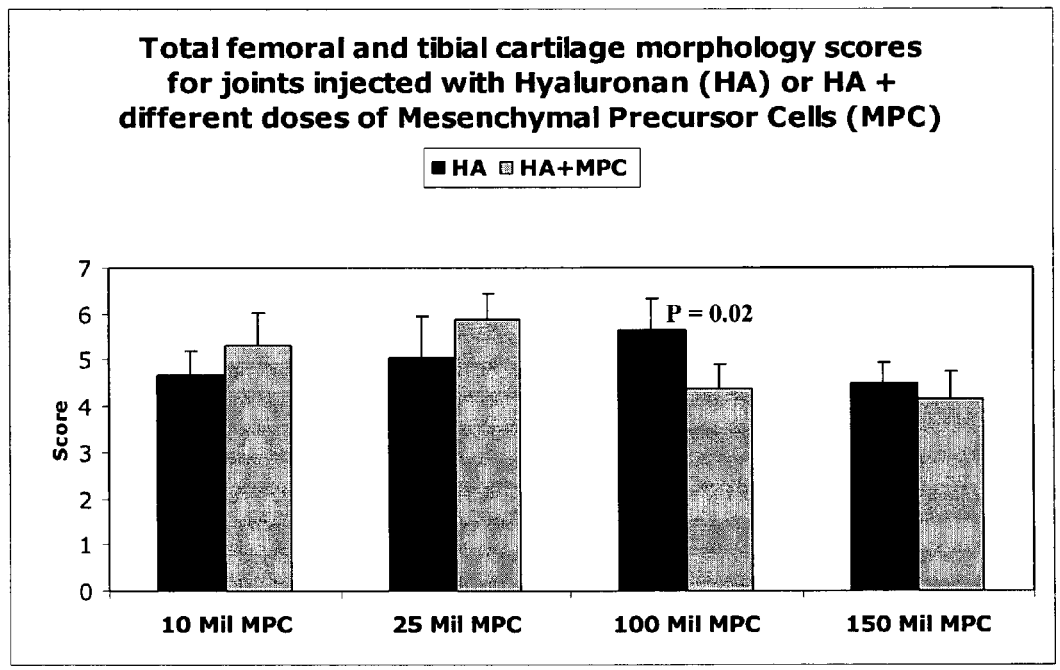

Unless specifically defined otherwise, all technical and scientific terms used herein shall be taken to have the same meaning as commonly understood by one of ordinary skill in the art (e.g., in cell culture, stem cell biology, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the terms "treating", "treat" or "treatment" include administering a therapeutically effective amount of supernatant, soluble factors and/or cells as defined herein sufficient to reduce or eliminate at least one symptom of the specified condition.

As used herein, the terms "preventing", "prevent" or "prevention" include administering a therapeutically effective amount of supernatant, soluble factors and/or cells as defined herein sufficient to stop or hinder the development of at least one symptom of the specified condition.

As used herein, the term "derived from mesenchymal precursor cells" refers to supernatant, and/or one or more soluble factors, produced from the in vitro culturing of mesenchymal precursor cells and/or progeny cells thereof.

As used herein, the term "supernatant" refers to the non-cellular material produced following the in vitro culturing of mesenchymal precursor cells, and/or progeny cells thereof, in a suitable medium, preferably liquid medium. Typically, the supernatant is produced by culturing the cells in the medium under suitable conditions and time, followed by removing the cellular material by a process such as centrifugation. The supernatant may or may not have been subjected to further purification steps before administration. In preferred embodiment, the supernatant comprises less than $10^5$, more preferably less than $10^4$, more preferably less than $10^3$ and even more preferably no live cells.

As used herein, the term "one or more soluble" factors refers to molecules, typically proteins, secreted by the MPCs, and/or progeny cells thereof, during culture.

Mesenchymal Precursor Cells (MPCs) or Progeny Cells, and Supernatant or One or More Soluble Factors Derived Therefrom As used herein, "MPC" are non-hematopoietic STRO-1$^+$ progenitor cells that are capable of forming large numbers of multipotential cell colonies.

Mesenchymal precursor cells (MPCs) are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into different germ lines such as mesoderm, endoderm and ectoderm. Thus, MPCs are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues. Mesenchymal precursor cells thus non-hematopoietic progenitor cells which divide to yield daughter cells that are either stem cells or are precursor cells which in time will irreversibly differentiate to yield a phenotypic cell.

In a preferred embodiment, the MPCs are enriched from a sample obtained from a subject. The terms 'enriched', 'enrichment' or variations thereof are used herein to describe a population of cells in which the proportion of one particular cell type or the proportion of a number of particular cell types is increased when compared with the untreated population.

In a preferred embodiment, the cells used in the present invention are also TNAP$^+$, VCAM-1$^+$, THY-1$^+$, STRO-2$^+$, CD45$^+$, CD146$^+$, 3G5$^+$ or any combination thereof. Preferably, the STRO-1$^+$ cells are STRO-1$^{bright}$. Preferably, the STRO-1$^{bright}$ cells are additionally one or more of VCAM-1$^+$, THY-1$^+$, STRO-2$^+$ and/or CD146$^+$.

In one embodiment, the mesenchymal precursor cells are perivascular mesenchymal precursor cells as defined in WO 2004/85630.

When we refer to a cell as being "positive" for a given marker it may be either a low (lo or dim) or a high (bright, bri) expresser of that marker depending on the degree to which the marker is present on the cell surface, where the terms relate to intensity of fluorescence or other colour used in the colour sorting process of the cells. The distinction of lo (or dim or dull) and bri will be understood in the context of the marker used on a particular cell population being sorted. When we refer herein to a cell as being "negative" for a given marker, it does not mean that the marker is not expressed at all by that cell. It means that the marker is expressed at a relatively very low level by that cell, and that it generates a very low signal when detectably labelled.

The term "bright", when used herein, refers to a marker on a cell surface that generates a relatively high signal when detectably labelled. Whilst not wishing to be limited by theory, it is proposed that "bright" cells express more of the target marker protein (for example the antigen recognised by STRO-1) than other cells in the sample. For instance, STRO-1$^{bri}$ cells produce a greater fluorescent signal, when labelled with a FITC-conjugated STRO-1 antibody as determined by FACS analysis, than non-bright cells (STRO-1$^{dull/dim}$). Preferably, "bright" cells constitute at least about 0.1% of the most brightly labelled bone marrow mononuclear cells contained in the starting sample. In other embodiments, "bright" cells constitute at least about 0.1%, at least about 0.5%, at least about 1%, at least about 1.5%, or at least about 2%, of the most brightly labelled bone marrow mononuclear cells contained in the starting sample. In a preferred embodiment, STRO-1$^{bright}$ cells have 2 log magnitude higher expression of STRO-1 surface expression. This is calculated relative to "background", namely cells that are STRO-1$^-$. By comparison, STRO-1$^{dim}$ and/or STRO-1$^{intermediate}$ cells have less than 2 log magnitude higher expression of STRO-1 surface expression, typically about 1 log or less than "background".

When used herein the term "TNAP" is intended to encompass all isoforms of tissue non-specific alkaline phosphatase. For example, the term encompasses the liver isoform (LAP), the bone isoform (BAP) and the kidney isoform (KAP). In a preferred embodiment, the TNAP is BAP. In a particularly preferred embodiment, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in a preferred embodiment, the MPCs are capable of giving rise to clonogenic CFU-F.

It is preferred that a significant proportion of the multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In another embodiment, the MPCs are not capable of giving rise, upon culturing, to hematopoietic cells.

The present invention also relates to use of supernatant or soluble factors obtained derived from MPC and/or progeny cells thereof (the latter also being referred to as expanded cells) which are produced from in vitro culture. Expanded cells of the invention may a have a wide variety of phenotypes depending on the culture conditions (including the number and/or type of stimulatory factors in the culture medium), the number of passages and the like. In certain embodiments, the progeny cells are obtained after about 2, about 3, about 4, about 5, about 6, about 7, about 8, about 9, or about 10 passages from the parental population. However, the progeny cells may be obtained after any number of passages from the parental population.

The progeny cells may be obtained by culturing in any suitable medium. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. Similarly, a powder mixture that when mixed with water or other liquid becomes suitable for cell culture, may be termed a "powdered medium".

In an embodiment, progeny cells useful for the methods of the invention are obtained by isolating TNAP+MPCs from bone marrow using magnetic beads labelled with the STRO-3 antibody, and then culture expanding the isolated cells (see Gronthos et al. (1995) for an example of suitable culturing conditions).

In one embodiment, such expanded cells (progeny) (at least after 5 passages) can be TNAP-, CC9+, HLA class I+, HLA class II-, CD14-, CD19-, CD3-, CD11a-c-, CD31-, CD86- CD34- and/or CD80-. However, it is possible that under different culturing conditions to those described herein that the expression of different markers may vary. Also, whilst cells of these phenotypes may predominate in the expended cell population it does not mean that there is a minor proportion of the cells do not have this phenotype(s) (for example, a small percentage of the expanded cells may be CC9-). In one preferred embodiment, expanded cells still have the capacity to differentiate into different cell types.

In one embodiment, an expended cell population used to obtain supernatant or soluble factors, or cells per se, comprises cells wherein at least 25%, more preferably at least 50%, of the cells are CC9+.

In another embodiment, an expended cell population used to obtain supernatant or soluble factors, or cells per se, comprises cells wherein at least 40%, more preferably at least 45%, of the cells are STRO-1+.

In a further embodiment, the expanded cells may express markers selected from the group consisting of LFA-3, THY-1, VCAM-1, ICAM-1, PECAM-1, P-selectin, L-selectin, 3G5, CD49a/CD49b/CD29, CD49c/CD29, CD49d/CD29, CD 90, CD29, CD18, CD61, integrin beta, 6-19, thrombomodulin, CD10, CD13, SCF, PDGF-R, EGF-R, IGF1-R, NGF-R, FGF-R, Leptin-R, (STRO-2=Leptin-R), RANKL, STRO-1$^{bright}$ and CD146 or any combination of these markers.

In one embodiment, the progeny cells are Multipotential Expanded MPC Progeny (MEMPs) as defined in WO 2006/032092. Methods for preparing enriched populations of MPC from which progeny may be derived are described in WO 01/04268 and WO 2004/085630. In an in vitro context MPCs will rarely be present as an absolutely pure preparation and will generally be present with other cells that are tissue specific committed cells (TSCCs). WO 01/04268 refers to harvesting such cells from bone marrow at purity levels of about 0.1% to 90%. The population comprising MPC from which progeny are derived may be directly harvested from a tissue source, or alternatively it may be a population that has already been expanded ex vivo.

For example, the progeny may be obtained from a harvested, unexpanded, population of substantially purified MPC, comprising at least about 0.1, 1, 5, 10, 20, 30, 40, 50, 60, 70, 80 or 95% of total cells of the population in which they are present. This level may be achieved, for example, by selecting for cells that are positive for at least one marker selected from the group consisting of TNAP, STRO-1$^{bright}$, 3G5+, VCAM-1, THY-1, CD146 and STRO-2.

MEMPS can be distinguished from freshly harvested MPCs in that they are positive for the marker STRO-1$^{bri}$ and negative for the marker Alkaline phosphatase (ALP). In contrast, freshly isolated MPCs are positive for both STRO-1$^{bri}$ and ALP. In a preferred embodiment of the present invention, at least 15%, 20%, 30%, 40%, 50%, 60%, 70%, 80%, 90% or 95% of the administered cells have the phenotype STRO-1$^{bri}$, ALP-. In a further preferred embodiment the MEMPS are positive for one or more of the markers Ki67, CD44 and/or CD49c/CD29, VLA-3, $\alpha3\beta1$. In yet a further preferred embodiment the MEMPs do not exhibit TERT activity and/or are negative for the marker CD18.

The MPC starting population may be derived from any one or more tissue types set out in WO 01/04268 or WO 2004/085630, namely bone marrow, dental pulp cells, adipose tissue and skin, or perhaps more broadly from adipose tissue, teeth, dental pulp, skin, liver, kidney, heart, retina, brain, hair follicles, intestine, lung, spleen, lymph node, thymus, pancreas, bone, ligament, bone marrow, tendon and skeletal muscle.

It will be understood that in performing the present invention, separation of cells carrying any given cell surface marker can be effected by a number of different methods, however, preferred methods rely upon binding a binding agent to the marker concerned followed by a separation of those that exhibit binding, being either high level binding, or low level binding or no binding. The most convenient binding agents are antibodies or antibody based molecules, preferably being monoclonal antibodies or based on monoclonal antibodies because of the specificity of these latter agents. Antibodies can be used for both steps, however other agents might also be used, thus ligands for these markers may also be employed to enrich for cells carrying them, or lacking them.

The antibodies or ligands may be attached to a solid support to allow for a crude separation. The separation techniques preferably maximise the retention of viability of the fraction to be collected. Various techniques of different efficacy may be employed to obtain relatively crude separations. The particular technique employed will depend upon efficiency of separation, associated cytotoxicity, ease and speed of performance, and necessity for sophisticated equipment and/or technical skill. Procedures for separation may include, but are not limited to, magnetic separation, using antibody-coated magnetic beads, affinity chromatography and "panning" with antibody attached to a solid matrix. Techniques providing accurate separation include but are not limited to FACS.

It is preferred that the method for isolating MPCs, for example, comprises a first step being a solid phase sorting step utilising for example MACS recognising high level expression of STRO-1. A second sorting step can then follow, should that be desired, to result in a higher level of precursor cell expression as described in patent specification WO 01/14268. This second sorting step might involve the use of two or more markers.

The method obtaining MPCs might also include the harvesting of a source of the cells before the first enrichment step using known techniques. Thus the tissue will be surgically removed. Cells comprising the source tissue will then be separated into a so called single cells suspension. This separation may be achieved by physical and or enzymatic means.

Once a suitable MPC population has been obtained, it may be cultured or expanded by any suitable means to obtain MEMPs.

In one embodiment, the cells are taken from the subject to be treated, cultured in vitro using standard techniques and used to obtain supernatant or soluble factors or expanded cells for administration to the subject as an autologous or allogeneic composition. In an alternative embodiment, cells of one or more of the established human cell lines are used to obtain the supernatant or soluble factors. In another useful embodiment of the invention, cells of a non-human animal (or if the patient is not a human, from another species) are used to obtain supernatant or soluble factors.

The invention can be practised using cells from any non-human animal species, including but not limited to non-human primate cells, ungulate, canine, feline, lagomorph, rodent, avian, and fish cells. Primate cells with which the invention may be performed include but are not limited to cells of chimpanzees, baboons, cynomolgus monkeys, and any other New or Old World monkeys. Ungulate cells with which the invention may be performed include but are not limited to cells of bovines, porcines, ovines, caprines, equines, buffalo and bison. Rodent cells with which the invention may be performed include but are not limited to mouse, rat, guinea pig, hamster and gerbil cells. Examples of lagomorph species with which the invention may be performed include domesticated rabbits, jack rabbits, hares, cottontails, snowshoe rabbits, and pikas. Chickens (*Gallus gallus*) are an example of an avian species with which the invention may be performed.

Cells useful for the methods of the invention may be stored before use, or before obtaining the supernatant or soluble factors. Methods and protocols for preserving and storing of eukaryotic cells, and in particular mammalian cells, are well known in the art (cf., for example, Pollard, J. W. and Walker, J. M. (1997) Basic Cell Culture Protocols, Second Edition, Humana Press, Totowa, N.J.; Freshney, R. I. (2000) Culture of Animal Cells, Fourth Edition, Wiley-Liss, Hoboken, N.J.). Any method maintaining the biological activity of the isolated stem cells such as mesenchymal stem/progenitor cells, or progeny thereof, may be utilized in connection with the present invention. In one preferred embodiment, the cells are maintained and stored by using cryo-preservation.

Administration and Compositions
Supernatant or Soluble Factors

The methods of the present invention may involve administering MPC-derived supernatant or soluble factors, topically, systematically, or locally such as within an implant or device.

In one particular embodiment the invention involves administering MPC-derived supernatant or soluble factors systemically to the subject. For example, the supernatant or soluble factors may be administered by subcutaneous or intramuscular injection.

This embodiment of the invention may be useful for the treatment of systemic degenerative diseases where generation or repair of particular tissues is desirable. Examples of systemic degenerative diseases that can be treated in this way include osteoporosis or fractures, or degenerative diseases of cartilage.

The MPC-derived supernatant or soluble factors may also be used to treat patients requiring the repair or replacement of cartilage tissue resulting from disease or trauma or failure of the tissue to develop normally, or to provide a cosmetic function, such as to augment facial or other features of the body. Treatment may entail the use of the supernatant or soluble factors to produce new cartilage tissue and/or maintain existing cartilage tissue. For example, MPC-derived supernatant or soluble factors may be used to treat a cartilage condition, for example, rheumatoid arthritis or osteoarthritis or a traumatic or surgical injury to cartilage.

Suspensions comprising MPC-derived supernatant or soluble factors may be prepared as appropriate oily suspensions for injection. Suitable lipophilic solvents or vehicles include fatty oils such as sesame oil; or synthetic fatty acid esters, such as ethyl oleate or triglycerides; or liposomes. Suspensions to be used for injection may also contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Sterile injectable solutions can be prepared by incorporating the supernatant or soluble factors in the required amount in an appropriate solvent with one or a combination of ingredients enumerated above, as required, followed by filtered sterilization. Generally, dispersions are prepared by incorporating the supernatant or soluble factors into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, the supernatant or soluble factors may be formulated with one or more additional compounds that enhance its solubility.

Cellular Compositions

In one embodiment, cellular compositions of the invention are administered as undifferentiated cells, i.e., as cultured in Growth Medium. Alternatively, the cellular compositions may be administered following culturing.

The cellular compositions useful for the present invention may be administered alone or as admixtures with other cells. Cells that may be administered in conjunction with the compositions of the present invention include, but are not limited to, other multipotent or pluripotent cells or chondrocytes, chondroblasts, osteocytes, osteoblasts, osteoclasts, bone lining cells, stem cells, or bone marrow cells. The cells of different types may be admixed with a composition of the invention immediately or shortly prior to administration, or they may be co-cultured together for a period of time prior to administration.

In some embodiments of the invention, it may not be necessary or desirable to immunosuppress a patient prior to initiation of therapy with cellular compositions. Accordingly, transplantation with allogeneic, or even xenogeneic, MPCs or progeny thereof may be tolerated in some instances.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device. The cells may be encapsulated in a capsule that is permeable to nutrients and oxygen required by the cell and therapeutic factors the cell is yet impermeable to immune humoral factors and cells. Preferably the encapsulant is hypoallergenic, is easily and stably situated in a target tissue, and provides added protection to the implanted structure. These and other means for reducing or eliminating an immune response to the transplanted cells are known in the art. As an alternative, the cells may be genetically modified to reduce their immunogenicity.

General

A "therapeutically effective amount" refers to an amount effective, at dosages and for periods of time necessary, to achieve the desired effect.

A "prophylactically effective amount" refers to an amount effective, at dosages and for periods of time necessary, to achieve the desired prophylactic result, such as preventing or inhibiting cell apoptosis or tissue damage.

The amount of supernatant or soluble factors, or MPCs or progeny thereof to be administered may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier.

It will be appreciated that the supernatant or soluble factors or MPCs or progeny thereof may be administered in the form of a composition comprising a pharmaceutically acceptable carrier or excipient.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically should be sterile and stable under the conditions of manufacture and storage. The composition can be formulated as a solution, microemulsion, liposome, or other ordered structure. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the stimulatory factor may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The supernatant or soluble factors or cell compositions may be administered in combination with an appropriate matrix, for instance, to provide slow release of the soluble factors.

The choice of matrix material is based on biocompatibility, biodegradability, mechanical properties, cosmetic appearance and interface properties. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

The MPC-derived supernatant or soluble factors, MPCs or progeny thereof may be surgically implanted, injected, delivered (e.g., by way of a catheter or syringe), or otherwise administered directly or indirectly to the site in need of repair or augmentation. Routes of administration of the MPC-derived supernatant or soluble factors include intramuscular, ophthalmic, parenteral (including intravenous), intraarterial, subcutaneous, oral, and nasal administration. Particular routes of parenteral administration include, but are not limited to, intramuscular, subcutaneous, intraperitoneal, intracerebral, intraventricular, intracerebroventricular, intrathecal, intracisternal, intraspinal and/or peri-spinal routes of administration.

In some embodiments of the invention, the formulation comprises an in situ polymerizable gel, as described, for example, in US 2002/0022676; Anseth et al. (2002) and Wang et al. (2003).

In some embodiments, the polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883. In the process described in U.S. Pat. No. 4,352,883, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. Each phosphorous atom is covalently bonded to two side chains.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)]phosphazene (PCPP) can be synthesized, which is cross-linked with dissolved multivalent cations in aqueous media at room temperature or below to form hydrogel matrices.

Biodegradable polyphosphazenes have at least two differing types of side chains, acidic side groups capable of forming salt bridges with multivalent cations, and side groups that hydrolyze under in vivo conditions, e.g., imidazole groups, amino acid esters, glycerol and glucosyl.

Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in the scientific paper of Allcock et al. (1977). Methods of synthesis of the hydrogel materials, as well as methods for preparing such hydrogels, are known in the art.

The MPC-derived supernatant or soluble factors, MPCs or progeny thereof may be administered with other beneficial drugs or biological molecules (growth factors, trophic factors). When administered with other agents, they may be administered together in a single pharmaceutical composition, or in separate pharmaceutical compositions, simultaneously or sequentially with the other agents (either before or after administration of the other agents). Bioactive factors which may be co-administered include anti-apoptotic agents (e.g., EPO, EPO mimetibody, TPO, IGF-I and IGF-II, HGF, caspase inhibitors); anti-inflammatory agents (e.g., p38 MAPK inhibitors, TGF-beta inhibitors, statins, IL-6 and IL-1 inhibitors, PEMIROLAST, TRANILAST, REMICADE, SIROLIMUS, and NSAIDs (non-steroidal anti-inflammatory drugs; e.g., TEPDXALIN, TOLMETIN, SUPROFEN); immunosupressive/immunomodulatory agents (e.g., calcineurin inhibitors, such as cyclosporine, tacrolimus; mTOR inhibitors (e.g., SIROLIMUS, EVEROLIMUS); anti-proliferatives (e.g., azathioprine, mycophenolate mofetil); corticosteroids (e.g., prednisolone, hydrocortisone); antibodies such as monoclonal anti-IL-2Ralpha receptor antibodies (e.g., basiliximab, daclizumab), polyclonal anti-T-cell antibodies (e.g., anti-thymocyte globulin (ATG); anti-lymphocyte globulin (ALG); monoclonal anti-T cell antibody OKT3)); anti-thrombogenic agents (e.g., heparin, heparin derivatives, urokinase, PPack (dextrophenylalanine proline arginine chloromethylketone), antithrombin compounds, platelet receptor antagonists, anti-thrombin antibodies, anti-platelet receptor antibodies, aspirin, dipyridamole, protamine, hirudin, prostaglandin inhibitors, and platelet inhibitors); and anti-oxidants (e.g., probucol, vitamin A, ascorbic acid, tocopherol, coenzyme Q-10, glutathione, L-cysteine, N-acetylcysteine) as well as local anesthetics. As another example, the MPC-derived supernatant or soluble factors, MPCs or progeny thereof may be co-administered with scar inhibitory factor as described in U.S. Pat. No. 5,827,735.

When treating and/or preventing a disease arising from degradation and/or inflammation of connective tissue it is preferred that the supernatant, soluble factors or cells are administered with chondroprotective agents. Examples include, but are not limited to, pentosan polysulfate (SP54 and Cartrophen), glycosaminoglycan polysufate ester (Arteparon), glyciamino-glycan-peptide complex (Rumalon) and hyaluronic acid (Hyalgan). Further examples are described by Verbruggen (2005) and Richette and Bardin (2004). In a preferred embodiment, the chondroprotective agent is hyaluronic acid.

Fibrin Glue

Fibrin glues are a class of surgical sealants which have been used in various clinical settings. As the skilled address would be aware, numerous sealants are useful for the methods defined herein. However, a preferred embodiment of the invention relates to the use of fibrin glues.

When used herein the term "fibrin glue" refers to the insoluble matrix formed by the cross-linking of fibrin polymers in the presence of calcium ions. The fibrin glue may be formed from fibrinogen, or a derivative or metabolite thereof, fibrin (soluble monomers or polymers) and/or complexes thereof derived from biological tissue or fluid which forms a fibrin matrix. Alternatively, the fibrin glue may be formed from fibrinogen, or a derivative or metabolite thereof, or fibrin, produced by recombinant DNA technology.

The fibrin glue may also be formed by the interaction of fibrinogen and a catalyst of fibrin glue formation (such as thrombin and/or Factor XIII). As will be appreciated by those skilled in the art, fibrinogen is proteolytically cleaved in the presence of a catalyst (such as thrombin) and converted to a fibrin monomer. The fibrin monomers may then form polymers which may cross-link to form a fibrin glue matrix. The cross-linking of fibrin polymers may be enhanced by the presence of a catalyst such as Factor XIII. The catalyst of fibrin glue formation may be derived from blood plasma, cryoprecipitate or other plasma fractions containing fibrinogen or thrombin. Alternatively, the catalyst may be produced by recombinant DNA technology.

The rate at which the clot forms is dependent upon the concentration of thrombin mixed with fibrinogen. Being an enzyme dependent reaction, the higher the temperature (up to 37° C.) the faster the clot formation rate. The tensile strength of the clot is dependent upon the concentration of fibrinogen used.

Use of fibrin glue and methods for its preparation and use are described by Hirsh et al. in U.S. Pat. No. 5,643,192. Hirsh discloses the extraction of fibrinogen and thrombin components from a single donor, and the combination of only these components for use as a fibrin glue. Marx, U.S. Pat. No. 5,651,982, describes another preparation and method of use for fibrin glue. Marx provides a fibrin glue with liposomes for use as a topical sealant in mammals. The preparation and use of a topical fibrinogen complex (TFC) for wound healing is known in the field. International Patent Publication No. WO96/17633, of The American Red Cross, discusses TFC preparations containing fibrinogen, thrombin, and calcium chloride.

Several publications describe the use of fibrin glue for the delivery of therapeutic agents. For example, U.S. Pat. No. 4,983,393 discloses a composition for use as an intra-vaginal insert comprising agarose, agar, saline solution glycosaminoglycans, collagen, fibrin and an enzyme. Further, U.S. Pat. No. 3,089,815 discloses an injectable pharmaceutical preparation composed of fibrinogen and thrombin and U.S. Pat. No. 6,468,527 discloses a fibrin glue which facilitates the delivery of various biological and non-biological agents to specific sites within the body.

Production of Genetically Modified Cells

In one embodiment, the cells used in the methods of the invention, including for the production of supernatant or soluble factors, are genetically modified. Preferably, the cells are genetically modified to produce a heterologous protein. Typically, the cells will be genetically modified such that the heterologous protein is secreted from the cells. However, in an embodiment the cells can be modified to express a functional non-protein encoding polynucleotide such as dsRNA (typically for RNA silencing), an antisense oligonucleotide or a catalytic nucleic acid (such as a ribozyme or DNAzyme).

Genetically modified cells may be cultured in the presence of at least one cytokine in an amount sufficient to support growth of the modified cells. The genetically modified cells thus obtained may be used immediately (e.g., in transplant), cultured and expanded in vitro, or stored for later uses. The modified cells may be stored by methods well known in the art, e.g., frozen in liquid nitrogen.

Genetic modification as used herein encompasses any genetic modification method which involves introduction of an exogenous or foreign polynucleotide into a cell described herein or modification of an endogenous gene within the cell. Genetic modification includes but is not limited to transduction (viral mediated transfer of host DNA from a host or donor to a recipient, either in vitro or in vivo), transfection (transformation of cells with isolated viral DNA genomes), liposome mediated transfer, electroporation, calcium phosphate transfection or coprecipitation and others. Methods of transduction include direct co-culture of cells with producer cells (Bregni et al., 1992) or culturing with viral supernatant alone with or without appropriate growth factors and polycations.

An exogenous polynucleotide is preferably introduced to the cell in a vector. The vector preferably includes the necessary elements for the transcription and translation of the inserted coding sequence. Methods used to construct such vectors are well known in the art. For example, techniques for constructing suitable expression vectors are described in detail in Sambrook et al., Molecular Cloning: A Laboratory Manual, Cold Spring Harbor Press, N.Y. (3rd Ed., 2000); and Ausubel et al., Current Protocols in Molecular Biology, John Wiley & Sons, Inc., New York (1999).

Vectors may include, but are not limited to, viral vectors, such as retroviruses, adenoviruses, adeno-associated viruses, and herpes simplex viruses; cosmids; plasmid vectors; synthetic vectors; and other recombination vehicles typically used in the art. Vectors containing both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). Specific examples include, pSG, pSV2CAT, pXtl from Stratagene; and pMSG, pSVL, pBPV and pSVK3 from Pharmacia.

Preferred vectors include retroviral vectors (see, Coffin et al., "Retroviruses", Chapter 9 pp; 437-473, Cold Springs Harbor Laboratory Press, 1997). Vectors useful in the invention can be produced recombinantly by procedures well known in the art. For example, WO94/29438, WO97/21824 and WO97/21825 describe the construction of retroviral packaging plasmids and packing cell lines. Exemplary vectors include the pCMV mammalian expression vectors, such as pCMV6b and pCMV6c (Chiron Corp.), pSFFV-Neo, and pBluescript-Sk+. Non-limiting examples of useful retroviral vectors are those derived from murine, avian or primate retroviruses. Common retroviral vectors include those based on the Moloney murine leukemia virus (MoMLV-vector). Other MoMLV derived vectors include, Lmily, LINGFER, MINGFR and MINT. Additional vectors include those based on Gibbon ape leukemia virus (GALV) and Moloney murine sarcoma virus (MOMSV) and spleen focus forming virus (SFFV). Vectors derived from the murine stem cell virus (MESV) include MESV-MiLy. Retroviral vectors also include vectors based on lentiviruses, and non-limiting examples include vectors based on human immunodeficiency virus (HIV-1 and HIV-2).

In producing retroviral vector constructs, the viral gag, pol and env sequences can be removed from the virus, creating room for insertion of foreign DNA sequences. Genes encoded by foreign DNA are usually expressed under the control a strong viral promoter in the long terminal repeat (LTR). Selection of appropriate control regulatory sequences is dependent on the host cell used and selection is within the skill of one in the art. Numerous promoters are known in addition to the promoter of the LTR. Non-limiting examples include the phage lambda PL promoter, the human cytomegalovirus (CMV) immediate early promoter; the U3 region promoter of the Moloney Murine Sarcoma Virus (MMSV), Rous Sacroma Virus (RSV), or Spleen Focus Forming Virus (SFFV); Granzyme A promoter; and the Granzyme B promoter. Additionally inducible or multiple control elements may be used. The selection of a suitable promoter will be apparent to those skilled in the art.

Such a construct can be packed into viral particles efficiently if the gag, pol and env functions are provided in trans by a packing cell line. Therefore, when the vector construct is introduced into the packaging cell, the gag-pol and env proteins produced by the cell, assemble with the vector RNA to produce infectious virons that are secreted into the culture medium. The virus thus produced can infect and integrate into the DNA of the target cell, but does not produce infectious viral particles since it is lacking essential packaging sequences. Most of the packing cell lines currently in use have been transfected with separate plasmids, each containing one of the necessary coding sequences, so that multiple recombination events are necessary before a replication competent virus can be produced. Alternatively the packaging cell line harbours a provirus. The provirus has been crippled so that although it may produce all the proteins required to assemble infectious viruses, its own RNA cannot be packaged into virus. RNA produced from the recombinant virus is packaged instead. Therefore, the virus stock released from the packaging cells contains only recombinant virus. Non-limiting examples of retroviral packaging lines include PA12, PA317, PE501, PG13, PSI.CRIP, RDI 14, GP7C-tTA-G10, ProPak-A (PPA-6), and PT67.

Other suitable vectors include adenoviral vectors (see, WO 95/27071) and adeno-associated viral vectors. These vectors are all well known in the art, e.g., as described in Stem Cell Biology and Gene Therapy, eds. Quesenberry et al., John Wiley & Sons, 1998; and U.S. Pat. Nos. 5,693,531 and 5,691,176. The use of adenovirus-derived vectors may be advantageous under certain situation because they are not capable of infecting non-dividing cells. Unlike retroviral DNA, the adenoviral DNA is not integrated into the genome of the target cell. Further, the capacity to carry foreign DNA is much larger in adenoviral vectors than retroviral vectors. The adeno-associated viral vectors are another useful delivery system. The DNA of this virus may be integrated into non-dividing cells, and a number of polynucleotides have been successful introduced into different cell types using adeno-associated viral vectors.

In some embodiments, the construct or vector will include two or more heterologous polynucleotide sequences. Preferably the additional nucleic acid sequence is a polynucleotide which encodes a selective marker, a structural gene, a therapeutic gene, or a cytokine/chemokine gene.

A selective marker may be included in the construct or vector for the purposes of monitoring successful genetic modification and for selection of cells into which DNA has been integrated. Non-limiting examples include drug resistance markers, such as G148 or hygromycin. Additionally negative selection may be used, for example wherein the marker is the HSV-tk gene. This gene will make the cells sensitive to agents such as acyclovir and gancyclovir. The NeoR (neomycin/G148 resistance) gene is commonly used but any convenient marker gene may be used whose gene sequences are not already present in the target cell can be used. Further non-limiting examples include low-affinity Nerve Growth Factor (NGFR), enhanced fluorescent green protein (EFGP), dihydrofolate reductase gene (DHFR) the bacterial hisD gene, murine CD24 (HSA), murine CD8a(lyt), bacterial genes which confer resistance to puromycin or phleomycin, and β-glactosidase.

The additional polynucleotide sequence(s) may be introduced into the cell on the same vector or may be introduced into the host cells on a second vector. In a preferred embodiment, a selective marker will be included on the same vector as the polynucleotide.

The present invention also encompasses genetically modifying the promoter region of an endogenous gene such that expression of the endogenous gene is up-regulated resulting in the increased production of the encoded protein compared to a wild type cell.

EXAMPLES

Example 1

Expansion of Immunoselected MPCs and Collection of Supernatant

Bone marrow (BM) is harvested from sheep less than 2 years old. Briefly, 40 ml of BM is aspirated from the anterior iliac crest into lithium-heparin anticoagulant-containing tubes. BMMNC are prepared by density gradient separation using Lymphoprep™ (Nycomed Pharma, Oslo, Norway) as previously described (Zannettino et al., 1998). Following centrifugation at 400×g for 30 minutes at 4° C., the buffy layer is removed with a transfer pipette and washed three times in "HHF", composed of Hank's balanced salt solution (HBSS; Life Technologies, Gaithersburg, Md.), containing 5% fetal calf serum (FCS, CSL Limited, Victoria, Australia).

TNAP+ were subsequently isolated by magnetic activated cell sorting as previously described (Gronthos et al., 2003; Gronthos et al., 1995). Briefly, approximately $1-3 \times 10^8$ BMMNC are incubated in blocking buffer, consisting of 10% (v/v) normal rabbit serum in HHF for 20 minutes on ice. The cells are incubated with 200 µl of a 10 µg/ml solution of STRO-3 mAb in blocking buffer for 1 hour on ice. The cells are subsequently washed twice in HHF by centrifugation at 400×g. A 1/50 dilution of goat anti-mouse γ-biotin (Southern Biotechnology Associates, Birmingham, UK) in HHF buffer is added and the cells incubated for 1 hour on ice. Cells are washed twice in MACS buffer ($Ca^{2+}$- and $Mn^{2+}$-free PBS supplemented with 1% BSA, 5 mM EDTA and 0.01% sodium azide) as above and resuspended in a final volume of 0.9 ml MACS buffer.

One hundred µl streptavidin microbeads (Miltenyi Biotec; Bergisch Gladbach, Germany) are added to the cell suspension and incubated on ice for 15 minutes. The cell suspension is washed twice and resuspended in 0.5 ml of MACS buffer and subsequently loaded onto a mini MACS column (MS Columns, Miltenyi Biotec), and washed three times with 0.5 ml MACS buffer to retrieve the cells which did not bind the STRO-3 mAb (deposited on 19 Dec. 2005 with American Type Culture Collection (ATCC) under accession number PTA-7282—see WO/2006/108229). After addition of a further 1 ml MACS buffer, the column is removed from the magnet and the TNAP-positive cells are isolated by positive pressure. An aliquot of cells from each fraction can be stained with streptavidin-FITC and the purity assessed by flow cytometry.

Primary cultures are established from the MACS isolated TNAP+ cells by plating in α-MEM supplemented with 20% fetal calf serum, 2 mM L-glutamine and 100 µm L-ascorbate-2-phosphate as previously described (Gronthos et al., 1995).

Cells were cultured up to passage 5 at which point the conditioned medium (supernatant) may be collected.

Example 2

Studies on the Dose Dependent Intra-Articular Effects of Allogeneic Immunoselected Mesenchymal Precursors Cells (MPC) on Cartilage Integrity in a Model of Early OA Induced by Bilateral Total Medial Meniscectomy in Adult Castrated Male Sheep (Wethers)

The knee joint menisci, or semi-lunar cartilages, are important weight bearing structures that also serve to improve articular cartilage lubrication and provide lateral stabilization during joint articulation. Surgical removal of a torn or degenerate meniscus, i.e., meniscectomy, is a common orthopaedic procedure but is known to be associated with an increased risk of osteoarthritis (OA) in later years (Englund, 2004). Mechanical entrapment of the joint synovium in the space previously occupied by the surgically excised meniscus is known to lead to the partial regeneration of a meniscus replica (Moon et al., 1984). However, the results of experimental meniscectomy studies in dogs indicate that these replacement structures consisted essentially of fibrous tissue with far inferior biomechanical properties to the original menisci (Ghosh et al., 1983). Furthermore, the extent of OA development in the joints of these experimental animals 6 months post-meniscectomy was relatively severe, confirming the limited functional protection offered by the regrown structures on articular cartilage (Ghosh et al. 1983a). Large and small animal models of OA have permitted longitudinal evaluation of spatial and temporal changes in joint tissues that occur during the development of this disease which is difficult obtain using human patients (Smith and Ghosh, 2001). In merino sheep, lateral or medial meniscectomy has been shown to reliably reproduce biochemical, biomechanical and histopathological alterations typical of OA (Smith and Ghosh, 2001). The ovine OA model has also been extensively used to investigate the outcomes of various modalities of post-operative treatments (Ghosh, 1991; Smith and Ghosh, 2001) but to date has not been employed to evaluate meniscal regrowth and the progression of OA and how these events might be influenced by intra-articular mesenchymal precursor cell (MPC) therapy.

Our previous studies had shown that Bilateral Total Medial Meniscectomy (BTM) in merino sheep resulted in pathological changes in articular cartilage (AC), subchondral bone and synovial tissues that were progressive and simulated the development of early human osteoarthritis (OA). We previously used this animal model to evaluate potential disease-modifying OA drugs.

Methods

BTM was undertaken in 36 adult Merino wethers. Two weeks post BTM, joints were randomly injected with either 2 mL high MW Hyaluronan (HA) or 2 mL allogeneic Stro-3+ MPC suspended in 2 mL HA. Four doses of MPC were studied: Group A=10 million (mil) MPC [n=6]; Group B=25 mil MPC [n=6]; Group C=100 mil MPC [n=18] and Group D=150 mil MPC [n=6]. Groups A, B and D were sacrificed 12 weeks post-BTM while Group C were sacrificed 12 [n=6], 24 [n=6] and 52 [n=6] weeks post-BTM.

At necropsy, both medial compartments of BTM joints were scored by 2 blinded observers for AC lesions and osteophytes (OP) using a 0-4 scale. Synovial tissue and a 5 mm wide coronal osteochondral slice were removed from the mid-line of the femur and tibia and processed and scored for histopathological changes (Little et al., 1997) and histomorphometric analyses (Cake et al., 2003) using the methods cited.

Intact patellae from all joints were subjected to topographical biomechanical indentation studies to deterine the stiffness and phase lag of the articular cartilage (Appleyard et al., 2003).

Statistical analysis for treatment effect was undertaken using Kruskal-Wallis nonparametric analysis and for specific between group comparisons using Mann Whitney U nonparametric analysis with p<0.05 considered significant.

Statistical analysis for comparison between group means for MPC+HA injected and HA injected joints of each group was undertaken using the equal variance two tailed Student's T-Test with p<0.05 considered significant.

Statistical analysis for comparison between patella cartilages from MPC+HA injected (Treated) and HA injected joints of each group was undertaken using an independent T-Test with p<0.05 considered significant.

Results

Figure 2:
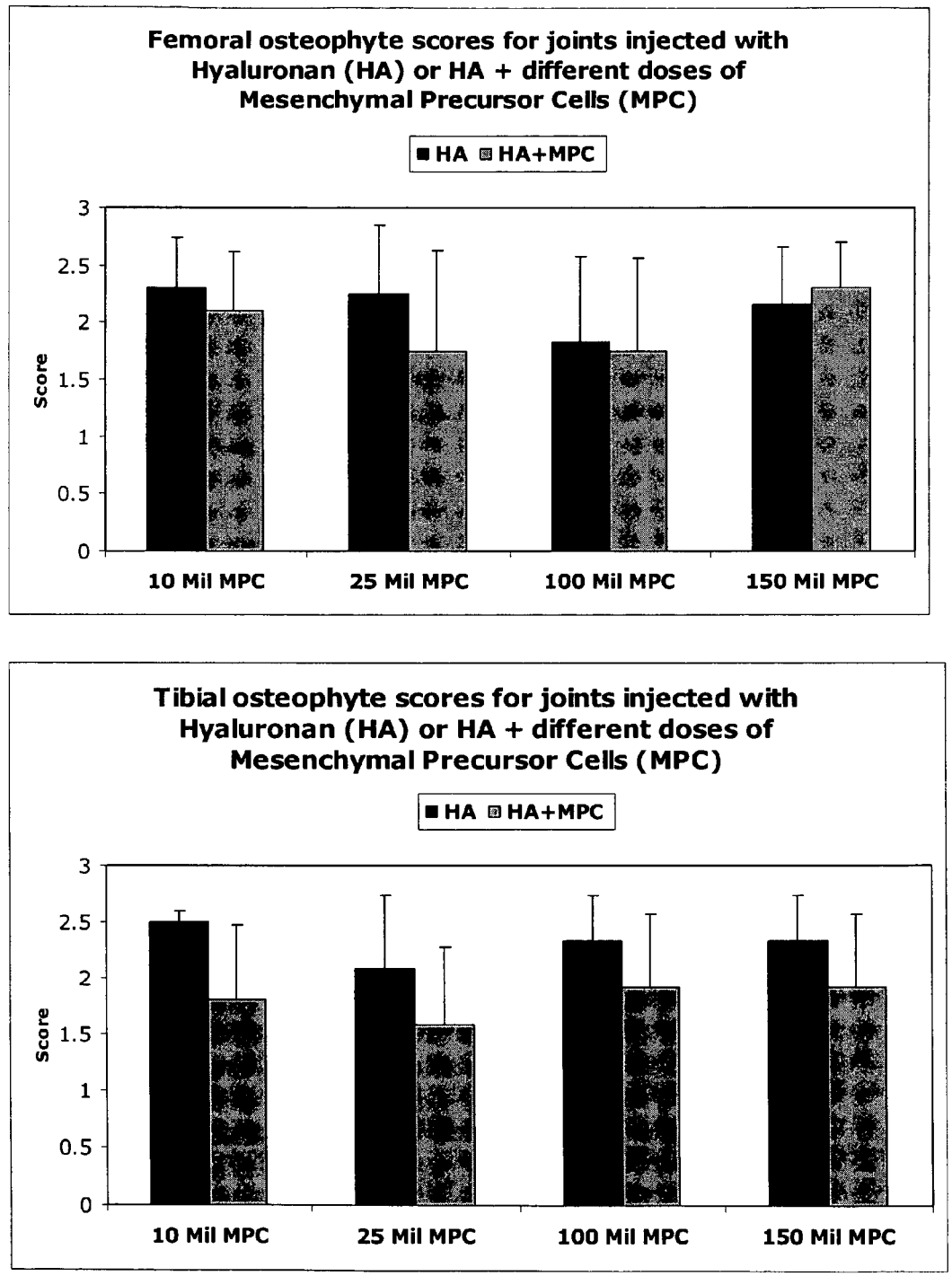
FIG. 2. Means±SD of femoral and tibial osteophyte scores 12 weeks post-meniscectomy for joints injected with Hyaluronan (HA) or HA plus different doses of Mesenchymal Precursor Cells (MPC).
Figure 2:
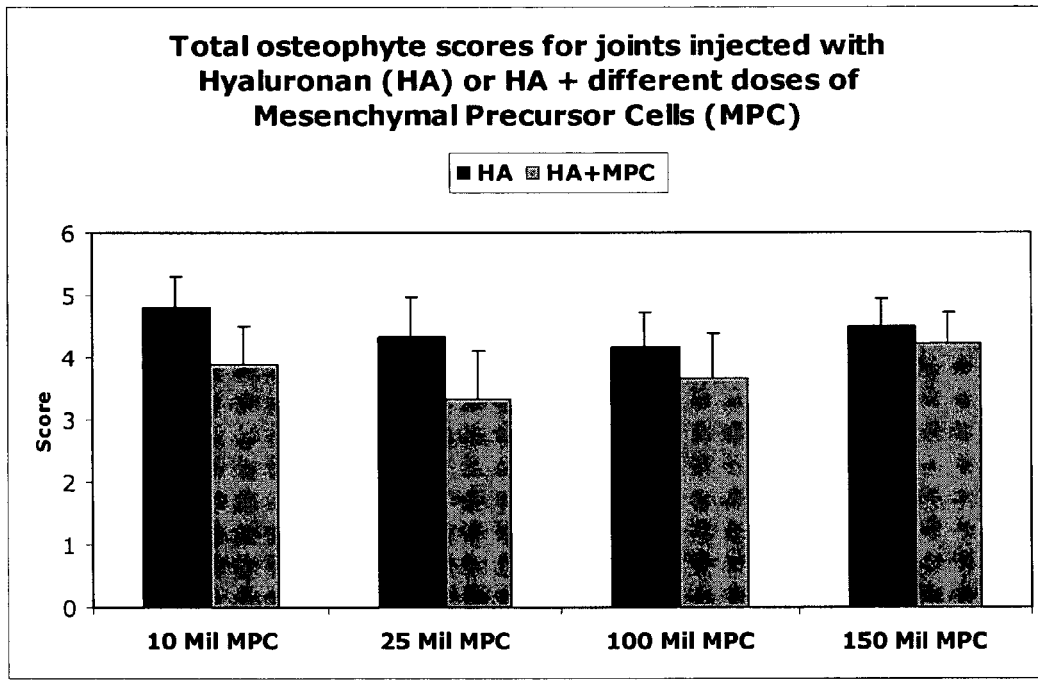
Figure 3:
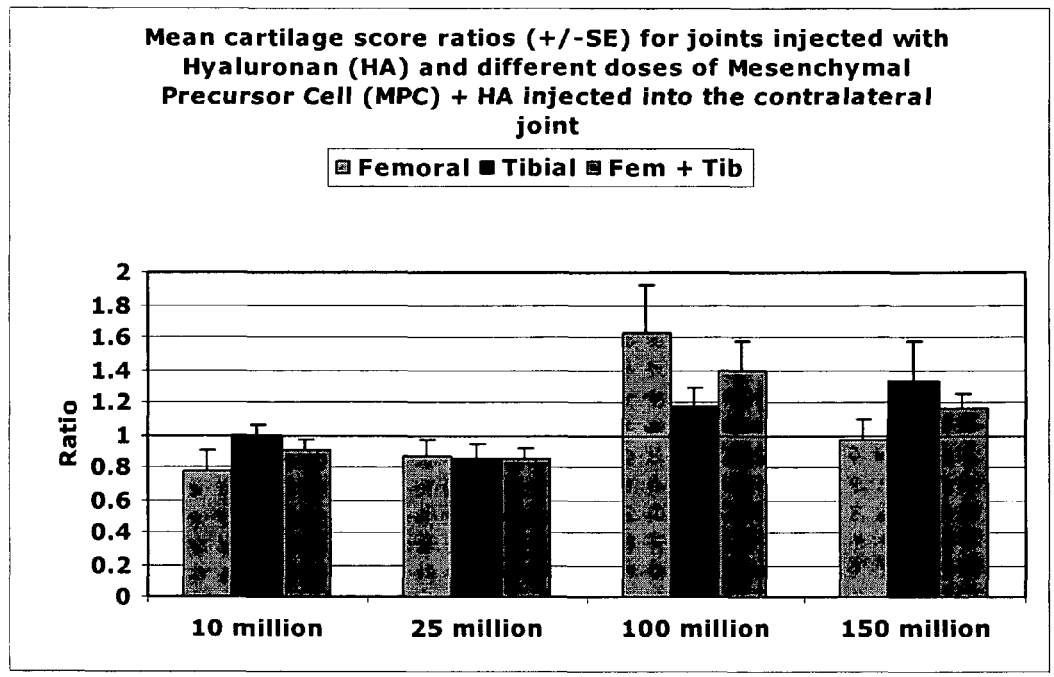
FIG. 3. Ratios [HA/(MPC+HA)] of cartilage morphology joint scores for animals injected with different doses of Mesenchymal Precursor Cells (MPC). When ratio=1 both treatments equally effective. Ratios>1 indicate MPC+HA superior to HA.
Figure 4:
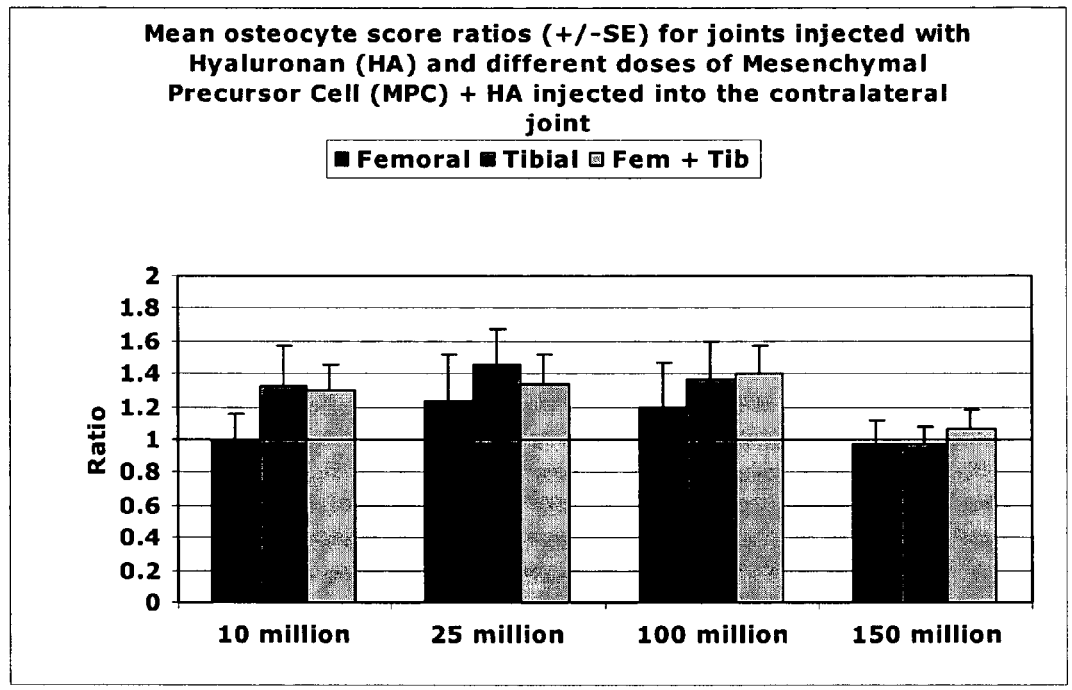
FIG. 4. Ratios [HA/(MPC+HA)] of osteophyte scores for animals injected with different doses of MPC+HA relative to HA alone. When ratio=1 both treatments equally effective. Ratios>1 indicate MPC+HA superior to HA.

Gross morphological scores 12 wks post BTM showed a dose-dependent effect of MPC on AC integrity and OP formation; 100 mil MPC emerging as the most effective chondroprotective dose relative to HA alone (FIGS. 1 and 2). Total AC score ratios (HA+MPC)/(HA) showed 100>150>25=10 while OP ratios were 100=25>10>150 mil MPC (FIGS. 3 and 4). Statistically significant (SS) lower score were observed for total femoral & tibial AC (p=0.02) while p=0.052 was observed for Group C MPC femoral cartilages compared to HA alone (FIG. 1).

Figure 5:
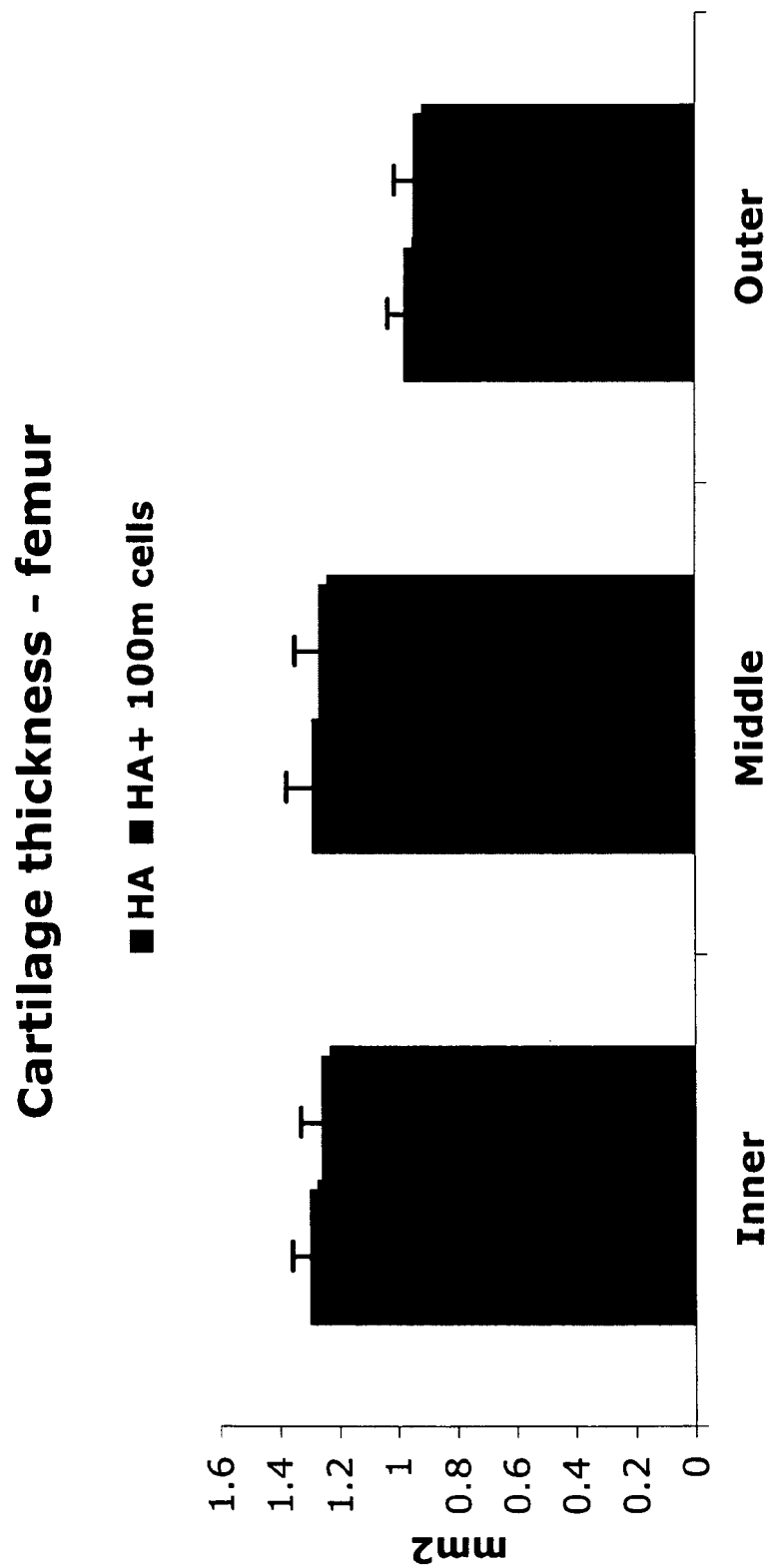
FIG. 5. Means±SE of histomorphometrically determined regional thickness scores for cartilages of joints injected with hyaluronan (HA) or 100 million MPC+HA twelve weeks post meniscectomy. Combining all tibial cartilage regions HA+100 million MPC>HA ($p<0.05$).
Figure 5:
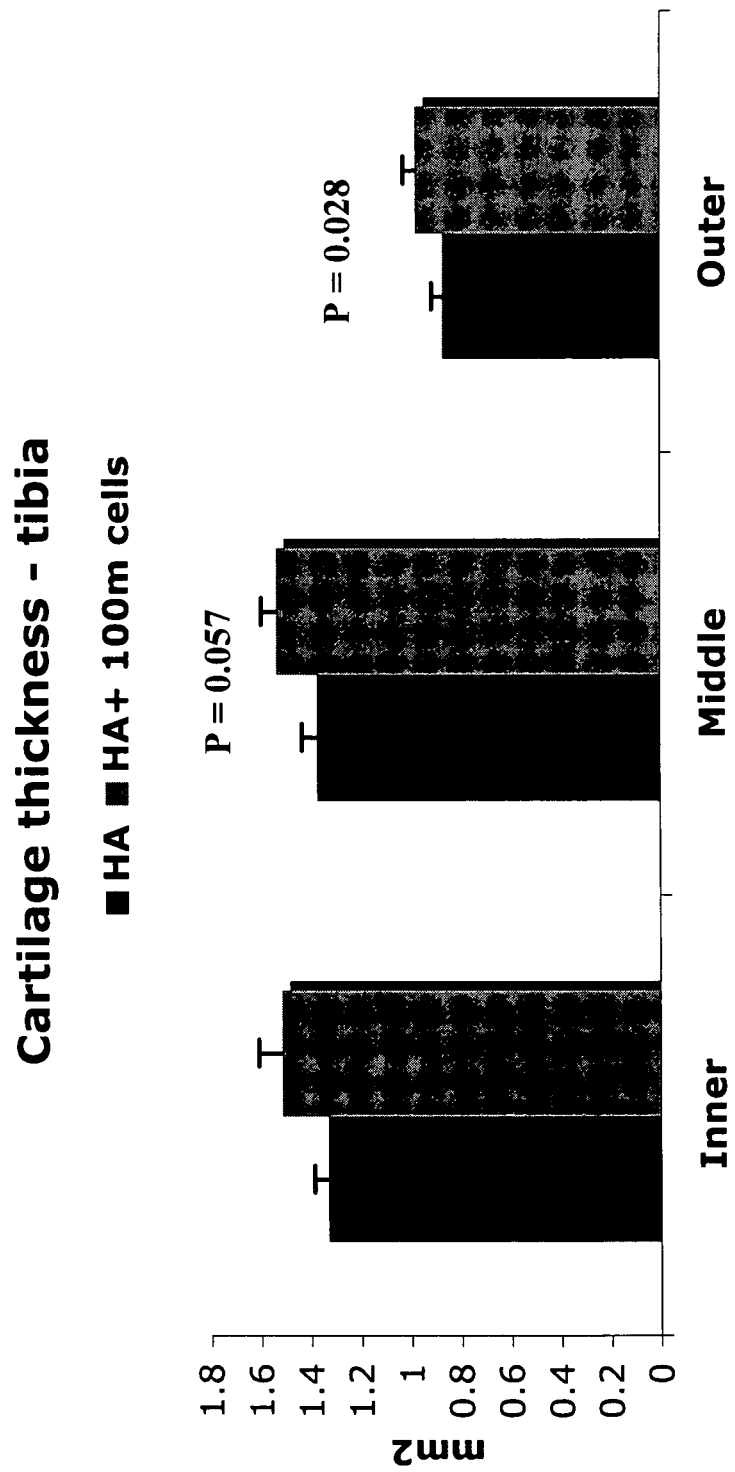
Figure 6:
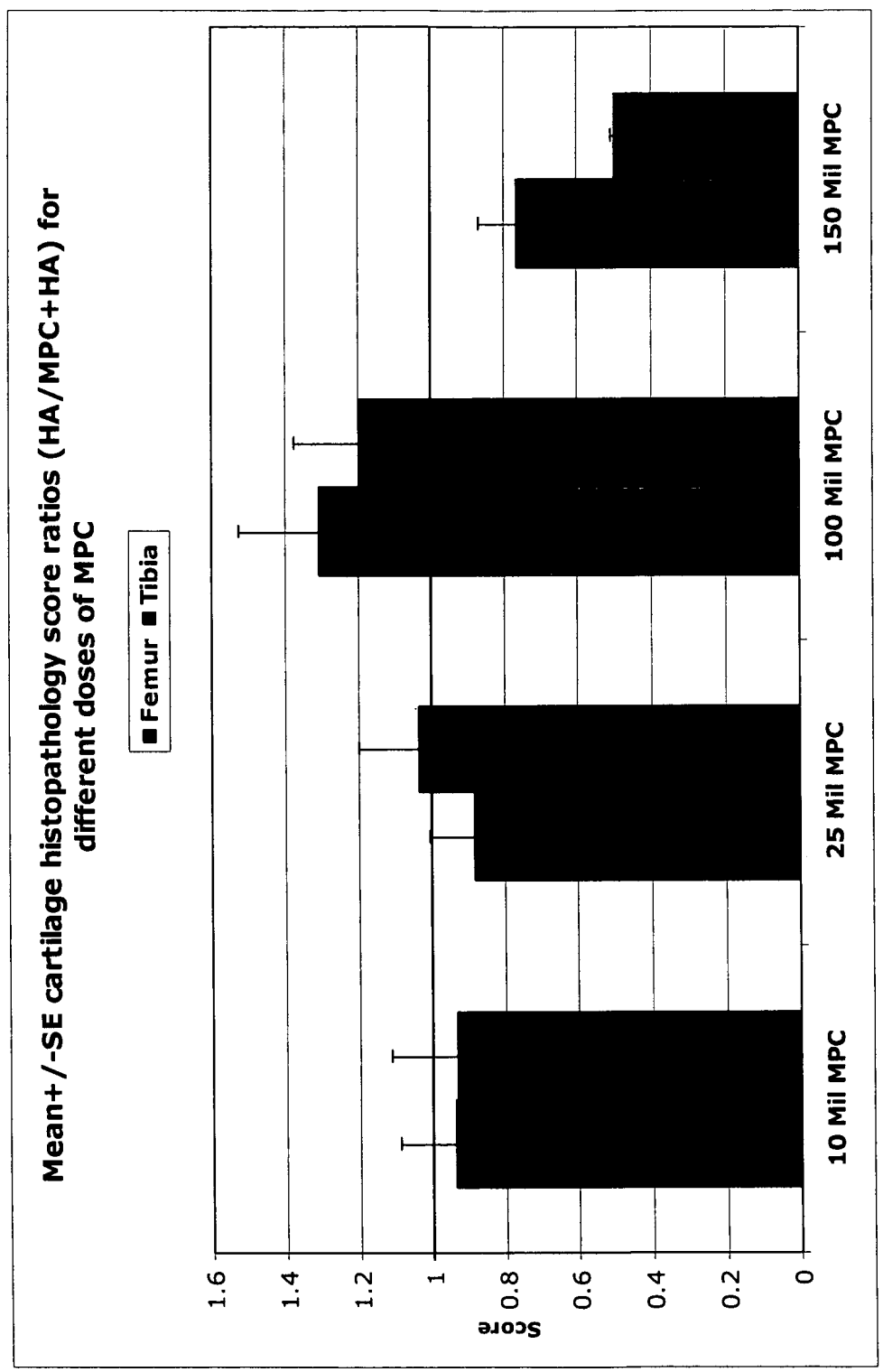
FIG. 6. Ratios [HA/(MPC+HA)] of mean±SE total Mankin Modified joint histopathology scores for animals injected with different doses of Mesenchymal Precursor Cells (MPC). When ratio=1 both treatments equally effective. Ratios>1 indicate MPC+HA superior to HA.

Histomorphometric analysis of Group C MPC+HA tibial plateau revealed that AC was thicker than the corresponding HA-AC in the middle (p=0.057) and outer regions (p=0.028); all regions (p=0.01) (FIG. 5). Mean modified Mankin scores for AC sections from Group C MPC+HA joints were less than corresponding HA sections but were not SS. In addition, when the ratios of the total Mankin scores for the HA injected and contralateral HA+MPC injected joints from each group were calculated and plotted it was clearly evident that the 100 million dose of MPC was the most efficacious (FIG. 6).

Figure 7:
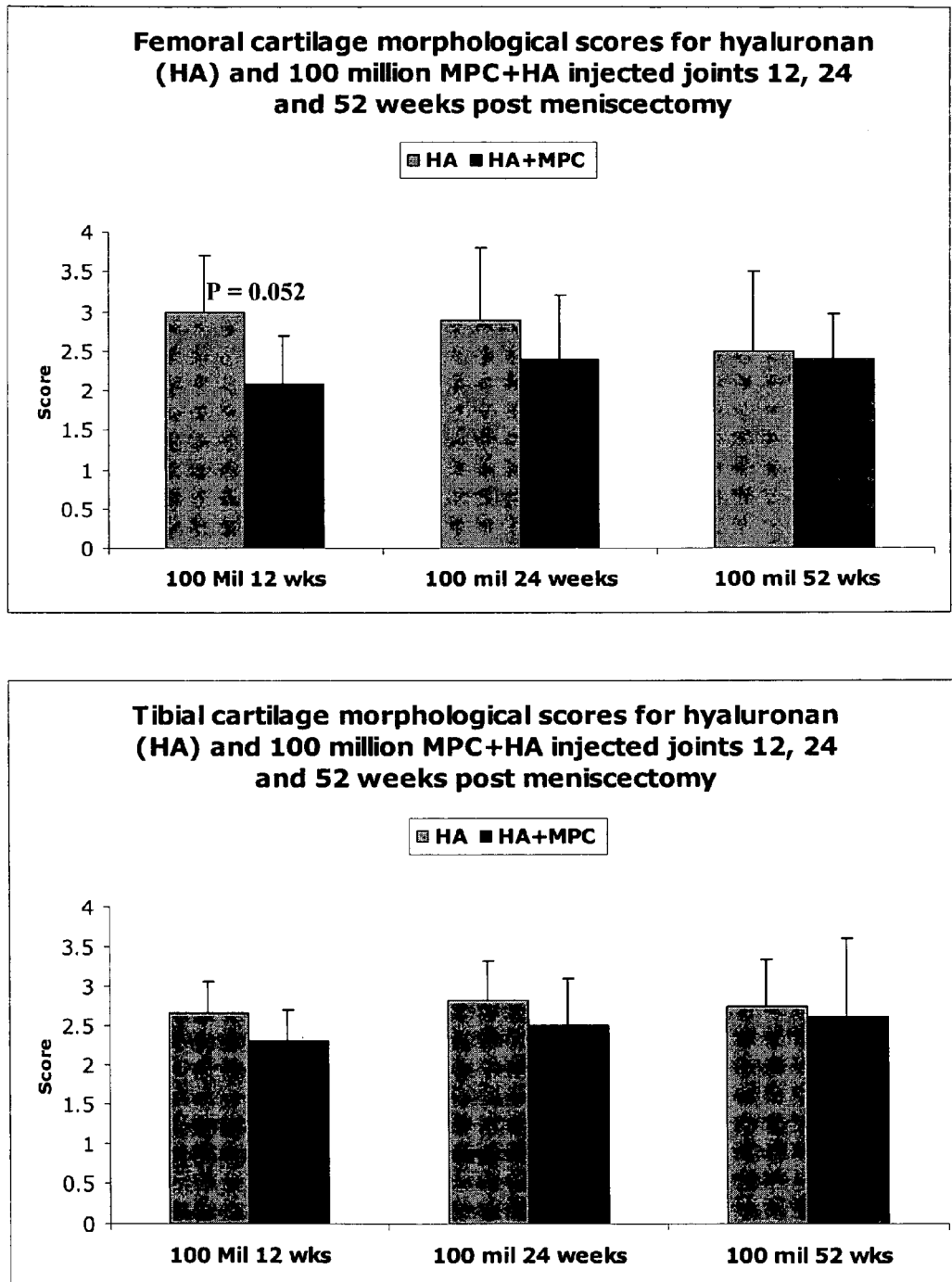
FIG. 7. Means±SD of femoral and tibial cartilage morphology scores for HA and HA+100 million MPC injected joints 12, 24 and 52 weeks post meniscectomy.
Figure 7:
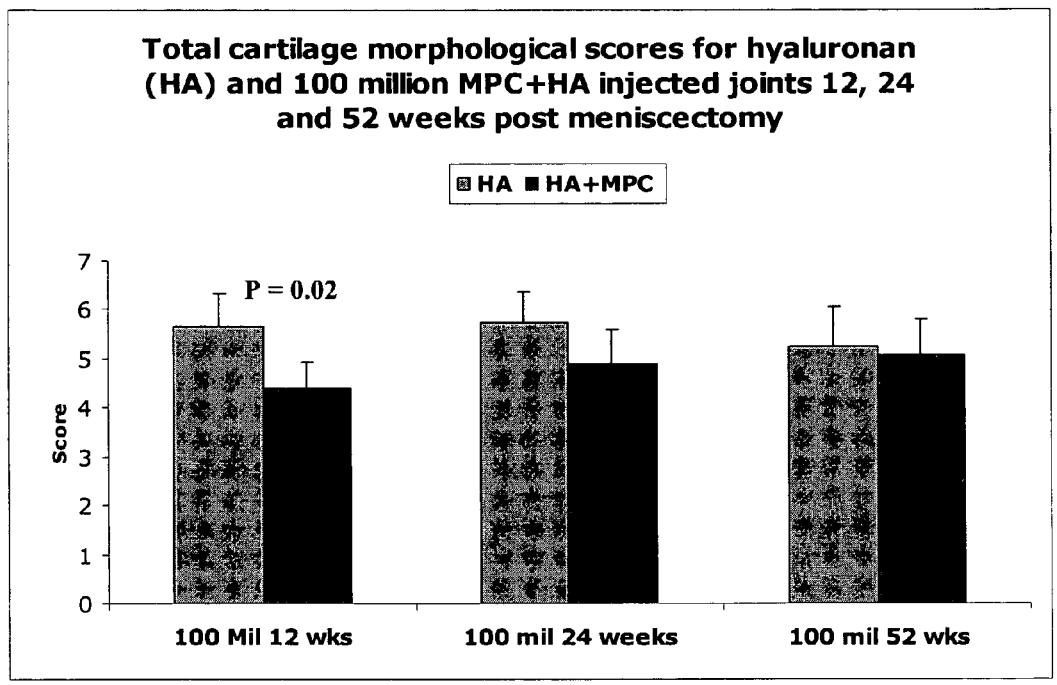
Figure 8:
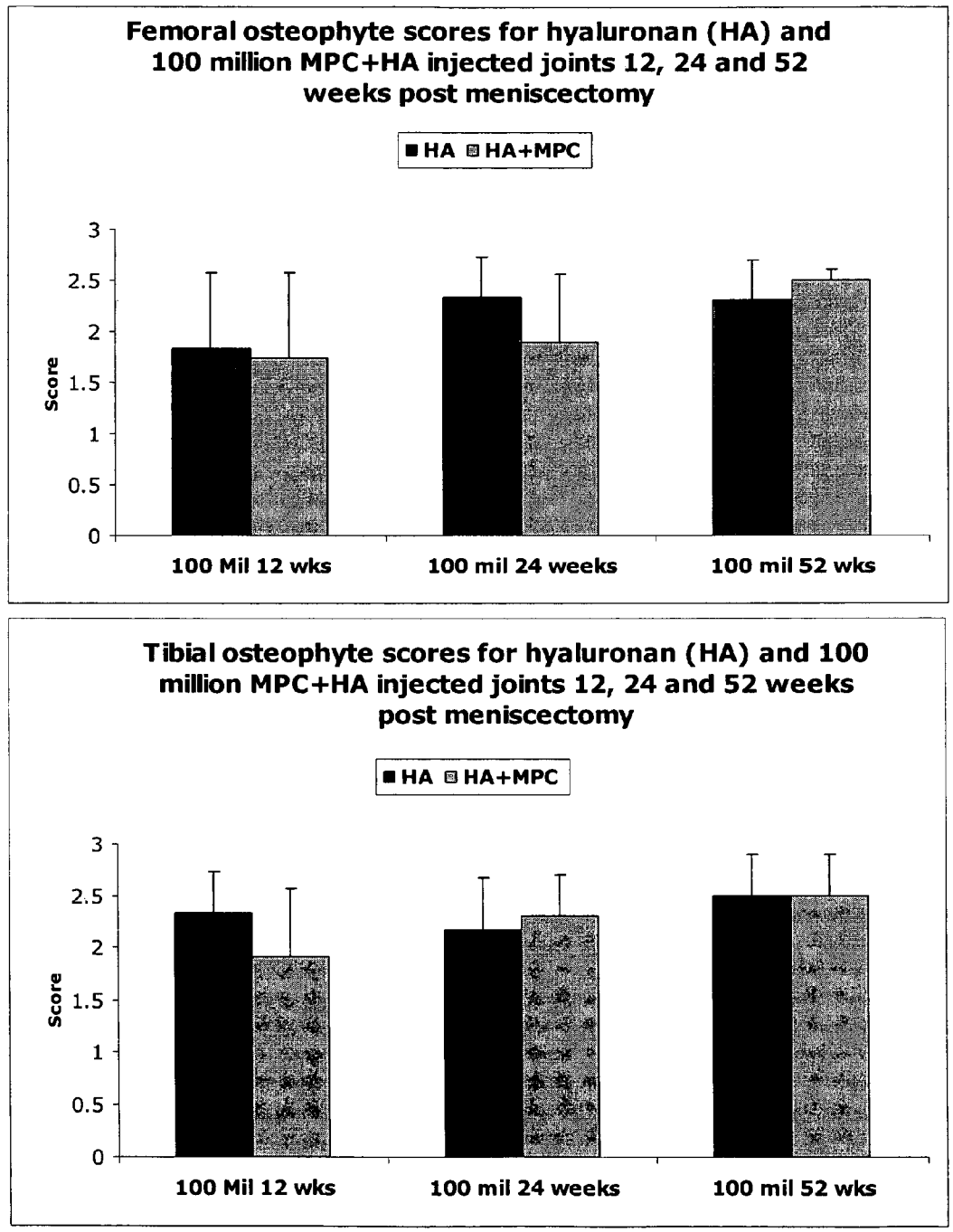
FIG. 8. Means±SD of femoral and tibial osteophyte scores for HA and HA+100 million MPC injected joints 12, 24 and 52 weeks post meniscectomy.
Figure 8:
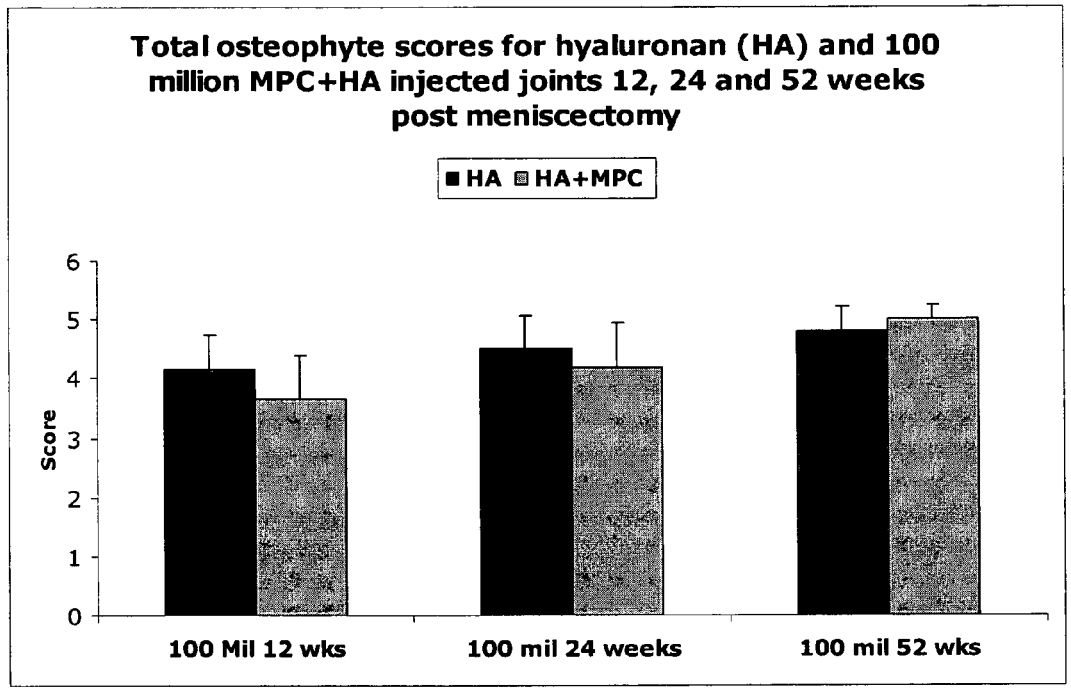
Figure 9:
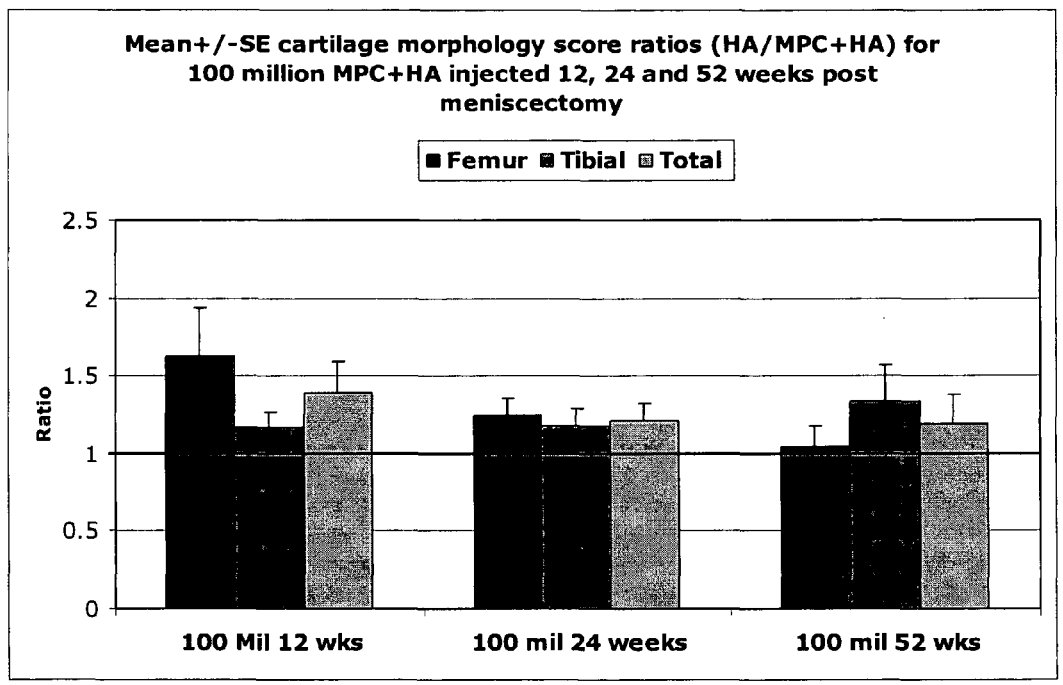
FIG. 9. Ratios [HA/(MPC+HA)] of cartilage morphology joint scores for animals injected with Mesenchymal Precursor Cells (MPC) 12, 24 and 52 weeks post meniscectomy. When ratio=1 both treatments equally effective. Ratios>1 indicate MPC+HA superior to HA.
Figure 10:
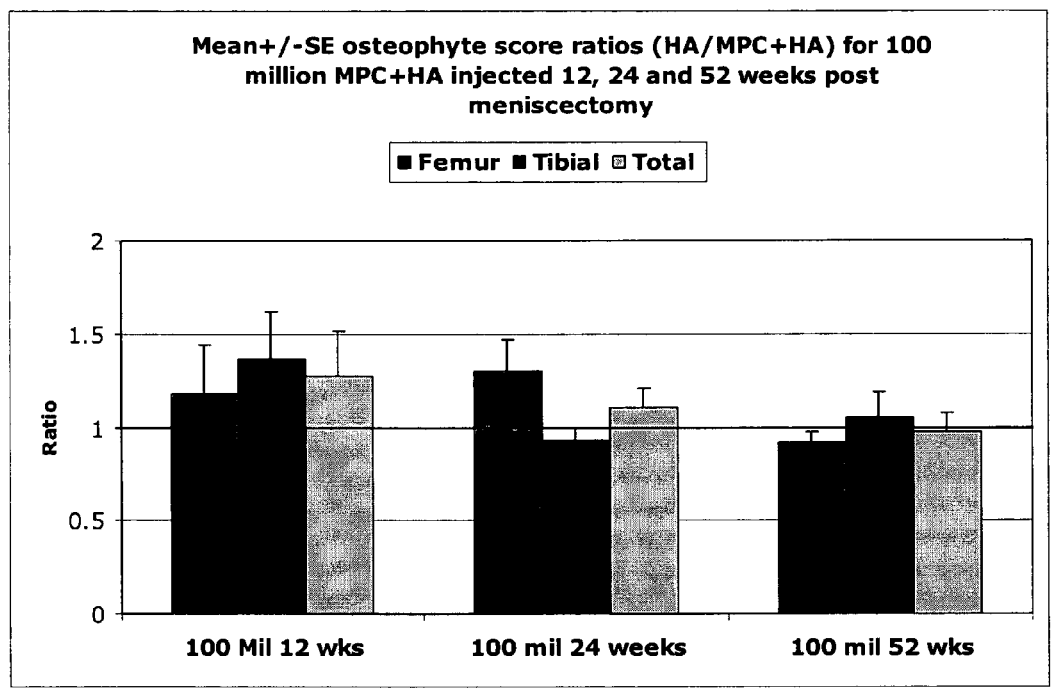
FIG. 10. Ratios [HA/(MPC+HA)] of osteophyte joint scores for animals injected with Mesenchymal Precursor Cells (MPC) 12, 24 and 52 weeks post meniscectomy. When ratio=1 both treatments equally effective. Ratios>1 indicate MPC+HA superior to HA.
Figure 11:
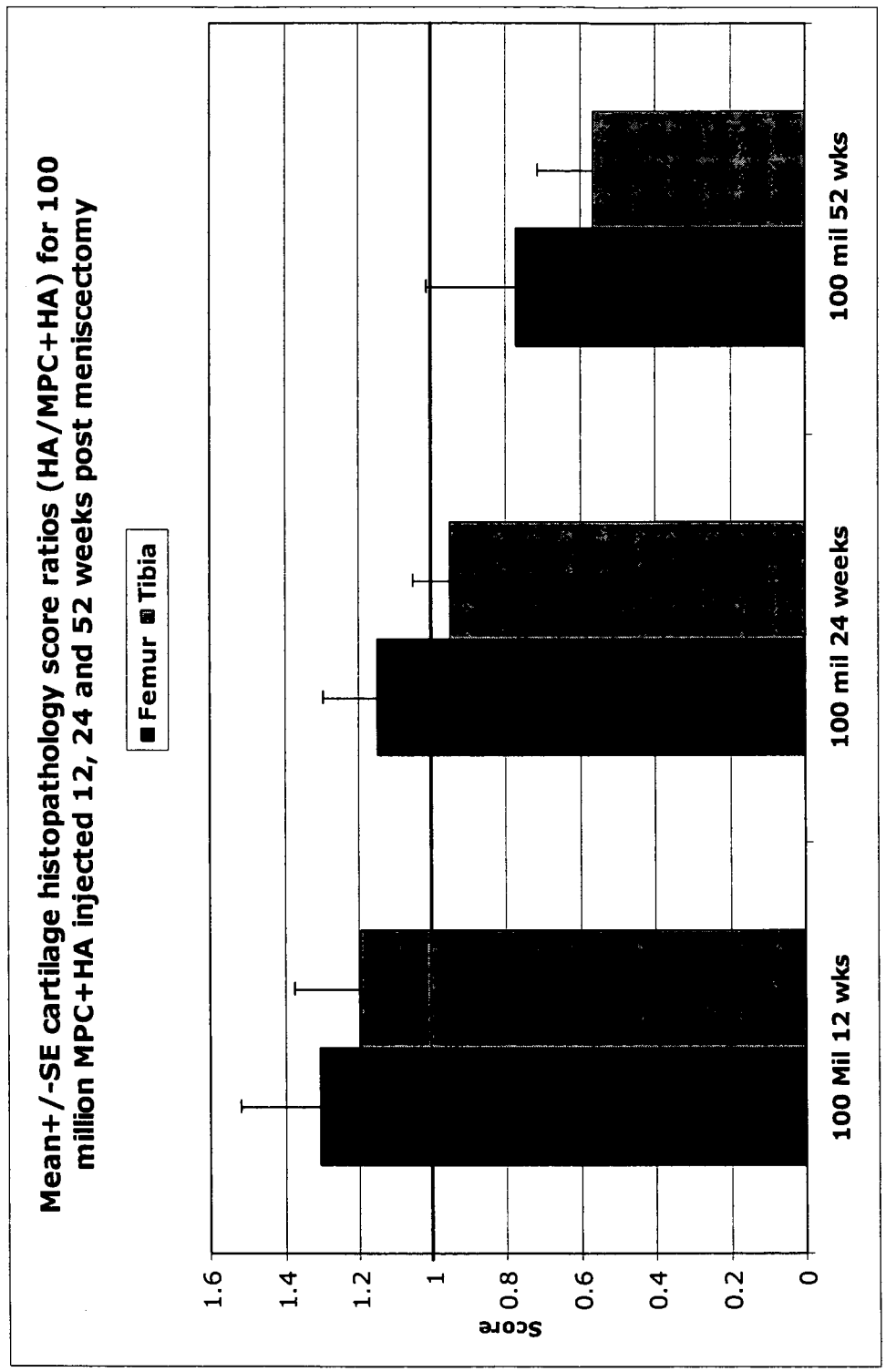
FIG. 11. Ratios [HA/(MPC+HA)] of mean±SE Modified Mankins joint cartilage histopathology scores for animals injected with Mesenchymal Precursor Cells (MPC) 12, 24 and 52 weeks post meniscectomy. When ratios=1 both treatments equally effective. Ratios>1 indicate MPC+HA superior to HA.

The question of the sustainability of the 100 million MPC dose in preserving joint cartilage integrity was addressed by studying the morphological, histological and biomechanical properties of the tissues 22 and 50 weeks post injection ie, 24 and 52 weeks post meniscectomy. As is evident from FIGS. 7 and 8 the difference between the mean values for morphological scores for HA and HA+100 million MPC diminish over this time, although there is some evidence of a therapeutic effect at 24 weeks. This view is supported by the HA/MPC+HA data which indicated a stronger effect of the cells in suppressing osteophyte scores for up to 52 weeks (FIGS. 10 and 11). On the other hand, similar plots for the Mankin histopathology scores showed that by 52 weeks the protective effects of the MPC was lost (FIG. 11).

Figure 12:
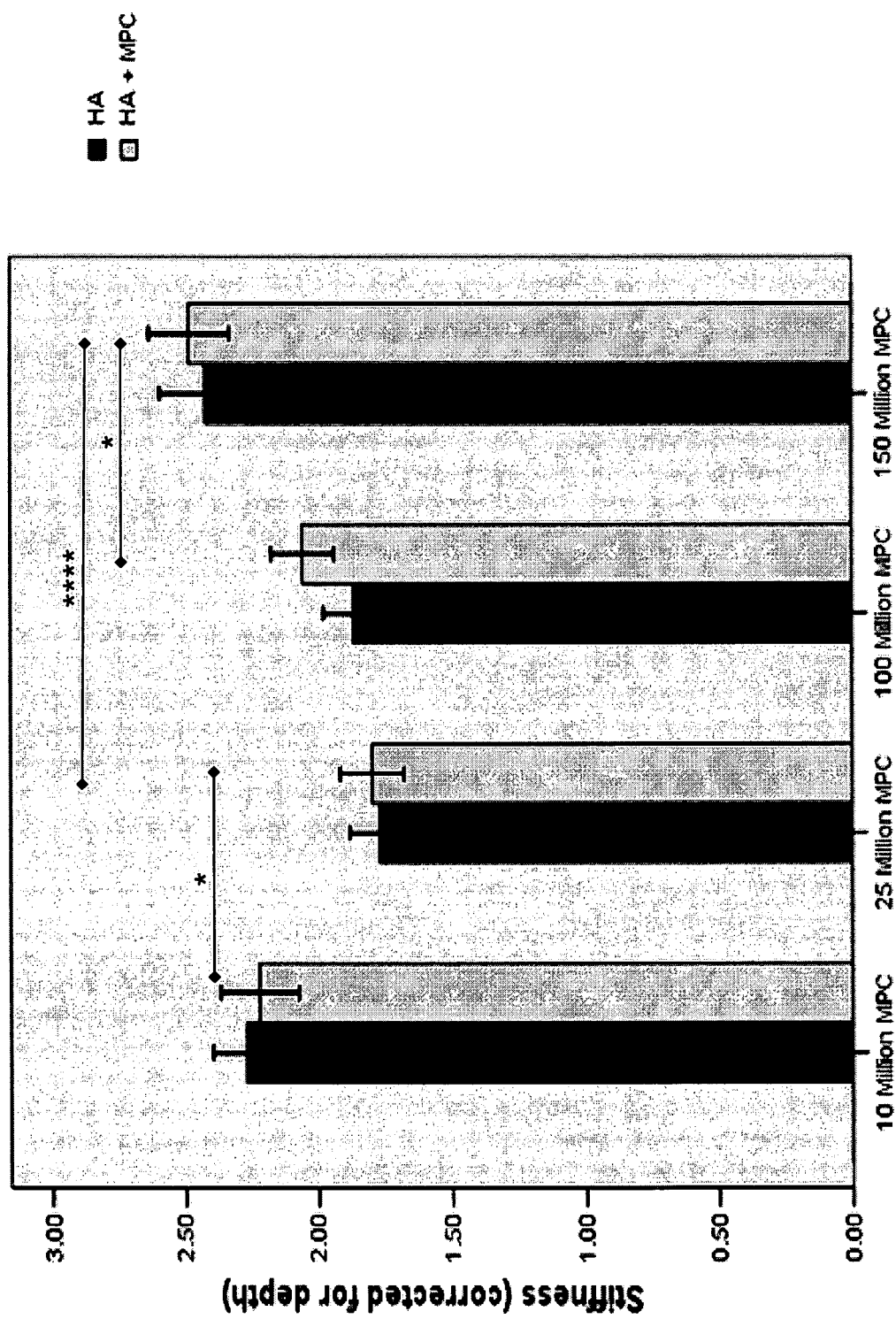
FIG. 12. Mean±/−SE of patella cartilage stiffness from joints injected with hyaluronan (HA) or HA+different doses of Mesenchymal Precursor Cells (MPC). *=p<0.05, =p<0.01, *=p<0.001, ****=p<0.0001.
Figure 13:
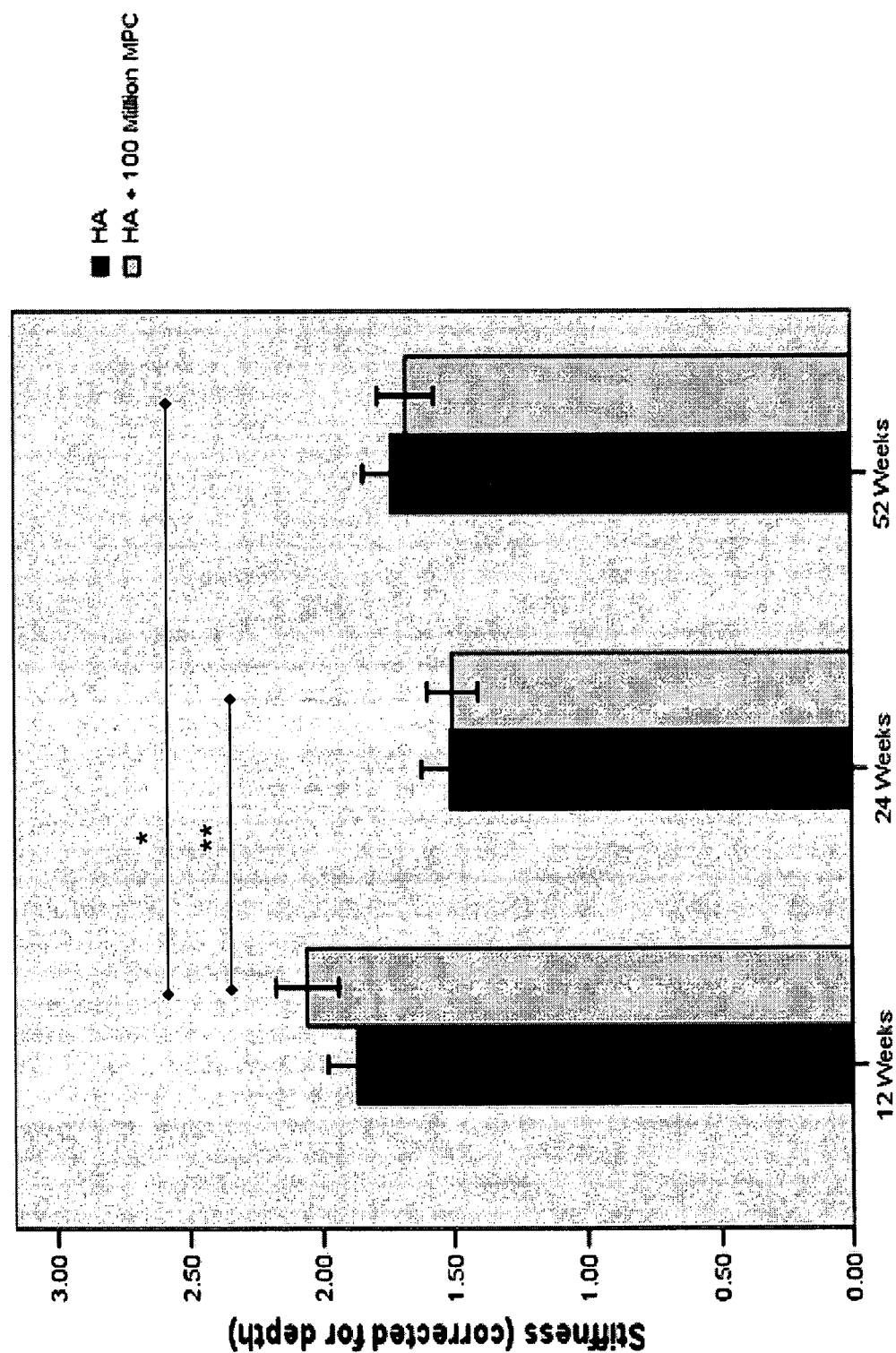
FIG. 13. Mean±/−SE of patella cartilage stiffness from joints injected with hyaluronan (HA) or 100 million Mesenchymal Precursor Cells (MPC)+HA and sacrificed 12, 24 and 52 weeks post meniscectomy. *=p<0.05, =p<0.01, *=p<0.001, ****=p<0.0001.
Figure 14:
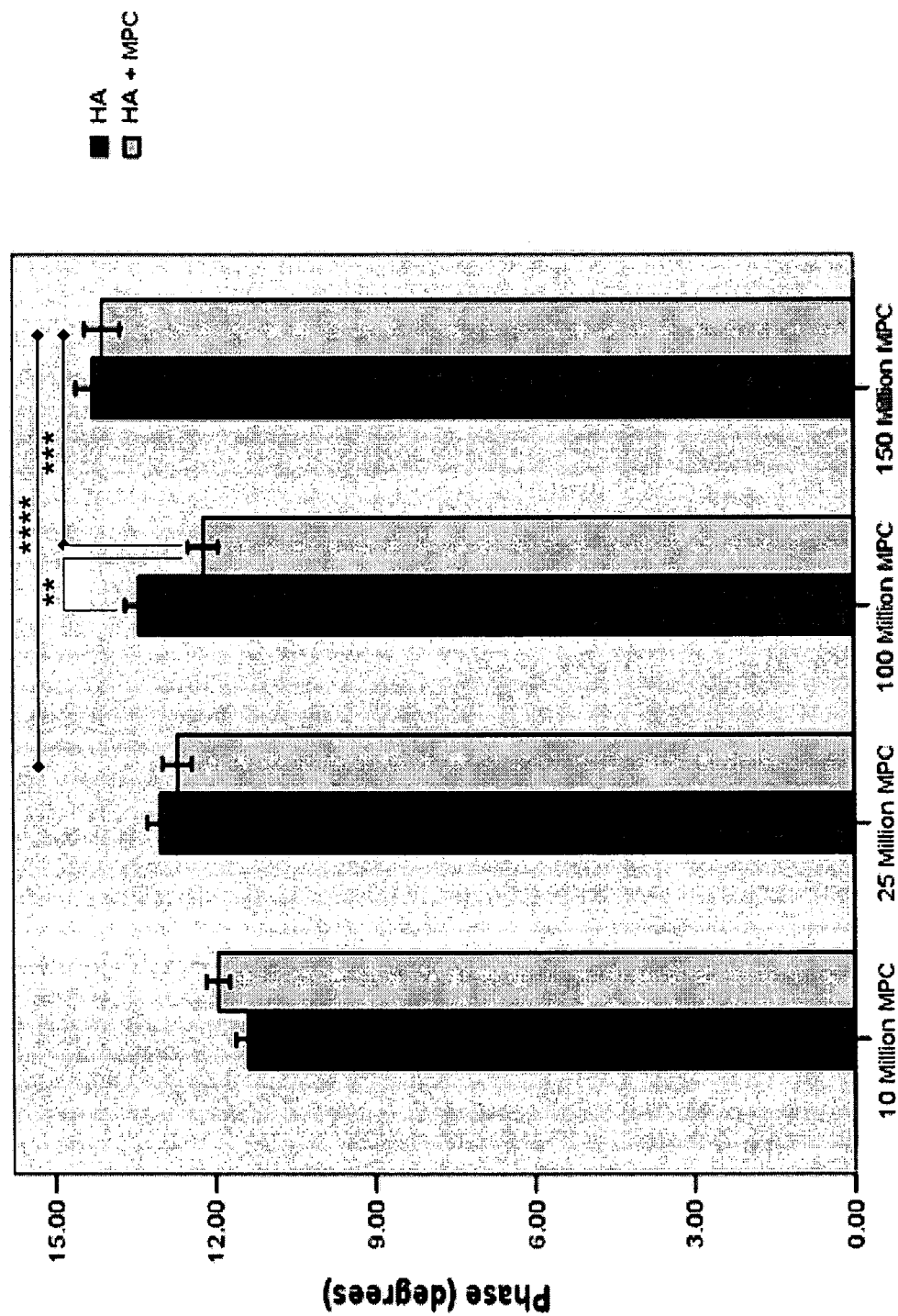
FIG. 14. Mean±/−SE of patella cartilage phase lag from joints injected with hyaluronan (HA) or HA+different doses of Mesenchymal Precursor Cells (MPC). *=p<0.05, =p<0.01, *=p<0.001, ****=p<0.0001.
Figure 15:
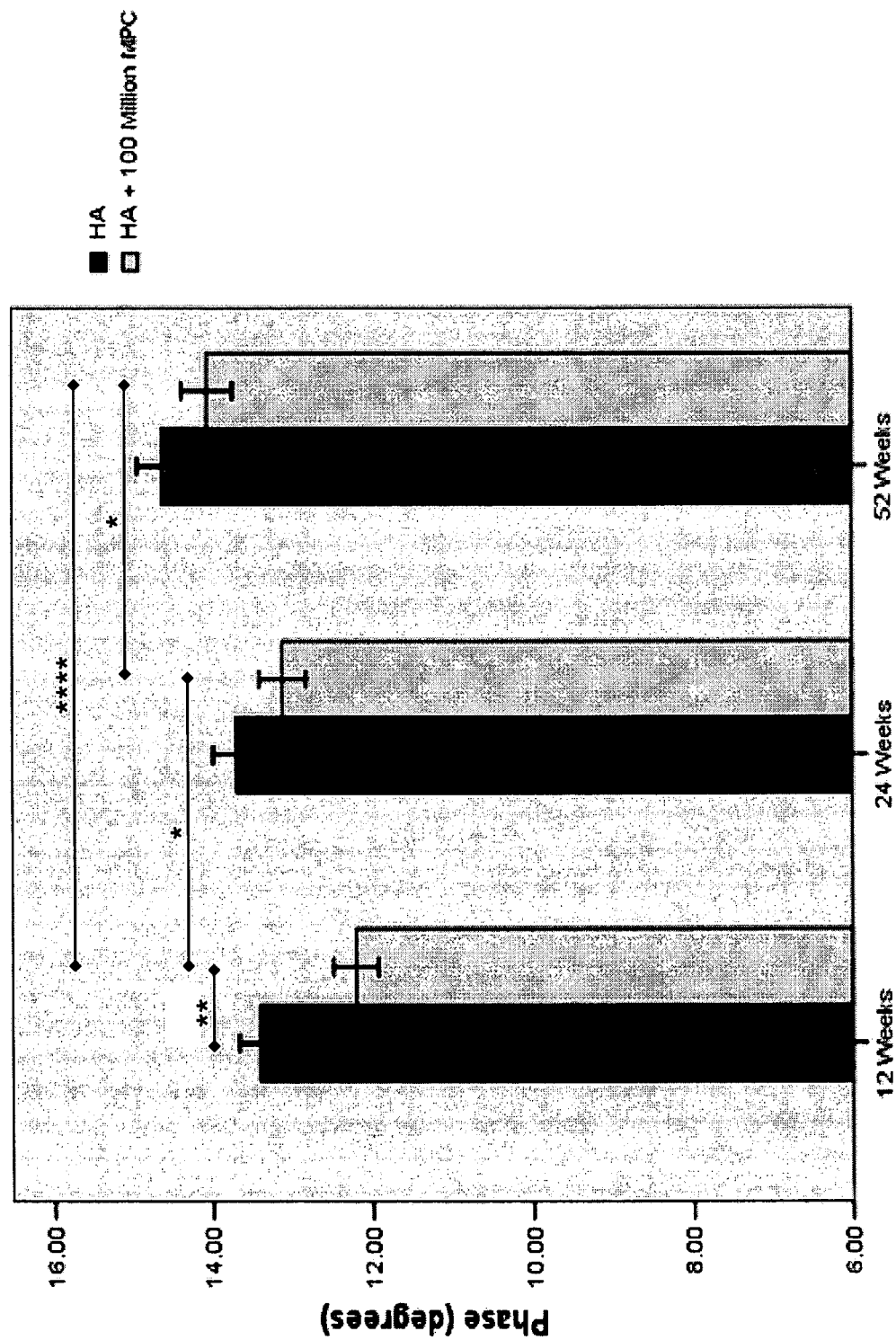
FIG. 15. Mean±/−SE of patella cartilage phase lag from joints injected with hyaluronan (HA) or HA+100 million Mesenchymal Precursor Cells (MPC) and sacrificed 12, 24 and 52 weeks post meniscectomy. *=p<0.05, =p<0.01, *=p<0.001, ****=p<0.0001.

Biomechanical indentation studies on the patella cartilages from joints of all the animal groups were generally consistent with the morphological and histological data. However, the stiffness of the cartilage is influenced by the thickness of the cartilage which in the early phases of injury may be hypertrophic but normalize with time. This situation may be occurring in the present model since the patella cartilage stiffness determined for the 25 and 100 million MPC groups were significantly less than the 10 and 150 million MPC groups which, from other studies exhibited the most damage tissues (FIGS. 12 and 13). This interpretation was supported by the phase lag data which was significantly lower for the patellae from the 100 million MPC group both relative to the corresponding HA injected joints and the 150 million MPC dose (FIG. 14). Moreover, the mean phase lag values observed at 12 weeks were found to significantly increase at 24 and 52 weeks post meniscectomy confirming the loss of a useful therapeutic effect of the injected MPC beyond 6-12 months (FIG. 15). Phase lag reflects the molecular assembly of the cartilage extracellular matrix and the lower the angle (Phase) the greater the elasticity and thus ability to recover from deformation (Cake et al., 2005).

The chondroprotective effects observed for the 100 mil MPC injected joints diminished with time; the positive effects noted at 12 and 24 weeks BTM being lost by 52 weeks.

There was no evidence of synovial histopathology modulation. Clinical and gross organ pathology conducted on these animals has not shown any evidence of systemic adverse effect of MPC.

Conclusions

This is the first report, as far as we are aware, of a beneficial therapeutic effect of allogeneic MPC on cartilage integrity in a model of early OA. MPCs are known to release growth factors and cytokines and also suppress the production of TNF-alpha by other cells, while up-regulating anti-inflammatory cytokines (eg. IL-4, IL-10). These paracrine activities of MPC could stimulate chondrocyte biosynthesis of new matrix but also attenuate local production and activity of catabolic mediators. The finding in this study that 100 million MPC were chondroprotective was consistent with such a mechanism of action. The data generated in these sheep studies indicate that the duration of the chondroprotective effect mediated by a single intra-articular injection of 100 million MPC is between 6-12 months post treatment suggesting that multiple injections may be required for the long term management of the OA patient.

While intra-articular injections of HA are widely used for the treatment of knee osteoarthritis there is limited evidence that this therapy is chondroprotective (Ghosh et al., 2002). However, intra-articular HA therapy is reported to provide symptomatic relief in OA which is of slow onset, but more sustained than with intra-articular corticosteroids (Bellamy et al., 2006).

Example 3

Relative Therapeutic Effects of Intra-Articular Injection of Hyaluronan (HA) or 100 Million Mesenchymal Precursor Cells (MPC)+HA on Cartilage Integrity in a Model of Severe Osteoarthritis Induced by Bilateral Total Medial Meniscectomy in Stifle Joints of Ovariectomized Ewes The knee joint meniscus performs an important role in protecting articular cartilage (AC) against damage during normal joint articulation (Arnoczky et al., 1988). Total or partial excision of the meniscus in humans following its injury generally results in premature degeneration of AC and progression to osteoarthritis (OA) (Jorgensen et al., 1987; Roos et al., 1998 and McNicholas et al., 2000). Experimental studies have shown that unilateral or bilateral total meniscectomy in sheep also leads to premature breakdown of AC and the early onset of OA (Ghosh et al, 1990; Appleyard et al., 1999 and Ghosh et al., 1993c).

Since the failure of AC in meniscectomised joints is a consequence of the imposition of high focal and shearing stress on cartilage, bilateral meniscectomy was found to induce a more rapid progression of cartilage degeneration than unilateral meniscectomy where supportive pain-free weight bearing can be accommodated by use of the contralateral non-operated hind limb (Ghosh et al., 1993a and 1993b; Appleyard et al., 2003; Little et al., 1997 and Oakley et al., 2004). Furthermore, ovariectomised ewes subjected to bilateral meniscectomy have also been shown to undergo a more progressive OA than adult castrated males (wethers), largely due to the depletion from their circulation of the cartilage protective hormone, oestrogen (Parker et al., 2003). For these reasons ovariectomised and bilaterally meniscectomised ewes are favoured as a large animal model of OA to study the disease modifying activities of anti-OA agents (Ghosh et al., 1993; Smith et al., 1997; Burkhardt et al., 2001; Hwa et al., 2001 and Cake et al., 2000). The ovariectomised/bilaterally meniscectomised sheep model of OA was therefore selected for the present investigation—the purpose of which was to evaluate the effects of intra-articularly (IA) administered allogeneic Mesenchymal Precursor Cells (MPC) on induction of growth or regeneration of proteoglycan-rich cartilage and on chondroprotection relative to a currently used anti-OA therapy, IA Hyaluronan (HA).

Methods

Bilateral total medial meniscectomy (BTM) was undertaken in 18 adult Merino ewes that had undergone ovariectomy 3 months previously using a published method (Cake et al., 1004). The surgical procedure and post-operative regimen used for BTM was identical to that described for the castrated male sheep BTM studies described in Example 2.

Twelve weeks post BTM, 6 ewes were sacrificed while the stifle (knee) joints of the remaining 12 meniscectomised ewes were randomly injected with either 2 mL high MW HA or 100 million MPC suspended in 2 mL Profreeze® plus 2 mL HA. This dose of MPC+HA was shown in Example 2 to afford the most beneficial chondroprotective effects in the BTM male sheep model. The meniscectomised and injected ewes were divided into two groups of 6 that were sacrificed 24 and 36 weeks post-BTM, i.e. 12 and 24 weeks post HA or MPC+HA intra-articular injection. To determine the effects of gender on the response of AC joint destabilization 6 untreated castrated male sheep were also subjected to BTM and sacrificed 12 weeks post-meniscectomy.

At necropsy, joints were opened, menisci removed and the medial femoral and tibial plateux photographed. The recorded images were scored by 2 blinded observers for gross morphological changes to cartilage using a 0-4 scale. Synovium from the suprapatellar fold and a 5 mm wide coronal osteochondral slice were removed from the mid-line of the femur and tibia of each joint and processed for preparation of histological sections. Cartilage histopathology was assessed by two blinded observers using a modified Mankin Scoring system as described previously (Little et al., 1997). Synovial histopathology was scored using the criteria recently described by Cake et al., 2008.

Histological serial sections from the same cartilage blocks as used for Mankin Scoring were also utilized for histomorphometric analysis as described previously (Caket et al., 2000; Cake et al., 2004). This technique employs computer-aided image analysis (ImagePro Plus v.3.0, Media Cybernetics) to generate quantitative data on the dimensions and an index of the proteoglycan content of Toluidine blue stained AC. In brief, images of the stained sections were acquired via a Microtek Slidescanner 35t plus (Microtek Model No. PTS-1950) at a resolution of 1300 dpi and then analysed using Image J® software (http://rsb.info.nih.gov/ij/) on a personal computer. The digital images of the femoral and tibial sections were subdivided into inner, middle and outer regions, each region representing approximately one third of the total area of the cartilage sections. Spatial calibration of the system was achieved by scanning a 10×10 mm high precision reticule. This scale was then used to quantify the length (mm) and area ($mm^2$) in of each region of the imported images. The average thickness of the sections was determined by dividing the area by the length. The optical density (OD) of the TB stained cartilage sections was obtained as the mean grey value (MGV) (sum grey values/number of pixels) and was taken as an index of proteoglycan (PG) content. The integrated grey-scale density (IGD) was calculated as MGV×regional area of section. Although the grey scale system used was not independently calibrated against TB stained sections of known PG content, all histological sections were cut on the same microtome, were the same thickness and were processed as a group using the same staining protocol. Differences in cartilage staining are therefore relative rather than absolute. Intact patellae from all joints were removed within 1 hour of sacrifice and immediately frozen and stored prior to topographical biomechanical indentation studies to determine the stiffness and phase lag of the articular cartilage (Appleyard et al., 2003).

Statistical analysis to identify differences in treatments outcomes (HA versus HA+MPC) or treatments versus untreated 12 week post BTM controls, as assessed by the morphological and histological scoring systems, was undertaken using Kruskal-Wallis nonparametric analysis and for differences between group comparisons using Mann Whitney U nonparametric analysis with p<0.05 considered significant.

Data generated by the histomorphometric analysis of digitised histological sections were evaluated using the equal variance Two Tailed Student's T-Test with p<0.05 considered to be significant. Statistical analysis of patella cartilages biomechanical parameters with respect to different treatments and between time post-BTM was calculated using an independent T-Test with p<0.05 considered significant.

Results

The gross morphological assessment of cartilage erosions and osteophyte formation in joints from the untreated ewes 12 weeks post-BTM confirmed that this model of OA represented a more aggressive and severe form of the disease compared with meniscectomised castrated males subjected to the same surgical procedure. For this untreated female control group the mean cartilage morphological score for the femur was 87% and for the tibia 75% of the maximum scores used to assess this parameter. The gross morphology scores obtained for the joints derived from the untreated 12 week post meniscectomised castrated males subjected to the same surgical procedure was significantly less than for the ovariectomised ewes (FIGS. 16 and 17) a finding which was consistent with previous observations using bilateral lateral meniscectomy (Parker et al., 2003; Cake et al., 2004).

While both treatments resulted in lower mean femoral morphological cartilage scores at 24 and 36 weeks than the baseline untreated 12 week post-meniscectomised ewes (data not shown), no significant differences were detected between the MPC and HA treated joints. We interpret this to mean that in this model of severe OA, the severity of the gross morphologic lesions (erosion and osteophyte scores) make these parameters too insensitive to detect therapeutic differences.

Figure 16:
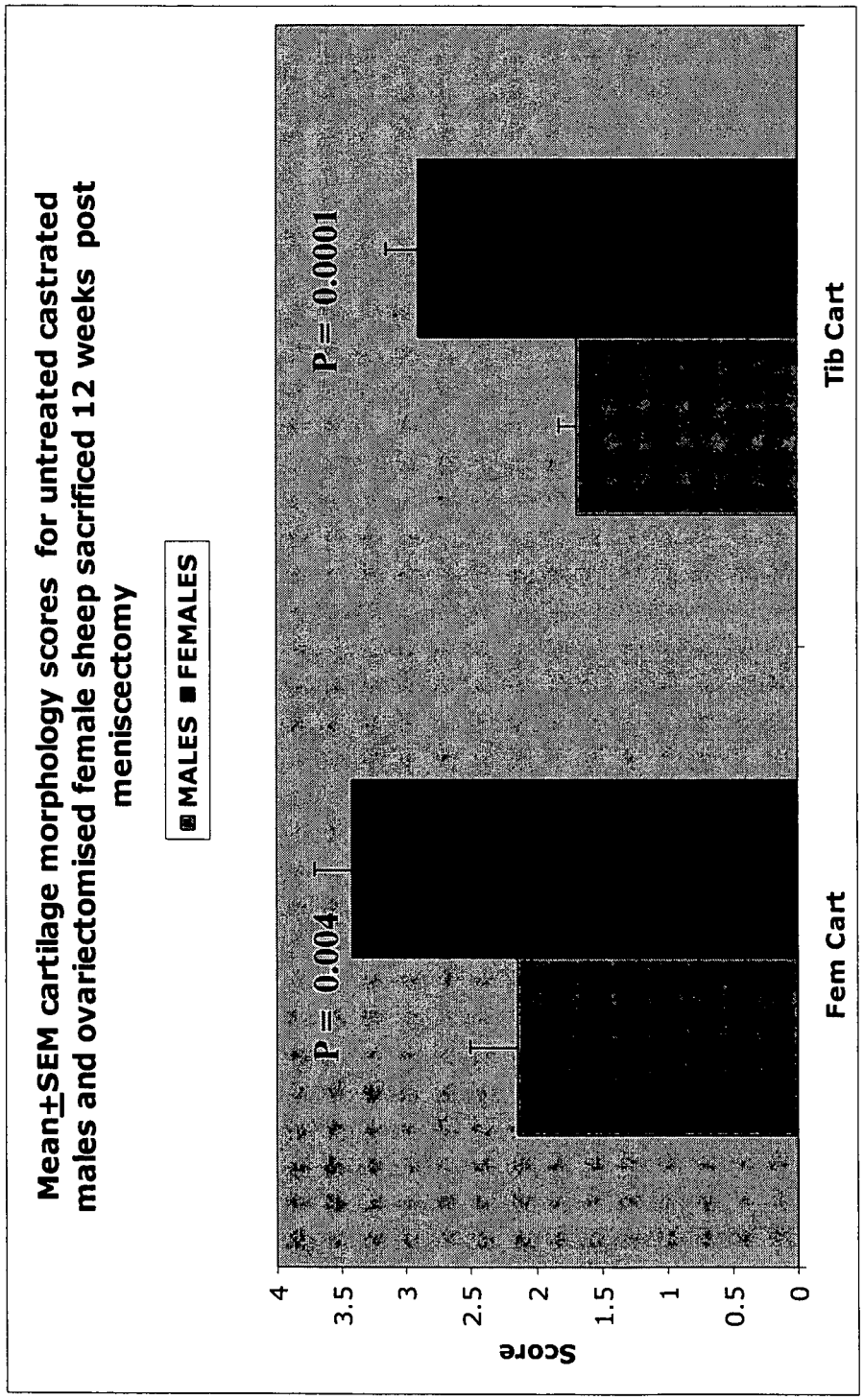
FIG. 16. Comparison of joint cartilage morphology scores for untreated castrated male sheep and ovariectomised ewes 12 weeks post meniscectomy showing the significantly greater severity of OA lesions in the female group.
Figure 17:
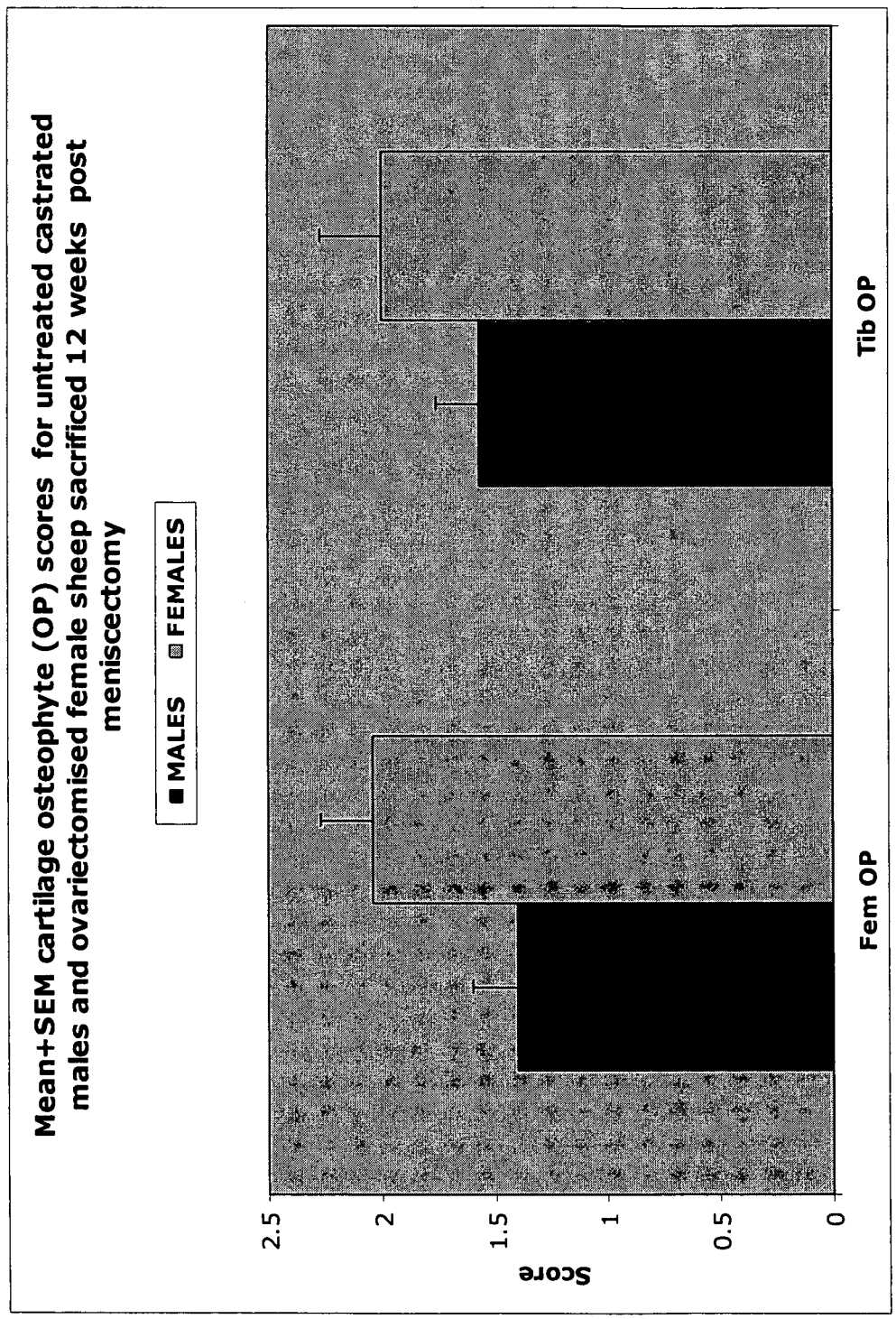
FIG. 17. Comparison of joint osteophyte scores for untreated castrated male sheep and ovariectomised ewes 12 weeks post meniscectomy showing the significantly higher scores in the female group.
Figure 18:
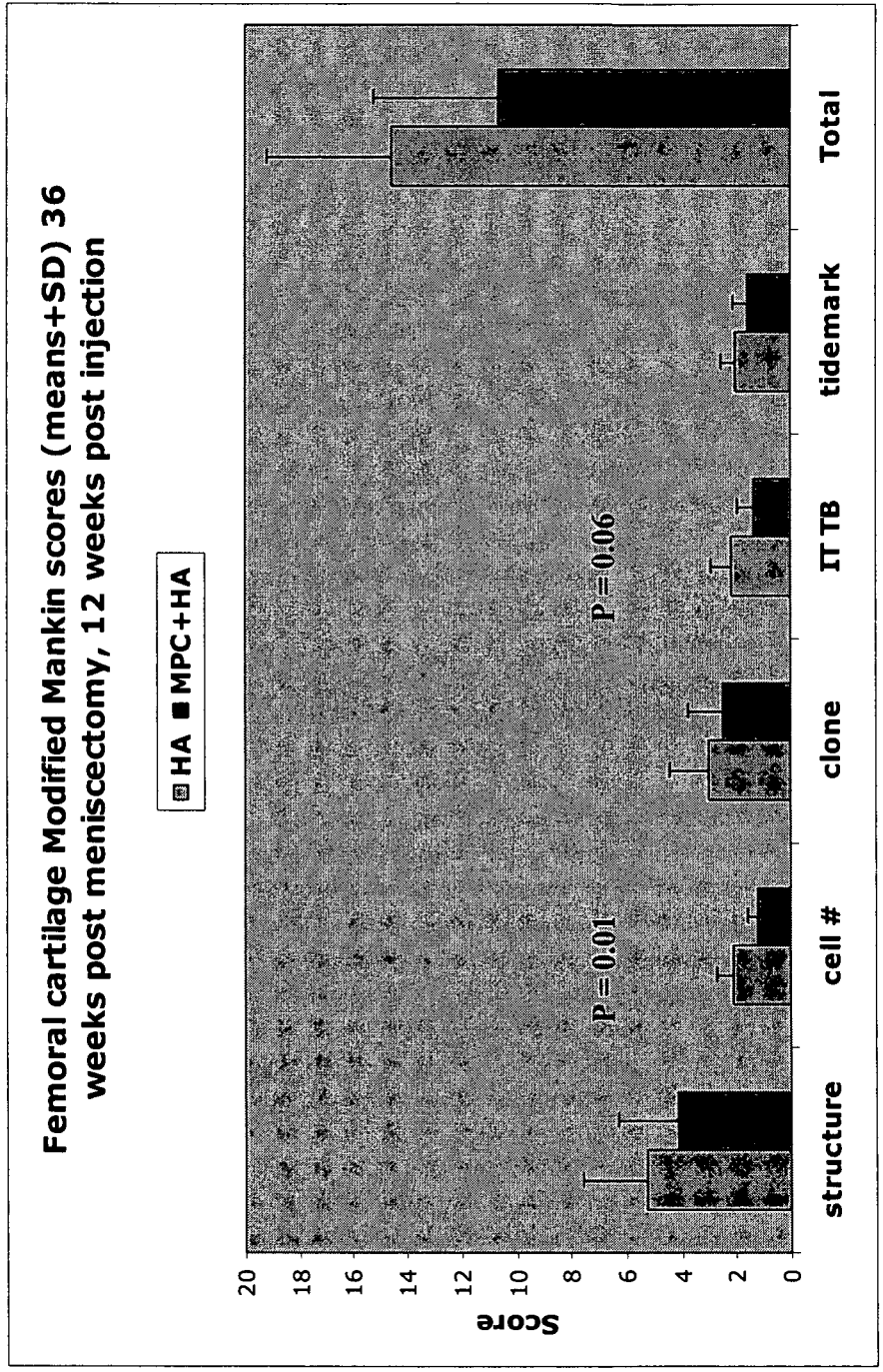
FIG. 18. Mean±SD of cartilage Modified Mankin Histopathology scores 36 weeks post meniscectomy from joints of ovariectomised ewes injected with Hyaluronan (HA) or HA+100 million Mesenchymal Precursor Cells (MPC) 12 weeks post meniscectomy. P values=HA versus MPC+HA. These results show that a single MPC injection reduces abnormal histopathologic score of femoral hyaline cartilage over 6 months to a greater extent than tibial cartilage.
Figure 18:
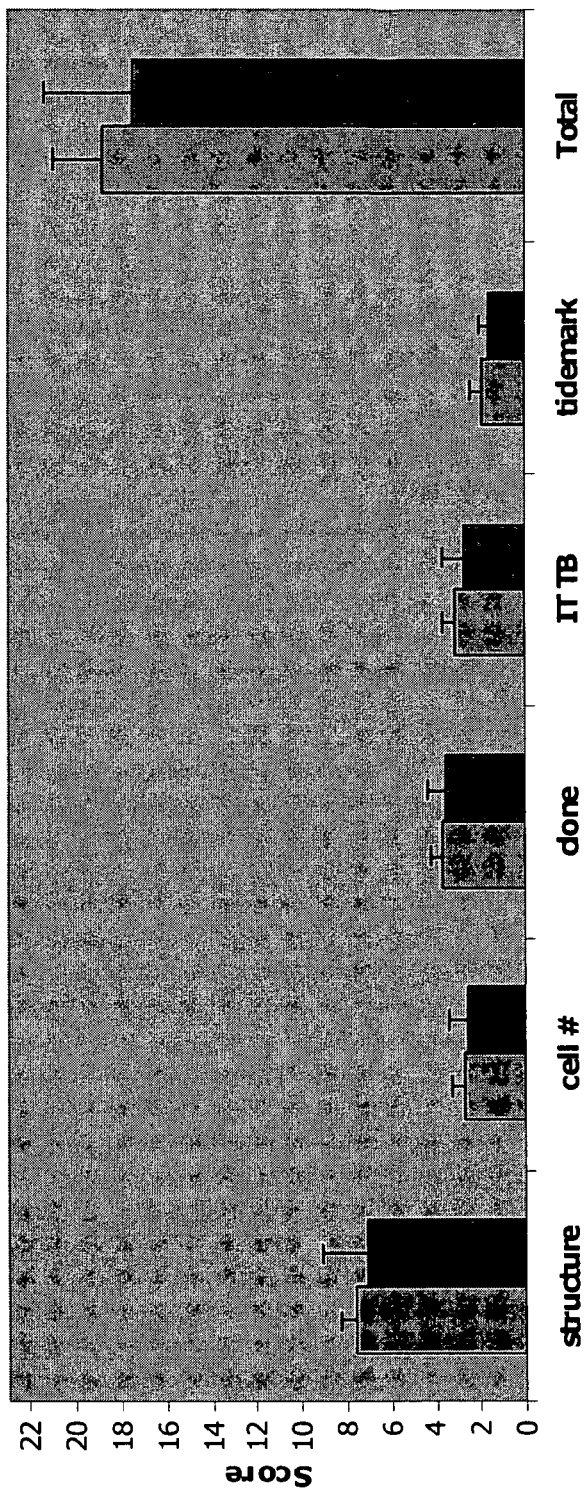

Modified Mankin histopathology scores for cartilages from the untreated 12 weeks post-BTM group were found to be consistent with the extent of cartilage damage as assessed morphologically (FIGS. 16 and 17). In contrast to morphologic parameters, at 36 weeks the total mean modified Mankin score for the femoral cartilages in the ovariectomised ewes who received MPC+HA was lower than the corresponding score for the joints that received HA alone and showed a significantly lower cell number (p=0.01) and a trend (p=0.06) for stronger inter-territorial Toluidine Blue (IT TB) staining for proteoglycans than HA alone (FIG. 18). These effects were less pronounced for the tibial cartilages (FIG. 18).

Figure 19:
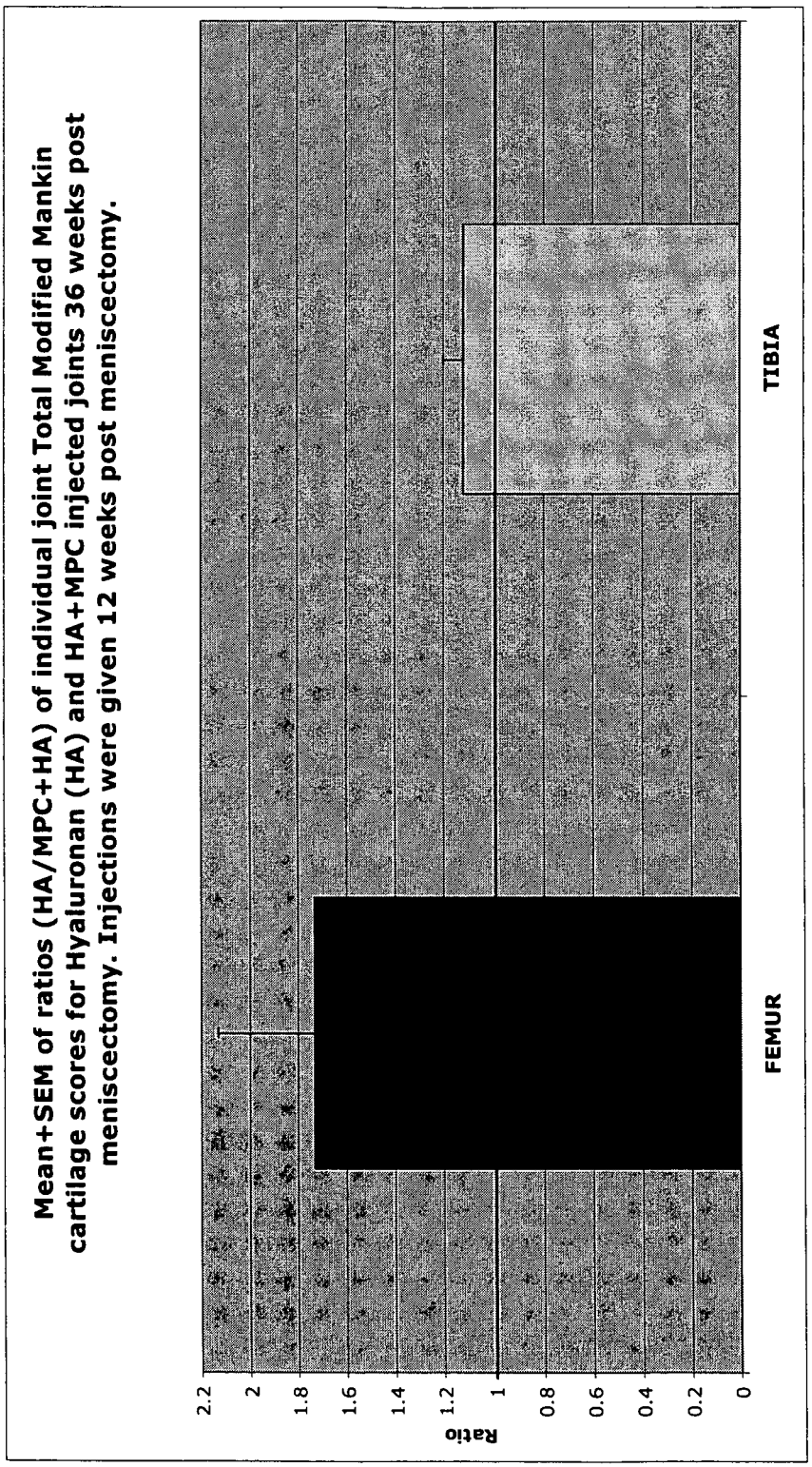
FIG. 19. Ratios (HA/HA+MPC) of cartilage Total Modified Mankin Histopathology Scores for joints of ovariectomised ewes 36 weeks post meniscectomy administered intra-articular injections 12 weeks post meniscectomy. When ratio=1, MPC+HA equivalent to HA. Ratio>1, shows MPC+HA more protective than HA alone. Data=Means±SEM. These results show that a single MPC injection reduces abnormal histopathologic score of femoral hyaline cartilage over 6 months to greater extent than tibial cartilage.

The lower Modified Mankin histopathology cartilage score observed for the MPC+HA injections at 36 weeks post meniscectomy relative to the HA injected joints was highlighted when the ratio of the mean total Modified Mankin scores for the two intra-articular treatments were determined (FIG. 19). As each ratio was obtained from the two treated joints of the same animal a ratio=1 would indicate that both treatments were equally effective. However, for the ratios>1 the MPC+HA treatment can be said to be more beneficial. As is evident from FIG. 19 the mean of the ratios obtained for the femoral cartilages were significantly higher (1.71) than unity at 36 weeks post-BTM while the tibial cartilage ratios (1.12) for the two treatments were only slightly in favor of the MPC+HA injected group (FIG. 19).

Figure 20:
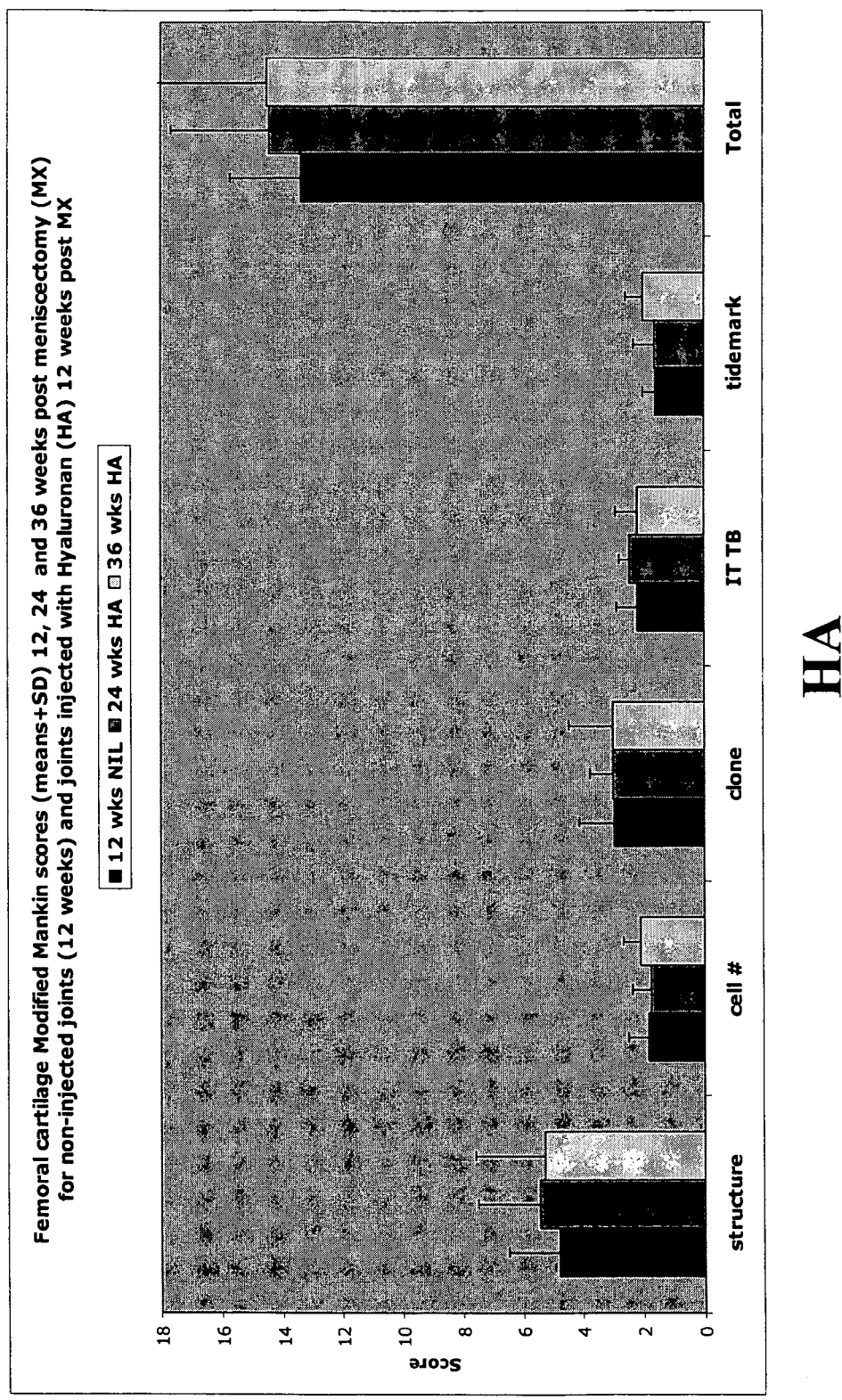
FIG. 20. Mean±SD of femoral cartilage Modified Mankin Histopathology scores 24 and 36 weeks post meniscectomy (MX) from joints of ovariectomised ewes injected with Hyaluronan (HA) or 100 million Mesenchymal Precursor Cells (MPC)+HA 12 weeks post MX compared with non-injected joints at 12 weeks post MX. P values are for 12 wks NIL versus treatments. These results show that a single MPC injection reduces abnormal histopathologic score over 6 months.
Figure 20:
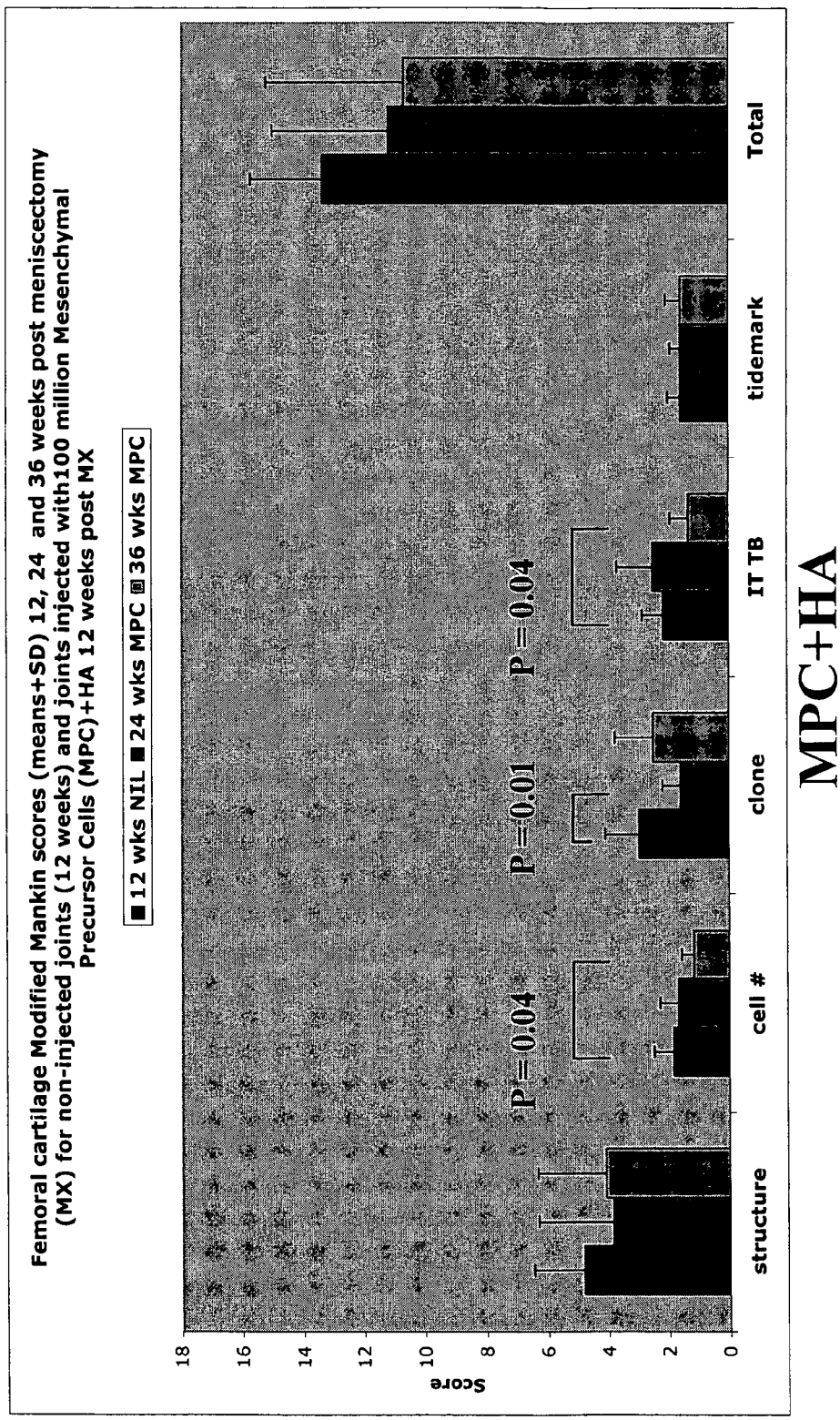

Next we examined the effect of the treatments on Mankin scores over time. Significant differences in effects on femoral cartilage over time were found between the MPC+HA and the HA alone treatment arms at 24 and 36 weeks post meniscectomy, i.e. 12 and 24 weeks post-injection (FIG. 20). In the group receiving MPC+HA, mean scores at 24 and 36 weeks were progressively lower than at the 12 week baseline. This was due to reduced scores and improvement in cell cloning (P=0.01) at 24 weeks, and in cell numbers (P=0.04) and inter-territorial Toluidine Blue staining for proteoglycans (PGs) (P=0.04) at 36 weeks relative to the 12 week untreated group (FIG. 20). No such improvements were seen in the HA alone group. No significant differences were observed between the synovial pathology scores for any of the groups or intra-articular treatments.

Figure 21:
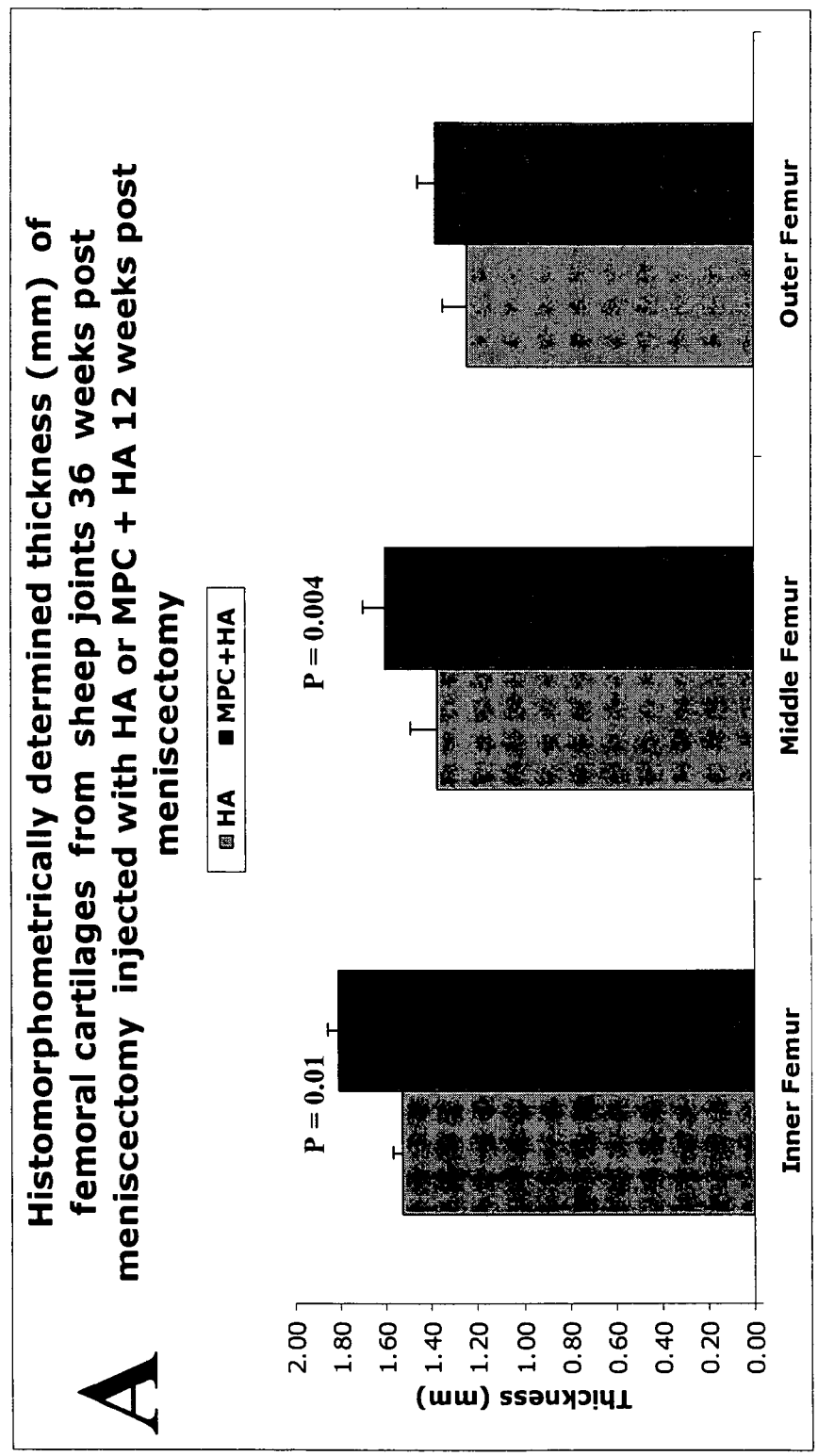
FIG. 21. Femoral cartilage histomorphometry data 36 weeks post meniscectomy from joints of ovariectomised ewes injected with Hyaluronan (HA) or 100 million Mesenchymal Precursor Cells (MPC)+HA 12 weeks post meniscectomy. Data shown=Mean±SEM. P values=HA v MPC+HA. These results show that a single MPC injection generates greater hyaline cartilage over 6 Months than hyaluronic acid.
Figure 21:
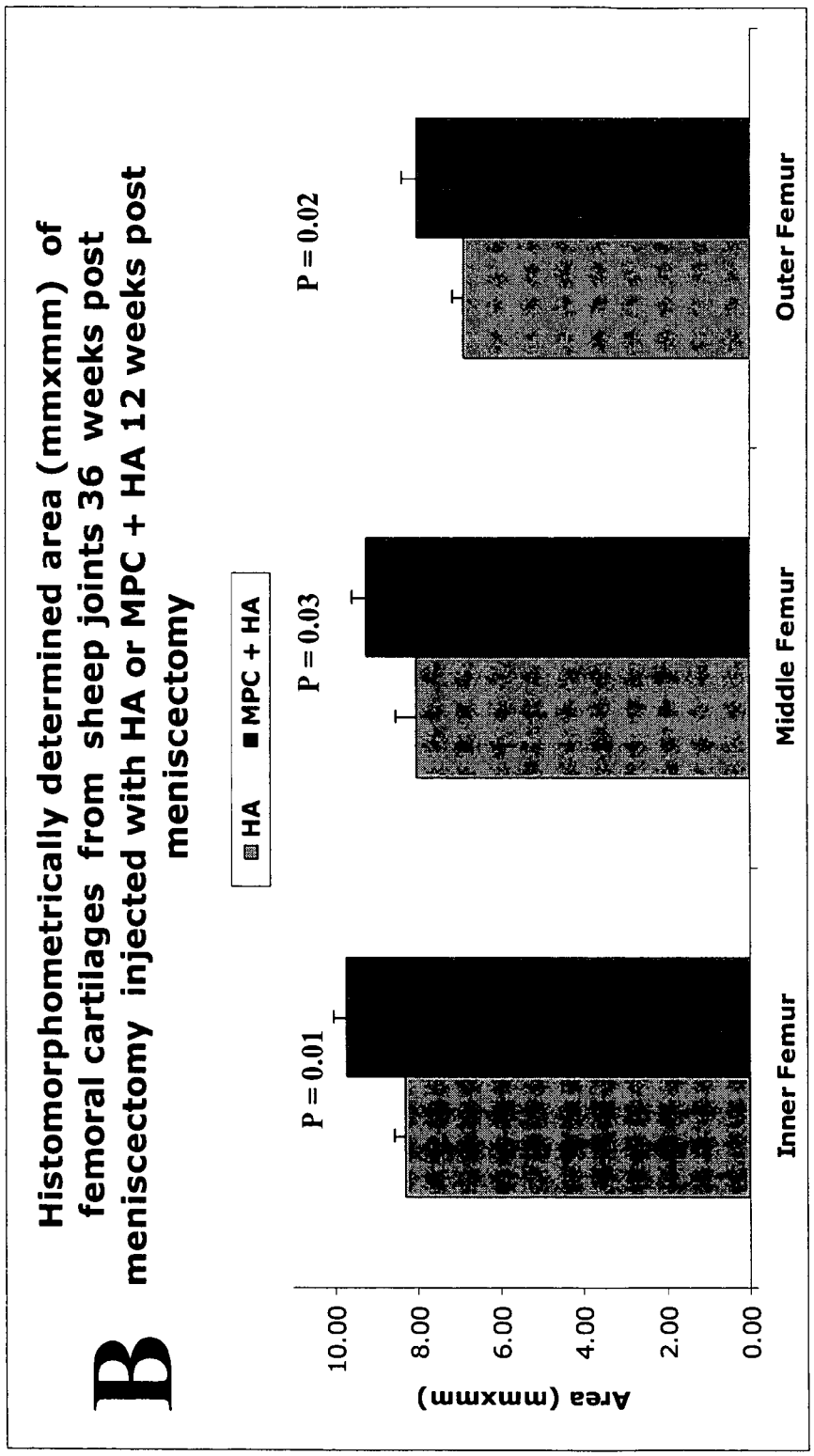
Figure 21:
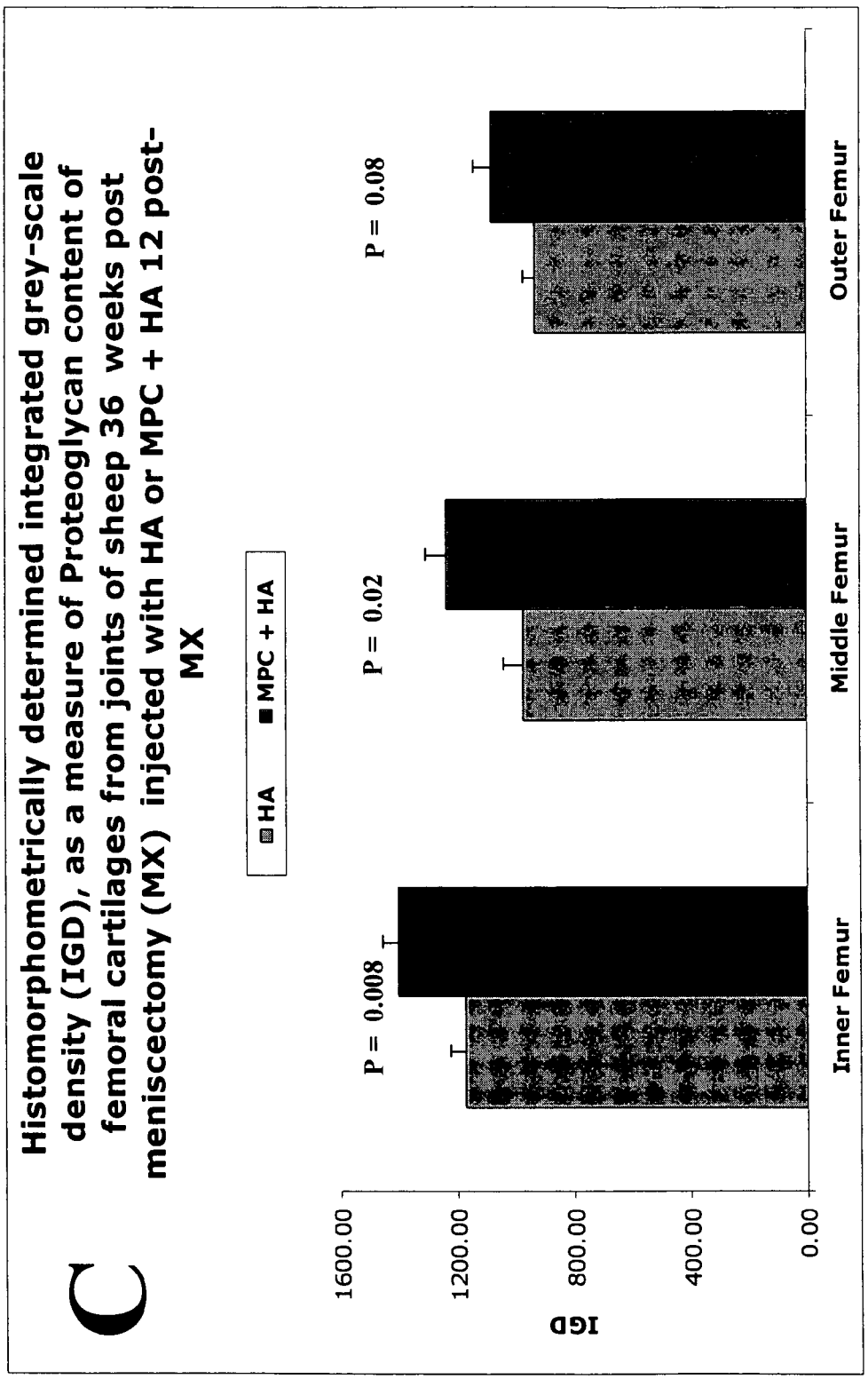

The analysis of cartilage thickness, area and intensity of TB staining as an index of PG content for the 3 regions (inner, middle and outer) of the femoral condyles from the injected joints at 36 week post-BTM using histomorphometric methods of analysis are shown in FIG. 21. By 36 weeks post-BTM significant differences between treatments groups were evident. Femoral cartilages from the MPC+HA injected joints were significantly thicker (FIG. 21A) and occupied a significantly larger area (FIG. 21B) than the corresponding cartilages of HA injected joints. The larger volume of the femoral cartilages from the MPC+HA injected joints was accompanied by a higher content of proteoglycans as determined from the integrated grey-scale density of the TB stained sections (FIG. 21C).

Figure 22:
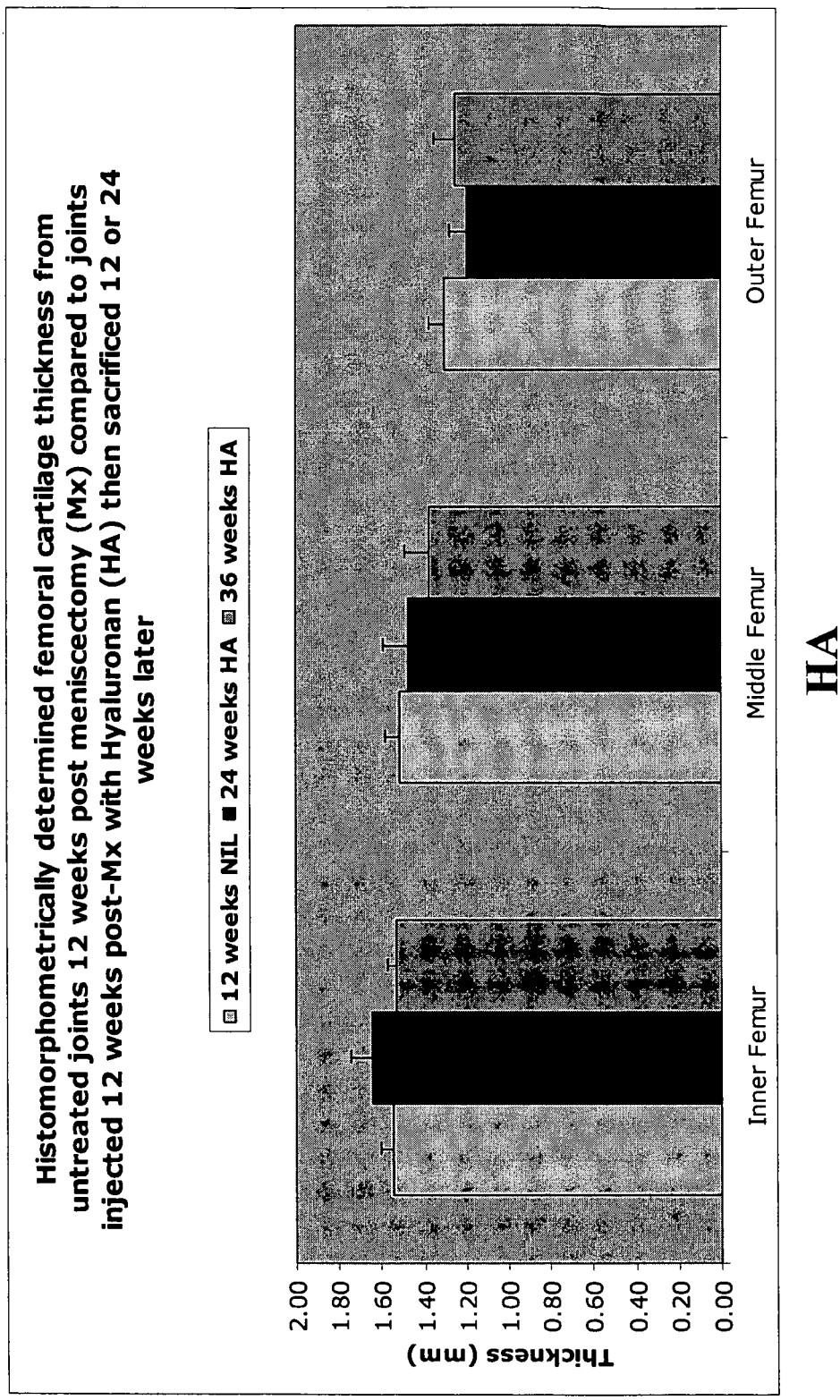
FIG. 22. Mean±SEM histomorphometrically determined femoral cartilage thickness of joints from untreated ewes sacrificed 12 weeks post meniscectomy (Mx) or injected with Hyaluronan (HA) or Mesenchymal Precursor Cells (MPC)+HA at 12 weeks post Mx then sacrificed 12 or 24 weeks later. Data expressed as Mean±SEM. P values relative to 12 week NIL treated. These results show that a single MPC injection increases hyaline cartilage thickness over 6 months.
Figure 22:
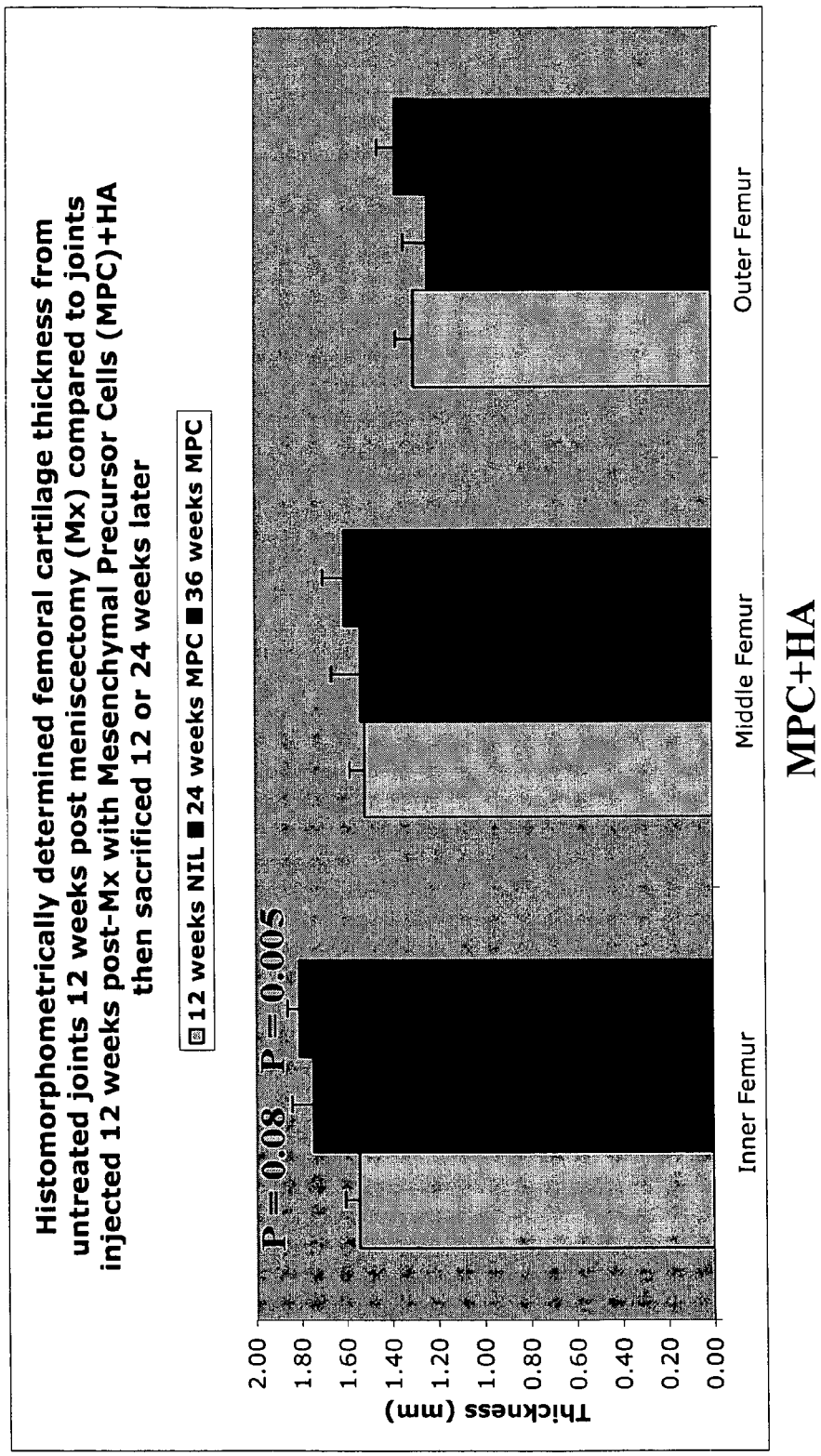
Figure 23:
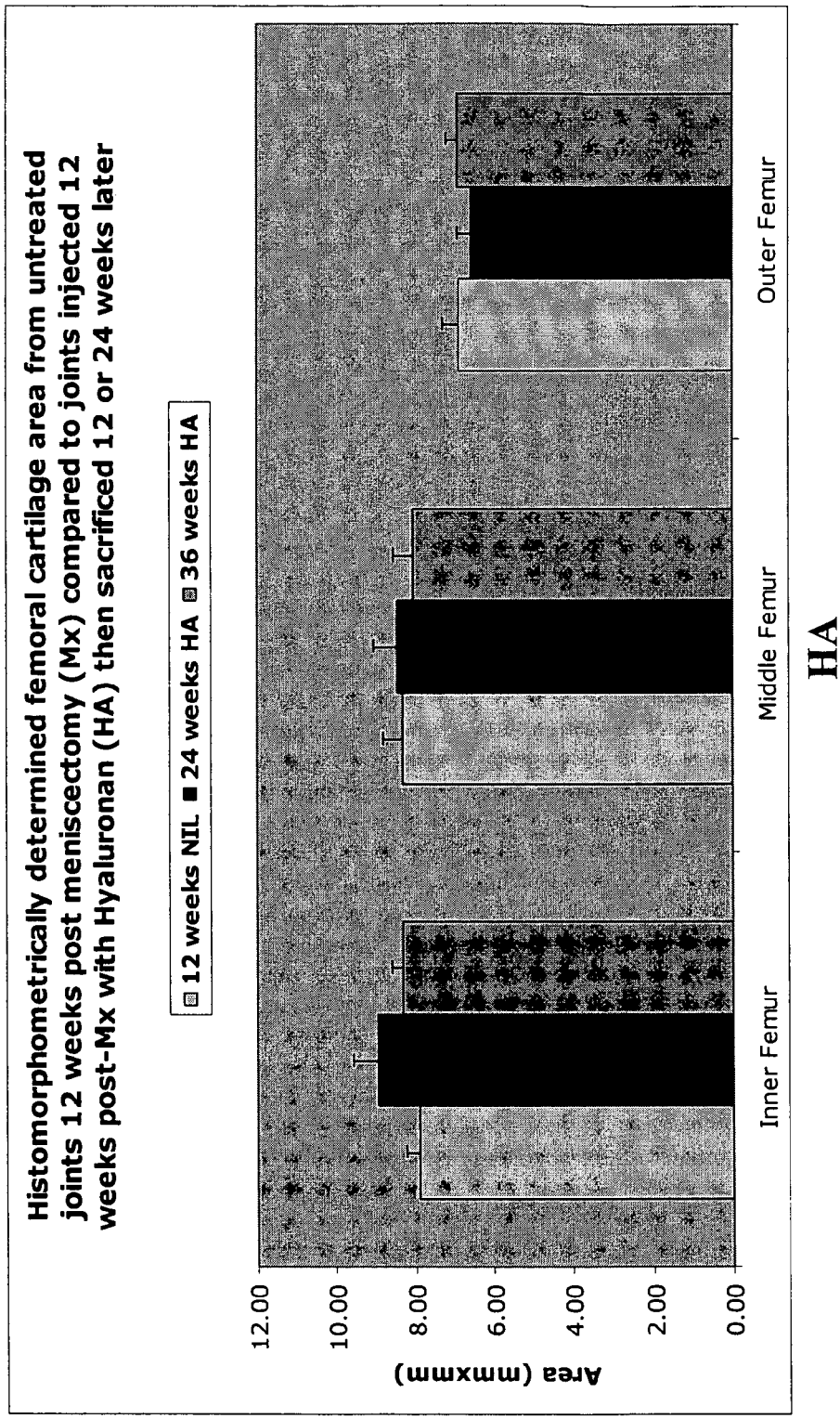
FIG. 23. Histomorphometrically determined femoral cartilage areas of joints from untreated ewes sacrificed 12 weeks post meniscectomy (Mx) or injected with Hyaluronan (HA) or Mesenchymal Precursor Cells (MPC)+HA at 12 weeks post Mx then sacrificed 12 or 24 weeks later. Data expressed as Mean±SEM. P values relative to 12 week NIL treated. These results show that a single MPC injection increases hyaline cartilage area over 6 months.
Figure 23:
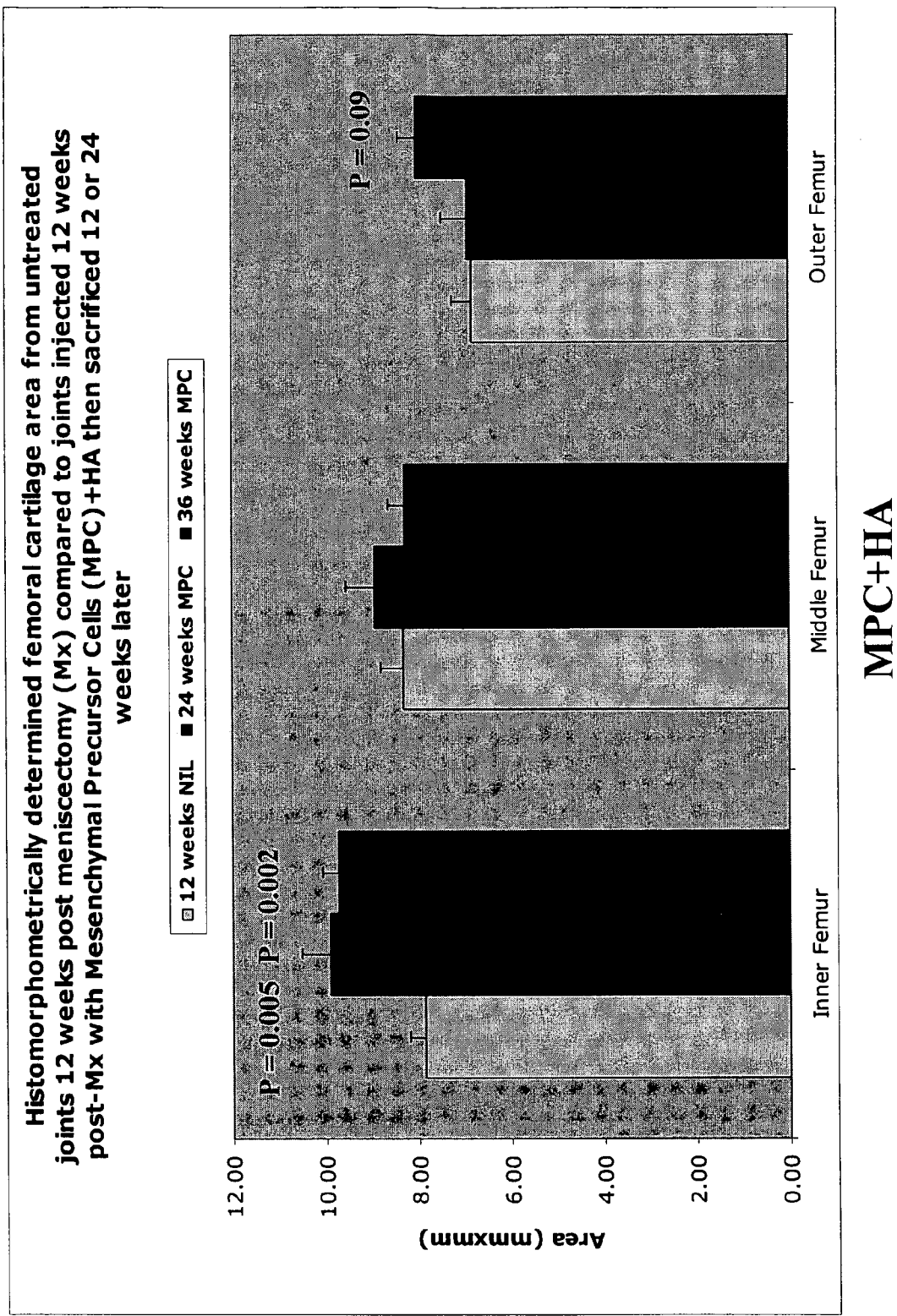
Figure 24:
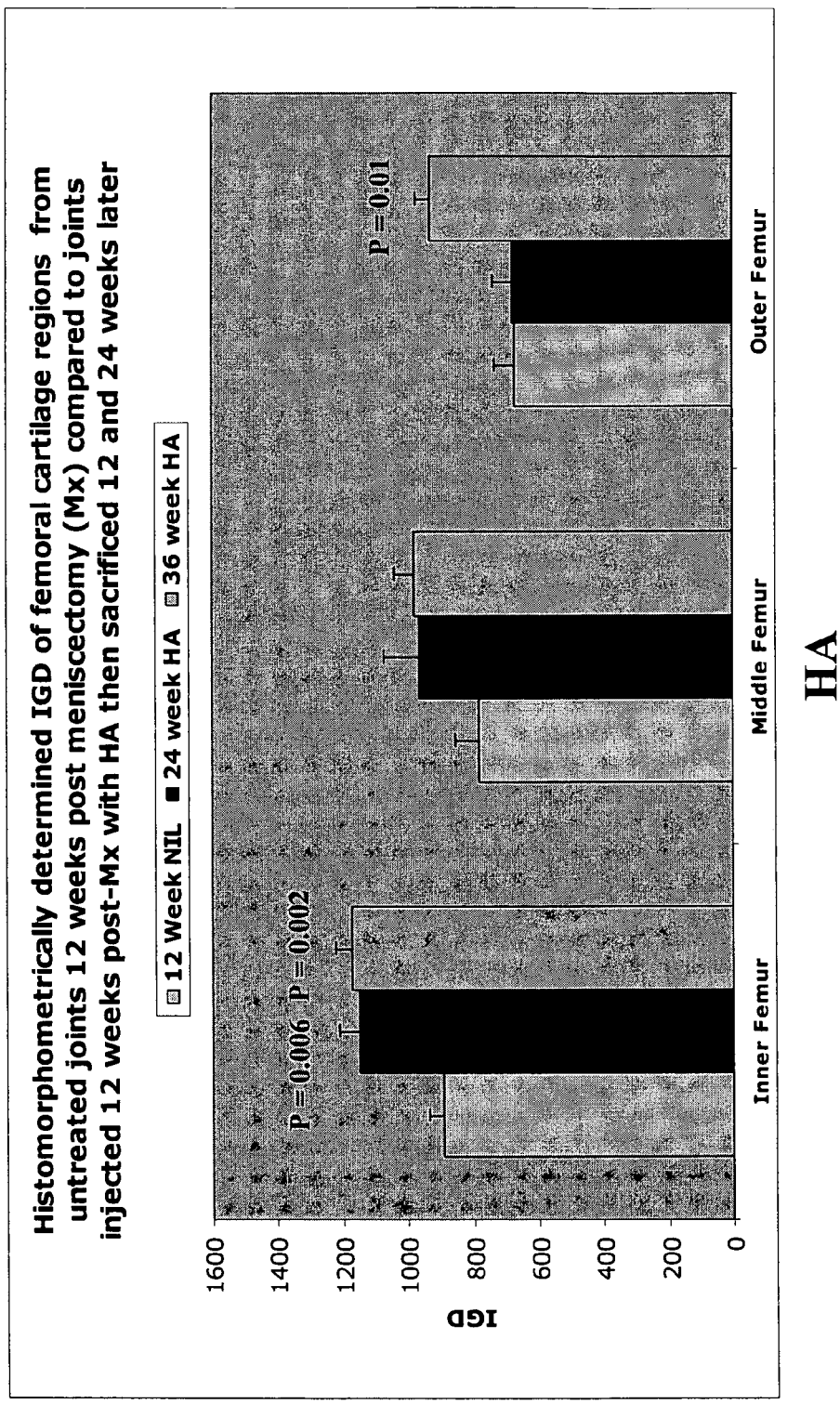
FIG. 24. Histomorphometrically determined Integrated Grey-scale Density (IGD) as a measure of overall Proteoglycan (PG) content of femoral cartilages from joints of untreated ewes sacrificed 12 weeks post meniscectomy (Mx) or injected with Hyaluronan (HA) or Mesenchymal Precursor Cells (MPC)+HA at 12 weeks post Mx then sacrificed 12 or 24 weeks later. Data expressed as Mean±SEM. P values relative to 12 week NIL treated. These results show that a single MPC injection generates significantly more cartilage containing proteoglycan than hyaluronic acid injection over 6 months.
Figure 24:
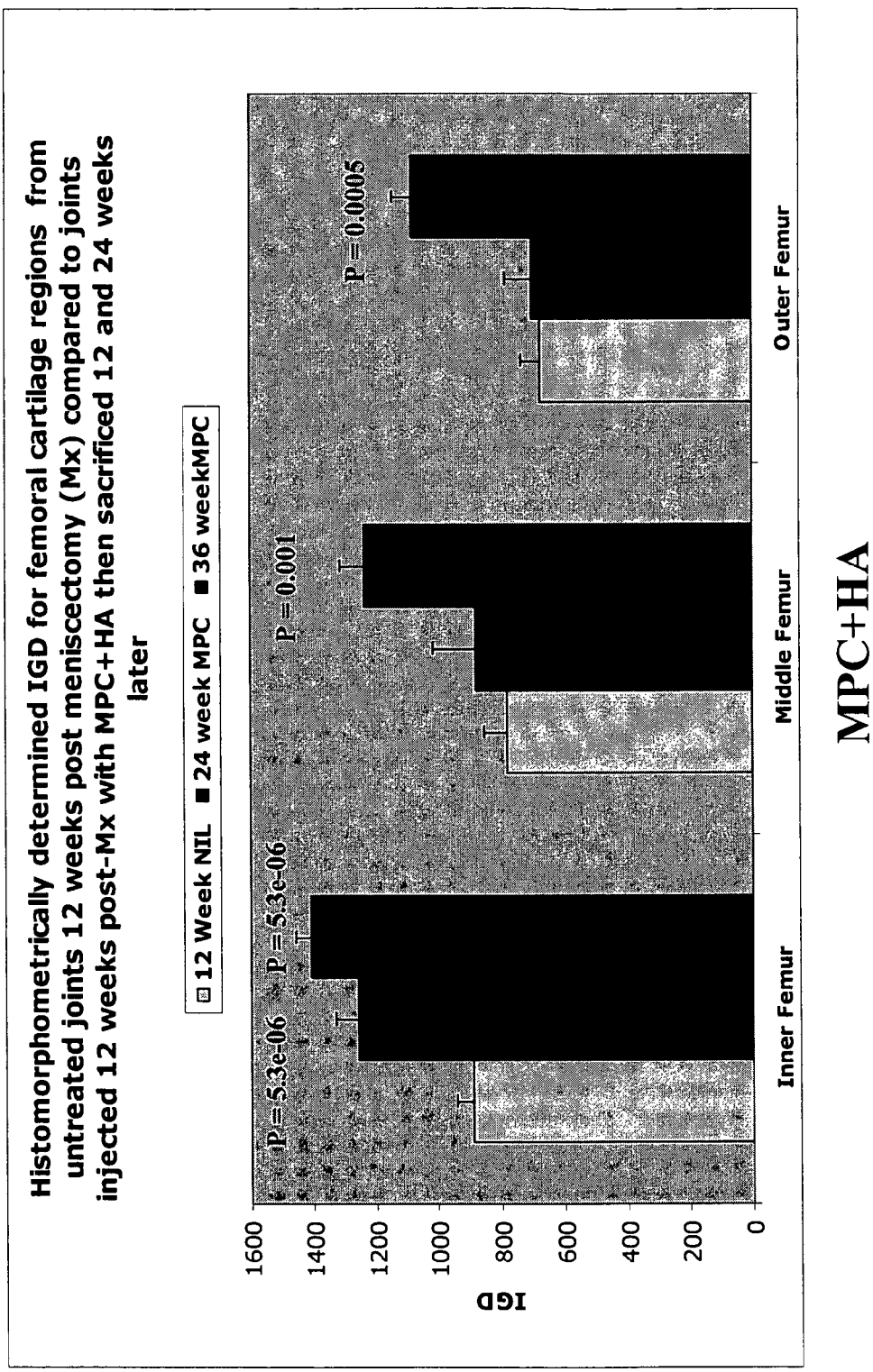

Again comparing these parameters in a time-based analysis, significant differences in effects on femoral cartilage over time were found between the MPC+HA and the HA alone treatment arms at 24 and 36 weeks post meniscectomy, i.e. 12 and 24 weeks post-injection. Using the same histomorphometric methodology, we were able to demonstrate that the MPC+HA injection administered 12 weeks post meniscectomy resulted in progressively greater proteoglycan-rich femoral cartilage growth or regeneration 12 and 24 weeks later (i.e. at 24 and 36 weeks post-BTM) than HA alone (FIGS. 22 to 24). Thus, femoral cartilages at 24 and 36 weeks post-BTM from joints of meniscectomised ewes injected with MPC+HA at 12 weeks were significantly thicker (FIG. 22) and generally had larger areas (FIG. 23) than the baseline values from untreated joints at 12 weeks post-meniscectomy. The corresponding regions scanned from sections of femoral cartilage derived from HA injected joints failed to demonstrate statistically significant changes relative to the 12 week untreated controls (FIGS. 22 & 23). The integrated grey-scale density as a measure of PG content of sections of femoral cartilages was significantly higher for both HA and MPC+HA injected joints relative to the same cartilage regions of joints from the untreated 12 week post-BTM group but the magnitude of the MPC+HA induced change was significantly greater than HA alone (FIG. 24). Whereas the MPC+HA group developed almost 60% greater proteoglycan-rich femoral tissue at 36 weeks compared with baseline (P<0.001), and this rate of cartilage growth had not reached a plateau phase, the HA only group had reached a plateau phase and developed only about 30% greater tissue. This indicated that treatment with MPC+HA stimulated significantly greater increase in proteoglycan-rich cartilage over the 24 week period of follow-up (i.e. growth and/or regeneration of cartilage) relative to both baseline and to any temporal effects of HA treatment alone.

The results of the indentation studies on the patella cartilages from the injected joints failed to demonstrate any difference in the biomechanical properties of the cartilages for the two treatments but changes were identified with respect to time elapsed post meniscectomy and the untreated 12 week post-BTM group. The stiffness of the patella cartilages from the MPC+HA at 24 weeks post-meniscectomy was significantly higher than at 12 weeks (P=0.05) and 36 weeks (P<0.01) (data not shown). However, both treatments produced thicker patella cartilage 36 weeks compared to 24 weeks (P=0.001) that was also lower than the non-treated 12 week control (P=0.01). Patella cartilage phase-lag for both treatment groups at 24 and 36 weeks were higher than the untreated 12 week controls (P=0.001) (data not shown).

Discussion

The present studies have shown that bilateral medial meniscectomy in ovariectomised ewes induced pathological changes in joint articular cartilage after 3 months that were consistent with progressive and severe OA. Thus the gross morphology scores for the femoral and tibial cartilages were 87-70% of the maximum score. Interestingly, castrated males subjected to the same surgical procedure and sacrificed at the same time (12 weeks) showed less severe cartilage lesions than the observed for the ovariectomised females. The extent of cartilage pathology was also reflected in the high aggregate Modified Mankin histopathology scores observed for this group that were consistent with the assignment of early OA (Little et al., 1997). Although previous studies had identified a strong association of OA in postmenopausal females, which was explained by the depletion of estrogen from the circulation (Roos et al., 2001; Pelletier et al., 2007 and Nevitt et al., 1996) and was supported by studies in ovariectomised ewes (Parker et al., 2003 and Cake et al., 2004), other more recent studies suggests that the adipose derived hormone, Leptin, may play a more significant role in mediating cartilage breakdown and OA (Dumond et al, 2003 and Teichtahl et al., 2005). The 3 months post BTM period was therefore taken as the starting point for the evaluation of the relative effects of intra-articular injections of HA or MPC+HA on the rate of progression of cartilage pathology 12 and 24 weeks following the administration of these agents.

The results of this study indicated that a single intra-articular injection of 100 million MPC dispersed in 2 mL HA and 2 mL Profreeze® (a commercial cryoprotectant) into joints with established, severe OA can, over an intervening period of 24 weeks, slow the progression of joint pathology and enhance growth and/or regeneration of proteoglycan-rich cartilage to a greater extent than a single injection of 2 mL HA. Surprisingly, the growth/regenerative and chondroprotective effects mediated by the MPC were observed to be more significant 24 weeks after administration than after 12 weeks in the majority of parameters examined, indicating progressive effects which had not yet reached a plateau phase. The reasons for this finding are presently unclear however, it is possible that the growth factors such as members of the TGF-beta superfamily, eg BMPs, released by the MPC (Ahrens et al., 1993; Aggarwal et al., 2005) were supportive of the anabolic (compensatory) phase of cartilage to the altered mechanical stresses imposed across the joint by medial meniscectomy. This view was supported by the histomorphometric data that demonstrated the presence of higher volumes and more intense staining for proteoglycans in the MPC injected groups than at the commencement of treatment at 12 weeks post-BTM. These matrix changes are consistent with increase chondrocyte biosynthesis. Significantly, the magnitude of the anabolic parameters was generally found to be greater in the cartilages of animals who received the MPC+ HA rather than HA alone. The ability of MPC to preserve and even enhance this cartilage response to mechanical overload contrasts with the known inhibitory effects on chondrocyte metabolism mediated by many traditional treatments of OA, including many of the steroidal and non-steroidal anti-inflammatory drugs (NSAIDs) (McKenzie et al., 1976; Ghosh, 1988; Brandt, 1993 and 1993a; Huskisson et al., 1995).

Multiple intra-articular HA injections have been used as a therapy for the management of knee OA for more than 30 years. Although the consensus is that this form of treatment does provide symptomatic relief clinically, a recent review and a meta-analysis of published HA clinical trials have questioned the validity of this conclusion on the basis of the stronger placebo effects associated with intra-articular injections, difficulty of blinding investigators and publication biases (Brandt et al., 2000; Lo et al., 2003). Whether intra-articular HA exhibits any chondroprotective or cartilage regenerative activity is also controversial. However, extensive animal investigations have shown that HA does exhibit analgesic, anti-inflammatory and disease modifying effects in rabbit and ovine models of OA induced by uni-lateral and bilateral meniscectomy as well as anterior cruciate ligament transection in dogs. A discussion of these data together with preclinical and laboratory based clinical studies with HAs of different molecular weight has been reviewed (Ghosh et al., 2002).

In the present study only a single intra-articular injection of HA, either alone or in combination with MPC, was evaluated. On the basis of our own data we conclude that the long-lasting growth and regenerative, as well as chondroprotective, effects afforded by the MPC+HA combination was mediated by the MPC. In this regard it is important to note that the design of this study allowed each animal to act as its own control since one joint received HA while the contra-lateral joint received the same quantity of HA plus the MPC in the cryoprotectant, Profreeze®. Since both knee joints were surgically de-stabilised in the present study and were injected at the same time we are confident that the magnitude and nature of the weight-bearing mechanical stresses acting on the articular cartilages was the same on both joints.

From the present studies we conclude that a single intra-articular administration of MPC+HA into ovine joints with pre-existing, severe OA results in growth or regeneration of proteoglycan-rich cartilage as manifest by increased cartilage extracellular matrix 24 weeks post treatment relative to baseline pre-treatment and to HA injected controls.

Example 4

Ovine Disc Re-Generation Studies Using Immunoselected MPC

Methods

Figure 25:
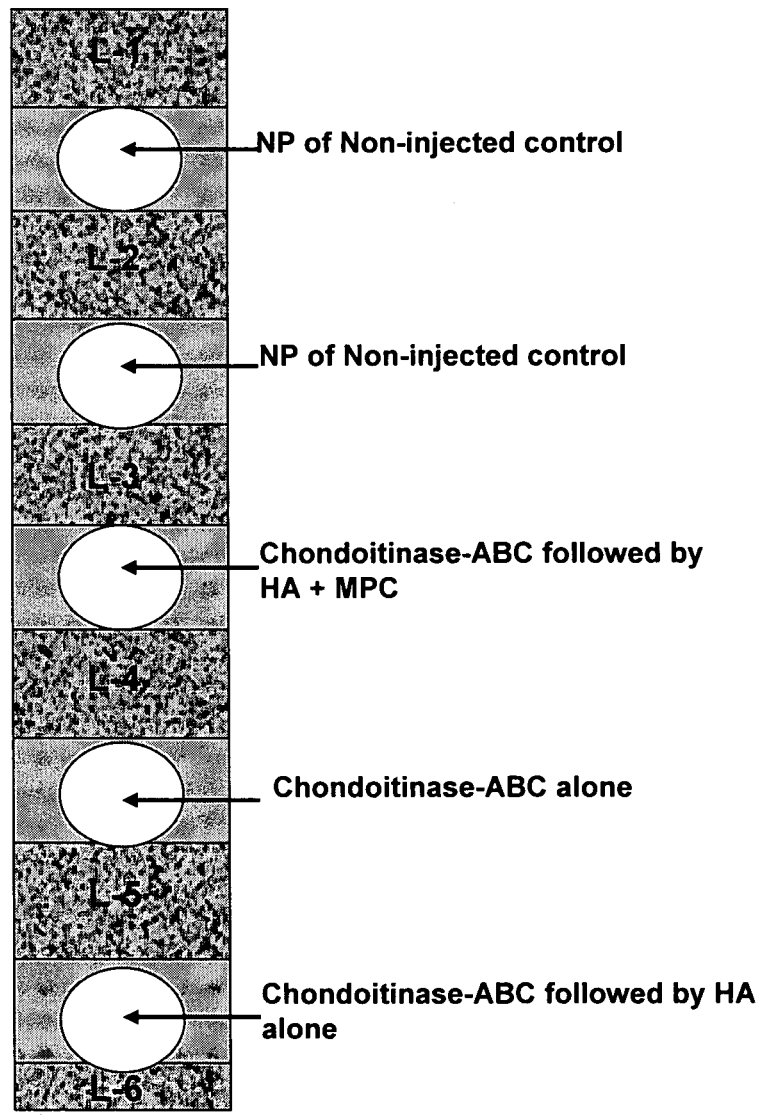
FIG. 25. Schematic representation of the lumber spinal levels treated with Mesenchymal Precursor Cells (MPC) in all sheep Groups.

Thirty-six age-matched, Merino wethers (approximately 18 to 24 months old) were used for this study. In all 36 sheep three adjacent lumbar discs (L3-L4, L4-L5, L5-L6) were injected with 1.0 IU chondroitinase ABC (Seikagaku Corporation, Japan) in approximately 0.1 ml sterile normal saline to breakdown and remove the PGs of the NP. The remaining lumbar discs (L1-L2 and L2-L3) were not injected with chondroitinase ABC and served as controls. Fifteen weeks (±3 weeks) following administration of chondroitinase ABC, injections MPCs ($0.5 \times 10^6$ cells) in ProFreeze™ Freezing Medium (NAO) or ProFreeze™ NAO alone (Lonza Walkersville Ltd.) mixed with an equal volume of hyaluronic acid (Euflexxa®, (Ferring Pharmaceuticals) were administered directly into the chondroitinase ABC treated nuclei pulposi of the intervertebral discs identified schematically in FIG. 25. The respective experimental groups were sacrificed 3 and 6 months later as summarized in Table 1.

TABLE 1

Study Design Summary

| Group | No. | Disc | 15 ± 3 weeks before Baseline | Baseline Day 0 | Sacrifice | Analysis at Sacrifice |
|---|---|---|---|---|---|---|
| 1 | n = 6 | L1-L2 | No injection | No injection | 3 mths | Compositional/Histology |
|   |   | L2-L3 | No injection | No injection | 3 mths | Compositional/Histology |
|   |   | L3-L4 | Chondroitinase | MPCs $0.5 \times 10^6$ | 3 mths | Compositional/Histology |
|   |   | L4-L5 | Chondroitinase | No injection | 3 mths | Compositional/Histology |
|   |   | L5-L6 | Chondroitinase | HA and NAO | 3 mths | Compositional/Histology |
| 2 | n = 6 | L1-L2 | No injection | No injection | 6 mths | Compositional/Histology |
|   |   | L2-L3 | No injection | No injection | 6 mths | Compositional/Histology |
|   |   | L3-L4 | Chondroitinase | MPCs $0.5 \times 10^6$ | 6 mths | Compositional/Histology |
|   |   | L4-L5 | Chondroitinase | No injection | 6 mths | Compositional/Histology |
|   |   | L5-L6 | Chondroitinase | HA and NAO | 6 mths | Compositional/Histology |

Animals had lateral plain radiographs taken of the lumbar spine under induction anaesthesia at the following time points: Day 0 (Injection of chondroitinase ABC (Seikagaku Corporation, Japan), Day of Test Article administration (15±3 weeks following induction of lumbar disc degeneration) and 3 months and 6 months following implantation of the Test Article. Evaluation of the radiographs was undertaken using an index of intervertebral height (DHI) calculated by averaging the measurements from the anterior, middle and posterior parts of the IVD and dividing it by the average of the adjacent intervertebral body heights as described by (Masuda et al., 2004).

The MRIs were taken of the lumbar spine under induction anaesthesia at the following time points: Day Zero (injection of chondroitase ABC [Seikagu Corp Japan]), Day of test article administration (15+3 weeks following induction of lumbar disc degeneration), 3 months and 6 months following implantation of test article. Disc were graded from the MRI scans using the Pfirrmann Classification System (Pfirrmann et al., 2001).

Spinal motion segments that were designated for histochemical and biochemical analysis were isolated by cutting through the cranial and caudal vertebral bodies close to the cartilaginous endplates using a bone saw. These spinal sections were fixed en bloc in Histochoice® for 56 h and decalcified in several changes of 10% formic acid in 5% Neutral Buffered Formalin for 2 weeks with constant agitation until complete decalcification was confirmed using a Faxitron HP43855A X-ray cabinet (Hewlett Packard, McMinnville, USA).

Multiple sagittal slices of the decalcified specimens, approximately 5 mm thick, were dehydrated through graded ethanol solutions by standard histological methods and embedded in paraffin wax. Paraffin sections 4 µm thick were mounted on Superfrost Plus glass microscope slides (Menzel-Glaser), dried at 85° C. for 30 min then at 55° C. overnight. The sections were then deparaffinised in xylene (4 changes×2 min) and rehydrated through graded ethanol washes (100-70% v/v) to tap water. One section from all blocks prepared from the sagittal slices was stained with haematoxylin and eosin. The coded section was examined by an independent histopathologist who compared the histological characteristics of those levels that were subjected to enzyme injection only with those that were enzyme-injected and subsequently received MPCs. A four-point semi-quantitative grading system was used to assess the microscopic features of the entire disc as shown in Table 2. Additional tinctorial stains including Alcian Blue (for general glycosaminoglycan species) and Safranin O (specific for chondroitin sulphate species) were also prepared to demonstrate the extent of disc matrix synthesis.

The immunohistochemistry procedures were also performed using a Sequenza cassette and disposable Coverplate immunostaining system as described previously (Melrose et al., 2003; Melrose et al., 2002; Melrose et al., 2000; Melrose et al., 2002a; Melrose et al., 1998; Panjabi et al., 1985; Race et al., 2000; Smit, 2002). Endogenous peroxidase activity was initially blocked by incubating the tissue sections with 3% $H_2O_2$. They were then pre-digested with combinations of chondroitinase ABC (0.25 U/ml) in 20 mM Tris-acetate buffer pH 8.0 for 1 h at 37° C., bovine testicular hyaluronidase 1000 U/ml for 1 h at 37° C. in phosphate buffer pH 5.0, followed by three washes in 20 mM Tris-HCl pH 7.2 0.5M NaCl (TBS) or proteinase-K (DAKO S3020) for 6 min at room temperature to expose antigenic epitopes. The tissues were then blocked for 1 h in 20% normal swine serum and probed with a number of primary antibodies to large and small proteoglycans and collagens (Table 3). Negative control sections were also processed either omitting primary antibody or substituting an irrelevant isotype matched primary antibody for the authentic primary antibody of interest. Commercial (DAKO) isotype matched mouse IgG (DAKO Code X931) or IgM (DAKO Code X942) control antibodies (as appropriate) were used for this step. The DAKO products X931 and X942 are mouse monoclonal $IgG_1$ (clone DAK-GO1) and monoclonal IgM (clone DAK-G08) antibodies directed against *Aspergillus niger* glucose oxidase, an enzyme that is neither present nor inducible in mammalian tissues. Horseradish peroxidase or alkaline phosphatase conjugated secondary antibodies were used for the detection using 0.05% 3,3'-diaminobenzidene dihydrochloride and 0.03% $H_2O_2$ in TBS, Nova RED, nitroblue tetrazolium/5-bromo-4-chloro-3-indolyl phosphate/iodo nitrotetrazolium violet (NBT/BCIP/INT) or New Fuchsin as substrates. The stained slides were examined by bright field microscopy and photographed using a Leica MPS 60 photomicroscope digital camera system.

TABLE 2

Grading system of histologic changes in lower lumbar discs (BEP bony end-plate, CEP cartilaginous end-plate)

| Grade | Annulus fibrosis | Nucleus pulposus | Cartilage end-plate | Margins/subchondral bone |
|---|---|---|---|---|
| 1 | Intact lamellae<br>Narrow inter-lamellar matrix<br>Intact annulus attachment<br>Vessels only in outer 1/3 | Homogeneity<br>Absence of clefting | Uniform thickness<br>Intact attachment to bone<br>Uniform calcification <1/3 of depth<br>Uniform cell distribution | Even thickness of BEP<br>Lamellar bone only<br>Distinct junction with CEP<br>Few vascular intrusions into CEP |
| 2 | Minor lamellar splitting and disorganisation. Minor widening of matrix Minor disorganisation of attachment Rim lesion without reparative reaction | Minor clefting<br>Minor cell necrosis<br>Minor posterior displacement of annulus<br>Minor chondrone formation | Minor cartilage thinning<br>Small transverse fissures<br>Irregular thickening of calcified zone<br>Few invading vascular channels<br>Small chondrones | Slightly uneven BEP<br>Schmorl's nodes<br>Minimal remodelling of BEP<br>Small marginal osteophytes |
| 3 | Moderate widening of matrix moderate fissuring of attachment Radiating tears not involving outer 1/3 minimal chondroid metaplasia Cystic degeneration Vessels in outewr and middle 1/3 rim lesion with minor reparative reaction | Moderate clefting<br>Moderate cell necrosis<br>Cystic degeneration<br>Posterior displacement within annulus<br>Centripetal extension of collagen<br>Moderate chondrone formation | Marked cartilage thinning<br>Marked thickening of calcified zone<br>Many transverse fissures<br>Many vascular channels<br>Many chondrones | Moderately uneven BEP<br>Vascularised Schmorl's nodes<br>Moderate trabecular thickening<br>Defect in bone lamellae<br>Minimal fibrosis tissue in marrow spaces<br>Medium-size osteophytes |
| 4 | Extensive lamellar disorganisation<br>Radiating tears extending into outer 1/3<br>Extensive chondroid metaplasia<br>Vessels in all zones<br>Rim lesion with marked reparative reaction | Complete loss of nucleus<br>Loose body formation<br>Marked chondrone formation | Total loss of cartilage<br>Calcification of residual cartilage<br>Widespread fissuring | Marked uneven BEP<br>Ossified Schmorl's nodes<br>Large osteophytes<br>Marked trabecular thickening<br>Marked fibrosis of marrow spaces<br>Cartilage formation |

TABLE 3

Primary antibodies to proteoglycan and collagen core protein epitopes

| Primary antibody epitope | Clone (isotype) | References |
|---|---|---|
| Large PGs | | |
| Aggrecan | AD 11-2A9 (IgG) | 26, 30 |
| Versican | 12C5 (IgG) | 26, 28 |
| Collagen | | |
| Type I | I8H5 (IgG$_1$) | 23, 28 |
| Type II | II-4CII (IgG$_1$) | 28 |
| Type IV | CIV-22 (IgG$_1$) | 28 |
| Type VI | Rabbit polyclonal | 28 |
| Type IX | Mouse monoclonals D1-9 (IgG$_1$), B3-1 (IgG$_{2b}$) | 35 |

Samples of annulus fibrosus and nucleus pulposus were dissected from the processed blocks finely diced and representative portions of the tissue zone of known wet weight were freeze dried to constant weight. Triplicate portions (1-2 mg) of the dried tissues were hydrolysed in 6M HCl at 110° C. for 16 h and aliquots of the neutralised digests assayed for hydroxyproline as a measure of the tissue collagen content (Sakai et al., 2005). Triplicate portions of dried tissues (~2 mg) will also be digested with papain and aliquots of the solubilised tissue assayed for sulphated glycosaminoglycan using the metachromatic dye 1,9-dimethylmethylene blue as a measure of PGs (Sakai et al., 2005).

The motion segments were wrapped in saline-soaked gauze, sealed in double thickness polythene bags and frozen at −30° C. until biomechanical testing. This treatment has been shown not to alter the biomechanical characteristics of the tissue (Panjabi et al., 1985). Biomechanical testing was undertaken to measure the stiffness of each disc in axial compression, flexion, extension, lateral bending and axial torsion under defined computer-controlled conditions approximating physiological loading (Panjabi et al., 1985; Race et al., 2000; Smit, 2002; Wilke et al., 1999). Full details of the testing protocol are documented elsewhere (Panjabi et al., 1985; Race et al., 2000; Smit, 2002; Wilke et al., 1999). The specimens for testing (functional spinal units, FSUs) comprised two adjacent vertebrae, the intervening disc and associated ligaments. Three FSUs per spine were tested: a level that was only degraded with C-ABC only, one in which the disc was degraded with C-ABC and which was subsequently treated with hyaluronic acid only and the central level that was degraded with C-ABC and which was subsequently treated with hyaluronic acid and with MPCs. Each FSU was mounted in two aluminium alloy cups and secured with three bolts and cold cure polymethyl methacrylate dental cement (Vertex SC Self Curing, Dentimex BV, Zeist, Holland). Care was taken to ensure that the midline of the intervertebral disc is positioned horizontally. The motion segments will be centred in the cups by placing a dowel through the vertebral canal into a hole in one of the cups. All tests were conducted in a saline water bath maintained at 37° C. Prior to the commencement of testing each FSU will be preloaded to a stress of 0.5 MPa until a reproducible state of hydration is achieved. This was used as the baseline prior to each test. The preload stress of 0.5 MPa simulates relaxed standing and was based on in vivo measurement of intradiscal pressure.

Mechanical tests were performed using a Model 8511 Dynamic Servohydraulic Materials Testing Machine (INSTRON Pty Ltd, High Wycombe, UK) equipped with a 'six degrees of freedom' load cell to allow the simultaneous monitoring and control of forces in all three planes. The machine was controlled by a personal computer and custom-designed software that also records and analyses the data. Test data was acquired in stable hysteresis from the final of five sinusoidal 0.1 Hz loading cycles in either axial load or torsion control. The tests were performed are pure axial compression, left and right lateral bending, combined flexion/extension and pure axial torsion.

Pure axial compression to 200N was produced in the FSU with little or no bending or flexion accompanying the load. All compressive tests were performed using point contact on the cranial cup surface. The neutral axis of bending (NAB) is determined by applying a cyclic load to the joint through a point on the aluminium alloy cup holding the specimen to achieve negligible bending. This trial and error process enables as close to pure axial compression as possible using a rigid point load contact. Despite slight variability between specimens this point is found on the sagittal plane approximately 10 mm anterior to the spinal canal but slightly posterior to the disc centroid. Marks were placed 10 mm anterior and posterior and to the left and right of the NAB to position the offset loads for the bending tests. A maximum compressive load of 200 N was applied at each point to produce 2 Nm of bending and 200 N of axial compression.

Conservative bending and compressive loads were chosen to ensure that the disc, posterior elements, endplates and other ligamentous structures were not e damaged. Pure bending was not produced using this loading method. Instead a combination of bending and axial compression was present for the combined flexion/extension and lateral bending tests. We believe this was justified given that in vivo loading would seldom produce pure bending but rather a combination of compression and bending. In either load case, all loads were applied consistently to each specimen allowing direct comparisons of the mechanical response.

For the torsion tests 5 Nm of pure axial torsion will be applied. This was within the physiological range of torques estimated from, and applied in, other studies. A novel custom designed torsion testing system will be used to apply pure torsion to each FSU. This system uses a ballscrew/thrust plate mechanism to convert the axial displacement of the Instron actuator into pure rotation. An X-Y bearing table ensures that the FSU does not have a fixed centre of rotation imposed on it during testing. This is important, as the centre of rotation is not constant during axial rotation. The inferior cup was fixed to a torque transducer with the superior cup fixed to the X-Y bearing table and ballscrew/thrust plate mechanism.

All tests were conducted on the intact FSU initially. Once completed the disc were isolated by cutting through the posterior elements using a small hacksaw blade passed through the neural foramen and cutting posteriorly. This cut through the zygapophysial joints and the interspinous and supraspinous ligaments, leaving the intervertebral disc, the posterior and the anterior longitudinal ligaments intact. The cut was made in a wedge fashion increasing posteriorly to ensure no contact between the zygapophyseal joints. All tests were then repeated on the isolated disc.

Data analysis included parameters such as stiffness in the linear region during the fifth loading cycle, hysteresis and strain energy and the extent of the neutral zone. Data from the control levels was compared with the degenerated/MPC-injected levels and repeated measures analysis of variance was conducted on each of the biomechanical parameters.

Results

All animals in the MPC injected groups maintained normal body weights and showed no evidence of adverse side effects over the duration of the experiment.

Figure 26:
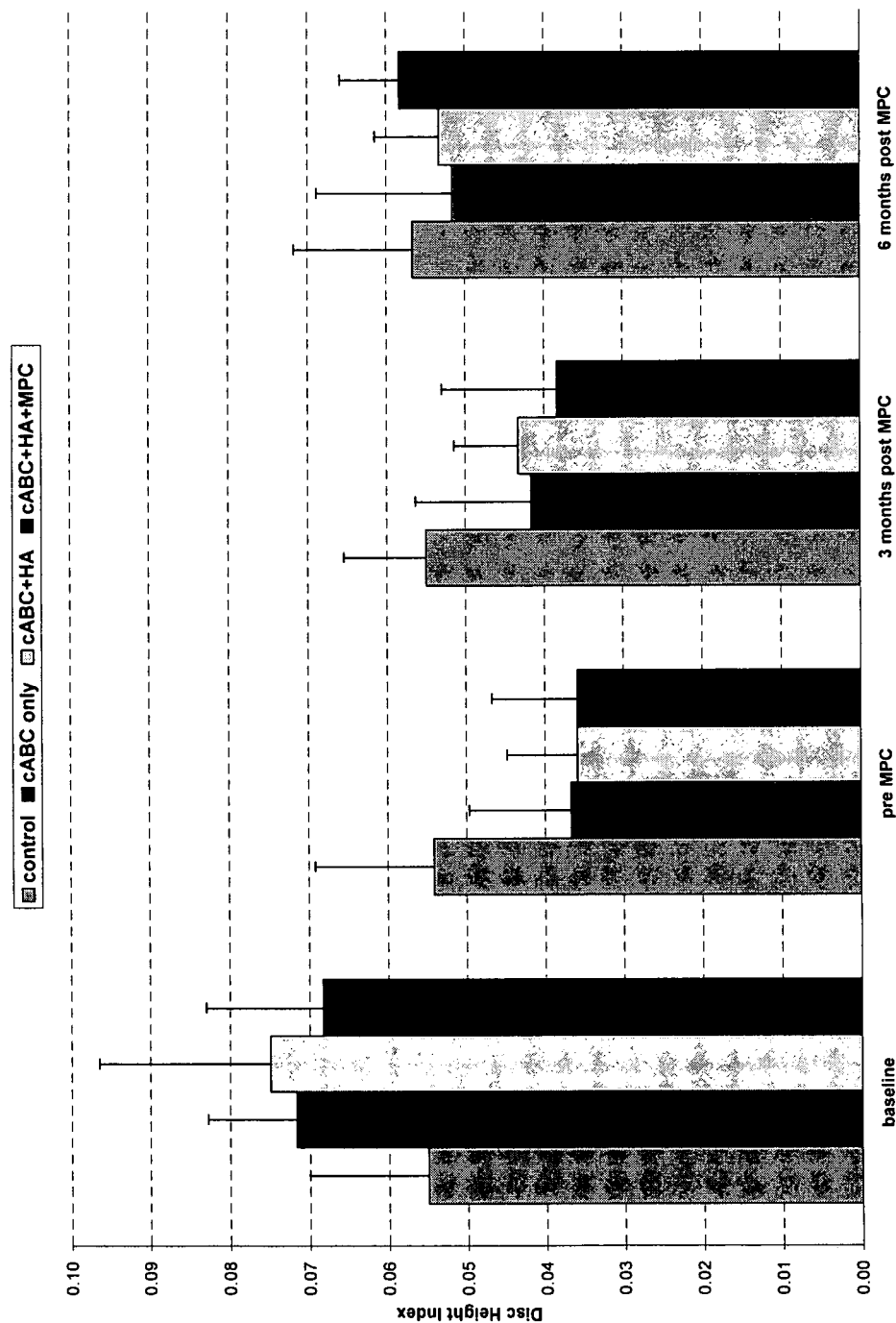
FIG. 26. Mean recovery in disc height three and six months following injection of MPC and HA into the nuclei pulposi of degenerate sheep discs.

In the Chondroitinase-ABC injected discs the depletion of PGs by this enzyme resulted in a 38% decrease in disc height index (DHI) in all injected discs after 3 months. This loss of disc height confirmed the degenerate status of the nucleus pulposus prior to treatments and hitherto is referred to as the pre-MPC DHI. Three months post HA or MPC+HA injection into the degenerate discs failed to produce any significant increase in DHI relative to the pre-MPC DHI (FIG. 26). However, by 6 months post treatment, discs injected with MPC+HA showed a mean increase of 52% in DHI relative to the corresponding 3 month scores (Group 1) (FIG. 26 and Table 4). In contrast, discs injected with HA alone only showed a 23.1% mean improvement in the DHI scores over the same period (FIG. 26 and Table 4). Significantly, the mean DHI of the low MPC+HA injected discs were comparable 6 months post treatment to the DHA scores for the non-chondroitinase ABC injected (ie, non-degenerate) control discs (FIG. 26).

A statistical analysis for the DHI for 6 versus 3 months post HA or MPC+HA injection is shown in Table 4.

Administration of ovine MPC together with a suitable carrier, such as high molecular weight hyaluronic acid (HA), into the nucleus pulposus of experimentally created degenerate IVDs has been shown in the present experiments to accelerate the regeneration of the disc extracellular matrix as assessed radiographically by the recovery of disc height. This interpretation is based on the assumption that in the loaded spinal column the disc height is maintained by the presence within the NP and inner-annulus of high concentrations of matrix proteoglycans that together with their bound water molecules confer a high swelling pressure to this structure. Indeed, the use of chondroitinase-ABC to induce disc degeneration at the commencement of these experiments relied on the ability of this enzyme to degrade and remove the majority of the proteoglycans from the NP extracellular matrix.

The data obtained to date suggests that the therapeutic effect mediated by the MPC is a relatively slow process. In the present study, the dose of $0.5 \times 10^6$ MPC was particularly effective.

Although the present experiments were terminated 6 months after the MPC were injected into the disc, the level of disc height recovery obtained for the low dose MPC injections was found to be close to the values observed for the non-chondroitinase ABC injected internal controls, suggesting that the maximum extent of NP reconstitution was achieved over this period.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

TABLE 4

Extent of disc height restoration 3 and 6 months post intra-discal injection of Mesenchymal Precursor Cells (MPC) + Hyaluronan (HA) or HA alone into degenerate sheep lumber discs

| | PRE-MPC INJECTION DHI | | | | 3 MONTHS POST MPC INJECTION DHI | | | | 6 MONTHS POST MPC INJECTION DHI | | | |
|---|---|---|---|---|---|---|---|---|---|---|---|---|
| | Non-injected | cABC only | cABC + HA | cABC + HA + MPC | Non-injected | cABC only | cABC + HA | cABC + HA + MPC | Non-injected | cABC only | cABC + HA | cABC + HA + MPC |
| MEAN | 0.054 | 0.04 | 0.04 | 0.04 | 0.055 | 0.0416667 | 0.0433333 | 0.0383333 | 0.0566667 | 0.0516667 | 0.0533333 | 0.05833333 |
| Std Deviation | 0.015 | 0.01 | 0.01 | 0.01 | 0.01 | 0.014 | 0.008 | 0.014 | 0.015 | 0.017 | 0.008 | 0.007 |
| % Change from 3 months to 6 months | | | | | | | | | 0.2 | 23.9 | 23.1 | 52.174 |
| Statistical Significance (P values) | | | | | | | | | 0.83 | 0.31 | 0.059 | 0.0142 |

$P < 0.05$ = significant
DHI = Disc Height Index
cABC = Chondroitinase ABC

REFERENCES

Aggarwal et al. (2005) Blood. 105: 1815-1822.
Ahrens et al. (1993) DNA Cell Biol. 12: 871-880.
Allcock et al. (1977) Macromolecule 10:824.
Anseth et al. (2002) J. Control Release 78:199-209.
Appleyard et al. (1999) Osteoarthritis and Cartilage 7:281-294.
Appleyard et al. (2003) Osteoarthritis Cartilage 11: 65-77.
Arnoczky et al. In: Injury and repair of the musculoskeletal soft tissues. Eds, Woo S L-Y and Buckwalter. American Academy of Orthopaedic Surgeons, Park Ridge, Ill.: 1988, pp. 487-537.
Bellamy et al. (2006) Cochrane Database Syst Rev 2006(2): CD005321
Brandt (1993) Agents and Actions 40: 232-234.
Brandt (1993a) Rheumatic Disease Clinics of North America. 19:29-44.
Brandt et al. (2000) Arthritis Rheum. 43: 1192-1203.
Bregni et al., Blood 80:1418-22.
Burkhardt et al. (2001) Osteoarthritis Cartilage 9: 238-47.
Cake et al. (2000) Osteoarthritis Cartilage 8: 404-411.
Cake et al. (2003) Osteoarthritis and Cartilage 11: 872-8.
Cake et al. (2004) Osteoarthritis and Cartilage 12: 974-81.
Cake et al. (2005) Osteoarthritis Cartilage 13: 1066-75.
Cake et al. Clinical and Experimental Rheumatology 2008 (in press).
Dumond et al. (2003) Arthritis Rheum. 48: 3009-12.
Englund (2004) Arthritis Rheum 50:2811-9.
Ghosh et al. (1983) J Orthop Res 1: 153-173.
Ghosh et al. (1983a) J Surg Res 35:461-473.
Ghosh (1988) In: Bailliere's Clinical Rheumatology, International Practice and Research. Ed. P Brooks, Tindall, Saunders, London, UK, pp 309-338.
Ghosh et al. (1990) Clin. Orthop. 252: 101-113.
Ghosh (1991) J. Rheumatol. 18:143-6.
Ghosh et al. (1993) Curr. Ther. Res. 54: 703-713.
Ghosh et al. (1993a) Semin. Arthritis Rheum. 22 (Suppl. 1): 18-30.
Ghosh et al. (1993b) Semin Arthritis Rheum 22 (Suppl 1): 31-42.
Ghosh et al. (1993c) Agents Actions Suppl 39: 89-93.
Ghosh et al (2002) Semin. Arthritis Rheum. 32: 10-37.
Gronthos et al. (1995). Blood 85:929-940.
Gronthos et al. (2003) Journal of Cell Science 116: 827-1835.
Huskisson et al. (1995) Journal of Rheumatology 22:1941-6.
Hwa et al. (2001) J. Rheumatol. 28: 825-834.
Jorgensen et al. (1987) J Bone Joint Surg Br. 69: 80-3.
Little et al. (1997) J. Rheumatol. 24: 2199-2209.
Lo et al. (2003). JAMA. 290:3115-3127.
Masuda et al. (2004) Spine 30:5-14.
McKenzie et al. (1976) Ann. Rheum. Dis. 35: 487-497.
McNicholas et al. (2000) J Bone Joint Surg Br. 82: 217-21.
Melrose et al. (2003) J Histochem Cytochem 5:1331-1341.
Melrose et al. (2002) Spine 27:1756-1764.
Melrose et al. (2000) Histochem Cell Biol 114:137-46.
Melrose et al. (2002a) Histochem Cell Biol 117:327-33.
Melrose et al. (1998) J Vasc Surg 28:676-686.
Moon et al. (1984) Clin Orthop Related Res 182:264-9.
Nevitt et al. (1996) Arch Intern Med 156: 2073-80.
Oakley et al. (2004) Osteoarthritis Cartilage 12: 667-79.
Parker et al. (2003) J. Rheumatol. 6(2): 116-127.
Pelletier et al. (2007) Arthritis Res Ther. 9: R74.
Pfirrmann et al. (2001) Spine 26:1873-1878.
Panjabi et al. (1985) J Orthop Res 3:292-300.
Race et al. (2000) Spine 25:662-9.
Richette and Bardin (2004) Joint Bone Spine 71:8-23.
Roos et al. (1998) Arthritis Rheum 41: 687-93.
Roos et al. (2001) Osteoarthritis and Cart. 9: 316-24.
Sakai et al. (2005). Spine 30:2379-87.
Simmons et al. (1994) Advances in Bone Marrow Purging and Processing: Fourth International Symposium, 271-280.
Smit (2002) Eur Spine J 11:137-44.
Smith and Ghosh (2001) Experimental models of osteoarthritis in: Osteoarthritis, Eds: Moskowitz et al. WB Saunders Company; pp 171-199.
Smith et al. (1997) Pathol. Biol. [Paris]. 45: 313-320.
Teichtahl et al. (2005) Medical Hypothesis 65: 312-12.
Wang et al. (2003) Biomaterials 24:3969-3980.
Wilke et al. (1999) Spine 24:755-62.
Zannettino et al. (1998) Blood 92:2613-2628.

The invention claimed is:

1. A method of treating a disease in a subject arising from degradation and/or inflammation of connective tissue, the method comprising administering to the subject a population of cells which have bright been enriched for STRO-1$^{bright}$ multipotential cells or progeny cells thereof, wherein paracrine activities of the administered population of cells protect or stimulate growth and/or regeneration of the connective tissue wherein the disease is selected from the group consisting of osteoarthritis, rheumatoid arthritis, psoriatic arthritis, seronegative arthritis, and arthritis associated with inflammatory bowel disease, and bright wherein the population of cells enriched for STRO-1$^{bright}$ multipotential cells or progeny cells thereof are administered by intra-articular injection to a joint space of the subject, wherein the joint space is in a knee joint, hip joint, ankle joint, shoulder joint, elbow joint, wrist joint, hand or finger joint or a joint of the foot; and wherein the administration of the population of cells enriched for STRO-1$^{bright}$ multipotential cells or progeny cells thereof results in preservation or generation of connective tissue that is rich in proteoglycans in the joint space of the subject.

2. The method of claim 1, wherein the connective tissue is rich in proteoglycans.

3. The method of claim 1, wherein the connective tissue is cartilage.

4. The method of claim 3, wherein the disease results in one or more defects in the cartilage.

5. The method of claim 1, wherein the connective tissue that is rich in proteoglycans is hyaline cartilage.

6. The method of claim 1, which further comprises administering a chondroprotective agent.

7. The method of claim 6, wherein the chondroprotective agent is hyaluronic acid (HA).

8. A method of treating a disease in a subject arising from degradation and/or inflammation of connective tissue, comprising administering to the subject a population of cells enriched for STRO-1$^{bright}$ multipotential cells or progeny cells thereof, wherein the disease is selected from the group consisting of osteoarthritis, rheumatoid arthritis, psoriatic arthritis, seronegative arthritis, and arthritis associated with inflammatory bowel disease, wherein the population of cells enriched for STRO-1$^{bright}$ multipotential cells or progeny cells thereof are administered to a joint space, and wherein the joint space is in a knee joint, hip joint, ankle joint, shoulder joint, elbow joint, wrist joint, hand or finger joint or a joint of the foot; and wherein the administration of the population of cells enriched for STRO-1$^{bright}$ cells or progeny cells thereof results in preservation or generation of connective tissue that is rich in proteoglycans in the joint space of the subject.

9. The method of claim 8, wherein the connective tissue is cartilage.

10. The method of claim 9, wherein the disease results in one or more defects in the cartilage.

11. The method of claim 8, wherein the population of cells enriched for STRO-1$^{bright}$ multipotential cells or progeny cells thereof are administered by intra-articular injection.

12. The method of claim 8, wherein the connective tissue that is rich in proteoglycans is hyaline cartilage.

13. The method of claim 8, which further comprises administering a chondroprotective agent.

14. The method of claim 13, wherein the chondroprotective agent is hyaluronic acid (HA).

* * * * *